US011016091B2

(12) United States Patent
Parenteau et al.

(10) Patent No.: US 11,016,091 B2
(45) Date of Patent: May 25, 2021

(54) IDENTIFICATION, SELECTION AND USE OF HIGH CURATIVE POTENTIAL T CELL EPITOPES

(71) Applicant: Verik Bio, Inc., Newton, MA (US)

(72) Inventors: Nancy Parenteau, Fair Haven, VT (US); Joseph Laning, Southborough, MA (US); Janet Young, Boerne, TX (US)

(73) Assignee: VERIK BIO, INC., Newton, MA (US)

( * ) Notice: Subject to any disclaimer, the term of this patent is extended or adjusted under 35 U.S.C. 154(b) by 44 days.

(21) Appl. No.: 16/436,344

(22) Filed: Jun. 10, 2019

(65) Prior Publication Data

US 2019/0353655 A1 Nov. 21, 2019

Related U.S. Application Data

(63) Continuation of application No. 14/958,780, filed on Dec. 3, 2015, now Pat. No. 10,317,402.

(60) Provisional application No. 62/087,002, filed on Dec. 3, 2014.

(51) Int. Cl.
| | | |
|---|---|---|
| *A61K 35/17* | (2015.01) | |
| *C07K 14/47* | (2006.01) | |
| *G01N 33/569* | (2006.01) | |
| *A61K 39/00* | (2006.01) | |
| *G01N 33/50* | (2006.01) | |
| *G01N 33/574* | (2006.01) | |

(52) U.S. Cl.
CPC ....... *G01N 33/56972* (2013.01); *A61K 35/17* (2013.01); *A61K 39/00* (2013.01); *A61K 39/0011* (2013.01); *C07K 14/47* (2013.01); *G01N 33/505* (2013.01); *G01N 33/5011* (2013.01); *G01N 33/574* (2013.01); *G01N 2333/912* (2013.01); *G01N 2333/96433* (2013.01)

(58) Field of Classification Search
CPC ..... A61K 35/17; A61K 39/0011; C07K 14/47
USPC ........................................................ 424/93.7
See application file for complete search history.

(56) References Cited

U.S. PATENT DOCUMENTS

| | | |
|---|---|---|
| 2010/0040641 A1 | 2/2010 | Tsunoda |
| 2012/0263757 A1 | 10/2012 | Chiriva-Internati |

FOREIGN PATENT DOCUMENTS

| | | |
|---|---|---|
| WO | 20060032923 | 3/2006 |
| WO | 2013126785 | 8/2013 |
| WO | 2014127006 | 8/2014 |

OTHER PUBLICATIONS

Abate-Dega, et al., "Development of a T cell receptor targeting an HLA-A*0201 restricted epitope from the cancer-testis antigen SSX2 for adoptive immunotherapy of cancer", PLoS ONE, 9:93321 (2014).
Adem, et al. "ETV6 rearrangements in patients with infantile fibrosarcomas and congenital mesoblastic nephromas by fluorescence in situ hybridization", Mod Pathol., 14(12):1246-51 (2001).
Agarwal, et al., "Expression and humoral response of A-kinase anchor protein 4 in cervical cancer", Int. J. Gynecol. Cancer 23(4):650-8 (2013b).
Agarwal, et al., "The novel cancer-testis antigen A-kinase anchor protein 4 (AKAP4) is a potential target for immunotherapy of ovarian serous carcinoma", Oncolmmunology, 2(5):e24270 (2013).
Ambatipudi, et. al., "Genome-wide expression and copy number analysis identifies driver genes in gingivobuccal cancers", Genes Chromosomes Cancer. 51(2): 161-73. (2012).
Andreatta, et al., "Gapped sequence alignment using artificial neural networks: application to the MHC class I system", Bioinformatics, pii: btv639 (2015).
Argani, et al., "Mesothelin is overexpressed in the vast majority of ductal adenocarcinomas of the pancreas: identification of a new pancreatic cancer marker by serial analysis of gene expression (SAGE)", Clin. Cancer Res. 7:3862-8 (2001).
Atanackovic, et al., "Expression of cancer-testis antigens as possible targets for antigen-specific immunotherapy in head and neck squamous cell carcinoma", Cancer Biol Ther., 5(9):1218-25 (2006).
Barco, et al., "The synovial sarcoma-associated SYT-SSX2 oncogene antagonizes the polycomb complex protein Bmi1", PLos One, 4:5060 (2009).
Blocker, et al., "Congenital fibrosarcoma", J Pediatr Surg., 22:665-70 (1987).
Caretta, et al., "Protein kinase a in cancer", Cancers, 3:913-26 (2011).

(Continued)

*Primary Examiner* — Yan Xiao
(74) *Attorney, Agent, or Firm* — Pabst Patent Group LLP

(57) ABSTRACT

A method for identifying T-cell epitopes which can be used to elicit T cells targeting cells capable of regenerating cancers is disclosed. The method identifies T-cell epitopes with a high curative potential, high potency and high probability of T cell recognition (HP). The method includes: (i) identifying high curative potential tumor protein target i.e., identifying HP-TP; (ii) identifying peptide sequences within the protein sequence of an HP-TP that have a high probability of eliciting T cell killing; and (iii) qualifying the sequence specificity based on the fold difference between the specific target and non-targets. The identified T-cell epitopes include a core sequence of 9 amino acids homologous to a sequence expressed within a qualified HP-TP. The T-cell epitopes can be used in a method for reprograming T cells to selectively attack tumor cells capable of perpetuating a tumor and treating patients, for example, cancer patients.

3 Claims, 1 Drawing Sheet
Specification includes a Sequence Listing.

(56) References Cited

OTHER PUBLICATIONS

Casey, et al., "TMPRSS2-driven ERG expression in vivo increases self-renewal and maintains expression in a castration resistant subpopulation",. PLoS One, 7 (7):e41668 (2012).
Chang, et al., "Molecular cloning of mesothelin, a differentiation antigen present on mesothelium, mesotheliomas, and ovarian cancers", PNAS, 93:136-40 (1996).
Chiarle, et al., "The anaplastic lymphoma kinase in the pathogenesis of cancer", Nat Rev Cancer, 8:11-23 (2008).
Chiriva-Internati, et al., "AKAP-4: a novel cancer testis antigen for multiple myeloma", Br. J. Haematol. 140:464-74 (2008).
Chiriva-Internati, et al., "Identification of AKAP-4 as a new cancer/testis antigen for detection and immunotherapy of prostate cancer", The Prostate, 72 (1):12-23 (2012).
Cironi, et al., "Epigenetic features of human mesenchymal stem cells determine their permissiveness for induction of relevant transcriptional changes by SYT-SSX1", PLoS ONE, 4:7904 (2009).
Creaney, et al., "Serum soluble mesothelin concentrations in malignant pleural mesothelioma: relationship to tumor volume, clinical stage and changes in tumor burden", Clin. Cancer Res., 17:1181-9 (2011).
De Nooij-Van Dalen, et. al., "Characterization of the human Ly-6 antigens, the newly annotated member Ly-6K included, as molecular markers for head-and-neck squamous cell carcinoma", Int J Cancer. Mar. 1;103(6):768-74 (2003).
Delmore, et al., "BET bromodomain inhibition as a therapeutic strategy to target c-Myc", Cell, 146:904-17 (2011).
Euhus, et al., "ETV6-NTRK3—Trk-ing the primary event in human secretory breast cancer", Cancer Cell, 2:347-8 (2002).
Fujihara, et al., "GPI-anchored protein complex, LY6K/TEX101, is required for sperm migration into the oviduct and male fertility in mice", Biol Reprod.,, 90:60 (2014).
Gelebart, et al., "Aberrant expression and biological significance of Sox2,an embryonic stem cell transcriptional factor, in ALK-positive anaplastic large cell lymphoma", Blood Cancer J., 2:e82; doi:10.1038/bcj (2012).
Gumireddy, et al., "AKAP4 is a circulating biomarker for non-small cell lung cancer", Oncotarget, 6(19):17637-47 (2015).
Guo, et al., "Linking Transcriptional Elongation and Messenger RNA Export to Metastatic Breast Cancers", Cancer Res., 65:3011-6 (2005).
Hildebrand and Schaaf, "The urokinase-system in tumor tissue stroma of the breast and breast cancer cell invasion", Int. J. Oncology, 34:15-23 (2009).
Ho, et al., "Mesothelin expression in human lung cancer", Clin. Cancer Res. 13:1571-5 (2007).
Hoadley, et al., "Multiplatform analysis of 12 cancer types reveals molecular classification within and across tissues of origin", Cell, 158(4):929-44 (2014).
Hoffman, et al., "Genome-wide analysis of cancer/testis gene expression", PNAS,. 105(51):20422-7 (2008).
Hollevoet, et al., "Diagnostic performance of soluble mesothelin and megakaryocyte potentiating factor in mesothelioma.", Am. J. Respir. Crit. Care Med., 181:620-5 (2010).
Ishikawa, et. al., "Phase I clinical trial of vaccination with LY6K-derived peptide in patients with advanced gastric cancer", Gastric Cancer, 17(1):173-80 (2014).
Ishikawa, et. al., "Cancer-testis antigen lymphocyte antigen 6 complex locus K is a serologic biomarker and a therapeutic target for lung and esophageal carcinomas", Cancer Res., 67(24):11601-11 (2007).
Iwasaki, et al., "Synovial sarcoma translocation (SYT) encodes a nuclear receptor coactivator", Endocrinology, 146:3892-9 (2005).
Khaja, et al., "Cyclin A1 modulates the expression of vascular endothelial growth factor and promotes hormone-dependent growth and angiogenesis of breast cancer", PLoS ONE, 8(8):e72210 (2013).
Koberstein, et al., "Combination canceer immunotherapy—A virtual roundtable: Part 1", Life Science, magazine article, Sep. 2, 2014.

Kong, et al., "The regulatory mechanism of the LY6K gene expression in human breast cancer cells", J Biol Chem 287:38889-900 (2012).
Kosacka, et al., "Cyclin A and Cyclin E expression in resected non-small cell lung cancer stage I-IIIA", In Vivo, 23:519-26 (2009).
Lee, et. al., "LY-6K gene: a novel molecular marker for human breast cancer", Oncol. Rep., 16:1211-4 (2006).
Li, et al., "ETV6-NTRK3 fusion oncogene initiates breast cancer from committed mammary progenitors via activation of AP1 complex", Cancer Cell, 12:542-58 (2007).
Ling, et al., "Extremely high genetic diversity in a single tumor points to prevalence of non-Darwinian cell evolution", PNAS, 112(47):E6496-505 (2015).
Lou, et al., "Expression of cancer-testis genes in human hepatocellular carcinomas", Cancer Immun., 2:11 (2002).
Matsuda, et al., "LY6K is a novel molecular target in bladder cancer on basis of integrate genome-wide profiling", Br. J. Cancer, 104:376-86 (2011).
Mischo, et al., "Prospective study on the expression of cancer testis genes and antibody responses in 100 consecutive patients with primary breast cancer", Int J Cancer, 118(3):696-703 (2006).
Neary, et al., "Protein kinase A isozyme switching: eliciting differential cAMP signaling and tumor reversion", Oncogene, 23:8847-56 (2004).
Nielsen, et al., "Reliable prediction of T-cell epitopes using neural networks with novel sequence representations", Protein Sci., 12:1007-17 (2003).
Nipper, et al., "Protein domains govern the intracellular distribution of mouse sperm AKAP4", Biol Reprod., 75:189-196 (2006).
Ochsenreither, et al., "Relative quantification of TCR Vbeta-chain families by real time PCR for identification of clonal T-cell populations", J Transl Med., 6:34 (2008).
Ochsenreither, et al., "Cyclin-A1 represents a new immunogenic targetable antigen expressed in acute myeloid leukemia stem cells with characteristics of a cancer-testis antigen", Blood, 119(23):5492-5501 (2012).
Passoni, et al., "ALK as a novel lymphoma-associated tumor antigen: identification of 2 HLA-A2.1-restricted CD8+ T-cell epitopes", Blood, 99:2100-6 (2002).
Perani, et al., "The Proto-oncoprotein SYT Interacts with SYT-interacting Protein/Co-activator Activator (SIP/CoAA), a Human Nuclear Receptor Co-activator with Similarity to EWS and TLS/FUS Family of Proteins", J Biol Chem., 280:42863-76 (2005).
Rajasekjar and Begemann, "Concise review: roles of polycomb group proteins in development and disease: a stem cell perspective", Stem Cells, 25:2498-510 (2007).
Radhi, et al., "Selective expression of the Sp17/AKAP4/PTTG1 in NSCLC for detection and therapy.", ASCO Annual Meeting, J. Clin. Oncol. 31 suppl:abstr e18527 (2013).
Saini, et al., "A novel cancer testis antigen, A-kinase anchor protein 4 (AKAP4) is a potential biomarker for breast cancer", PLoS One, 8(2):e57095 (2013).
Shaw, et al., "Clinical features and outcome of patients with non-small-cell lung cancer who harbor EML4-ALK", J. Clinl Oncol.,, 27(26):4247-53 (2014).
Shi, et al., "Chimeric antigen receptor for adoptive immunotherapy of cancer: latest research and future prospects", Mol Cancer, 13:219 (2014).
Skalova, "Mammary Analogue Secretory Carcinoma of Salivary Gland Origin: An Update and Expanded Morphologic and Immunohistochemical Spectrum of Recently Described Entity", Head and Neck Pathology 7:S30-6 (2013).
Somers, et al., "Folate receptor alpha, mesothelin and megakaryocyte potentiating factor as potential serum markers of chronic kidney disease", Biomarker Insights 9:29-37 (2014).
Soulez, et al., "SSX and the synovial-sarcoma-specific chimaeric protein SYT-SSX co-localize with the human Polycomb group complex", Oncogene 18:2739-46 (1999).
Tenzer, et al., "Modeling the MHC class I pathway by combining predictions of proteasomal cleavage, TAP transport and MHC class I binding", Cel Mol Life Sci., 62(9):1025-37 (2005).

(56) References Cited

OTHER PUBLICATIONS

Tognon, et al., "Expression of the ETV6-NTRK3 gene fusion as a primary event in human secretory breast carcinoma", Cancer Cell, 2:367-76 (2002).

Tognon, et al., "The chimeric protein tyrosine kinase ETV6-NTRK3 requires both Ras-Erk1/2 and PI3-kinase-Akt signaling for fibroblast transformation", Cancer Res., 61:8909-16 (2001).

Trautmann, et al., "SS18-SSX fusion protein-induced Wnt/$^2$-catenin signaling is a therapeutic target in synovial sarcoma", Oncogene, 33:5006-16 (2014).

Türeci, et al., "Expression of SSX genes in human tumors", Int J Cancer 77:19-23 (1998).

Türeci, et al., "A novel tumour associated leucine zipper protein targeting to sites of gene transcription and splicing", Ongogene, 21(24):3879-88 (2002).

Viphakone, et al., "Luzp4 defines a new mRNA export pathway in cancer cells", Nucleic Acids Res., 43(4):2353-66 (2015).

Weigiel, et al., "Multiple cellular mechanisms related to cyclin A1 in prostate cancer invasion and metastasis", JNCI, 100(14):1022-36 (2008).

Wen, et al. "High throughput quantitative reverse transcription PCR assays revealing over-expression of cancer testis antigen genes in multiple myeloma stem cell-like side population cells", Br J Haematol., 166:711-9 (2014).

Wilhelm, et al., "Mass-spectrometry-based draft of the human proteome", Nature, 9;509(7502):582-7 (2014).

Roitt, et al., Immunology, Fifth Edition:116 (1998).

AKAP4-NCBI database:1-2 (2006).

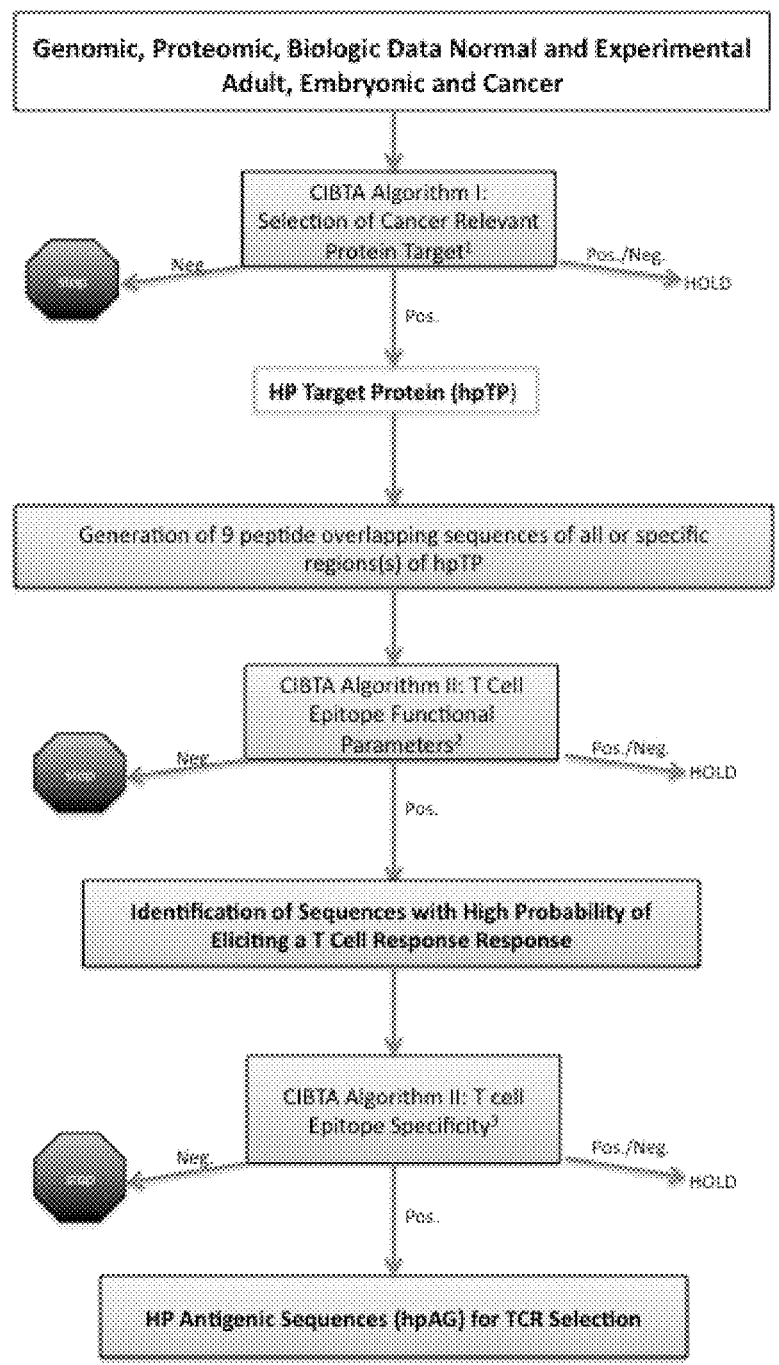

IDENTIFICATION, SELECTION AND USE OF HIGH CURATIVE POTENTIAL T CELL EPITOPES

CROSS REFERENCE TO RELATED APPLICATION

This application is a continuation-in-part of U.S. Ser. No. 14/958,780, which claims benefit of and priority to US Provisional Patent Application No. 62/087,002 filed on Dec. 3, 2014, incorporated by reference in its entirety.

REFERENCE TO SEQUENCE LISTING

The Sequence Listing submitted Dec. 3, 2015 as a text file named "IBT_101_Sequence_Listing.txt", created on Dec. 3, 2015, and having a size of 102,644 bytes is hereby incorporated by reference pursuant to 37 C.F.R. § 1.52 (e)(5).

FIELD OF THE INVENTION

The invention is generally directed to methods for identifying T-cell epitopes with high curative potential, high potency and high probability of T cell recognition, the T-cell epitopes and their use.

BACKGROUND OF THE INVENTION

Targeted antibody technologies have advanced the treatment of cancer. For example, cancer immunotherapies involving antibody-drug targets have improved targeted cancer cell killing. Cancer vaccines used to engender a targeted T cell response have met with more limited success. In all cases, the therapies are rarely curative. At least some of the modest efficacy can be attributed to lack of highly effective targets.

Adoptive Cell Transfer (ACT) is one of the most potent approaches to cancer immunotherapy due to its direct enhancement of T cell killing. Recently, the curative potential of ACT has been demonstrated clinically in leukemia and melanoma. Tumor infiltrating lymphocytes (TIL) (a source of tumor-reactive T cells) have been harvested for ACT, expanded and transferred back to patients to increase the number of tumor-reactive T cells. The antigens TIL recognize are unidentified, but presumed to be tumor related. This approach has achieved durable regression in some patients (about 20% of patients on average), but not in the majority of those treated. The TIL repertoire can be refined by selectively expanding a T cell population using one or more antigens to stimulate specific sub-populations of T cells before transfer.

Ideally, a cancer therapy should eliminate a cancer's regeneration-capable cells (C-RC) to achieve the best possibility for durable regression.

Cancer regeneration leads to relapse, progression, activation of metastases as well as some, but not all, tumor growth. By targeting a protein pivotal to perpetuation of the cancer, the therapy is more likely to eliminate it permanently. Also, failure to eliminate the regenerative component of the cancer can actually activate tumor regeneration leading to rapid growth and progression in large part based on "normal" regenerative mechanisms still active but now usurped by the tumor. Although this facet of cancer biology has not been appreciated as a factor governing the curative potential of cancer immunotherapy, evidence of it is increasing with the clinical use of immune checkpoint inhibitors (Champiat, S. et al. *Clin Cancer Res* 23:1920 (2017)). In some patients an anti-tumor immune response is elicited, but then leads to hyperprogression (Kato, S. et al. *Clin Cancer Res* 23; 4242 (2017)). Although hyperprogression can be explained, if not predicted, by mechanisms of normal epithelial or parenchymal regeneration (Parenteau N L et al. *Current Topics in Developmental Biology* 64:101 (2004)) targeting proteins vital to these mechanisms to achieve a high curative potential has not been obvious. Rather curative potential has been limited by focusing on indirect connections such as: a stromal (Yushalin, et al. British J. Cancer 118:435 (2019)) and immune response similar to wound healing and believed to foster tumor metastasis (Dvorak H F, et al. *Cancer Immunol Res* 3:1 (2015)); resistance arising from both cancer and immune cell plasticity in a wound response manifesting as phenotypic changes in both that lead to regrowth in response to injury and inflammation (Holzel et al. *Nature Reviews Cancer* 13:365 (2013); Chang H Y et al. *Proc Natl Acad Sci* 102:3738 (2005)); evidence of cancer stem cells (CSCs) capable of repopulating a tumor, due to an "unexpected" proliferative response following tumor debulking chemotherapy but where abrogation of chemoresistance is a suggested remedy (Kurtova A V, et al., *Nature* 517:209 (2015)); and detailed genomic analysis on the "non-Darwinian evolution" of a tumor's mutational landscape, which has been suggested as evidence that a cancer should be nearly impossible to eliminate with a single target due to extremely high genetic diversity (Ling et al., *Proc Nat Acad Sci USA.*, 112(47):E6496 (2015))

Deliberate targeting of regeneration as a way of curing cancer has not been obvious to those skilled in the art of cancer biology and immunotherapy (https://www.cancertodaymag.org/Pages/cancer-talk/What-Is-Hyper-Progression-.aspx). Regenerative capability is related to, but mechanistically separable from, response to injury, inflammation, and epithelial-mesenchymal transition that enables metastatic potential. Also, targeting regenerative mechanisms is distinctly different from simply targeting a lineage marker that may be expressed on the surface of a CSC. The preferable way to ensure that a therapy eliminates the regeneration-capable component is through deliberate targeting of a protein important to a tumor's regenerative response—using a modality that kills such as ACT rather than merely inhibits the cells in question, thus preventing time for additional mutations that could overcome the specific challenge.

There remains a need for methods for identifying T cell epitopes that target cells capable of regenerating cancers, and hence have curative potential.

It is therefore an object of the present invention to provide a method for identifying T-cell epitopes which target cells capable of regenerating cancers. It is also an object of the present invention to provide epitopes with a high curative potential, high potency and high probability of T cell recognition.

It is still an object of the present invention to provide methods and systems for programming T cells to selectively attack important tumor cells involved in proliferation, or invasion in an individual.

SUMMARY OF THE INVENTION

A method for identifying T-cell epitopes which target cells capable of regenerating cancers ("C-RCs") is disclosed. The method identifies T-cell epitopes with a high curative potential i.e. durable elimination of the cancer. The high curative potential is afforded by: 1) deliberate targeting a cancer-specific protein that is likely to play a pivotal role in the regeneration of the cancer 2) calculated probability of T cell recognition based on multiple biochemical parameters of antigen interaction that collectively are as good or better than known positive T cell antigens; and 3) a high potency afforded by: a) a requirement that the target cancer protein play an essential role in the perpetuation of the cancer type and stage; and b) stringent specificity of the peptide antigen that allows aggressive treatment with little or no on- or off-target T-cell activation and killing beyond the tumor (HP). The method includes: (i) identifying high curative potential target proteins (HP-TP) i.e., identifying HP-TP; (ii) identifying peptide sequences within the protein sequence of an HP-TP that have a high probability of eliciting T cell killing; and (iii) qualifying the sequence specificity based on the fold difference between the specific target and non-targets that maximizes safety and potency.

The method of step 1, identifies a HP-TP based on: 1) its pattern of cancer expression within and across different forms of cancer, number of patients with advanced diagnoses, and other incidence factors impacting the clinical opportunity (collectively, parameters of Frequency); 2) its ability to discriminate cancer cells from normal cells (Specificity); and 3) the strength of its functional relationship to the cancer's ability to perpetuate itself (Functional Connectivity). These characteristics either contribute or detract from the value of the TP (target protein) as an HP-TP. A TP must have a positive value in all three parameters to move to Step 2.

The Frequency value measures the incidence of the protein's expression within a number of total advanced diagnoses. Also, it considers the protein's expression in multiple types of cancer, a specific type of cancer, and within a shared cancer phenotype from multiple origins. This is not only an indicator of curative potential within the cancer population but is also a positive indicator of functional connectivity as retention in a type of cancer despite increasing mutational burden and metastatic disease indicates that the tumor's biology has become dependent on that protein change for perpetuation. Likewise, the distribution of the change in multiple cancers adds strength to a target's HP value as a strong functional connection to regeneration increases the likelihood of the protein being shared among related cancer types (AKAP4 is an example of such a TP included herein). A TP must have a positive frequency score to proceed to Step 2.

Specificity is valued based on normal expression, the novelty of adult expression based on its being a neoantigen due to mutation or rearrangement, a re-expressed developmental protein, or a protein with novel adult expression, such as certain cancer germline antigens (CGAs), formerly known as cancer testis antigens (CTAs) as their expression is normally confined to the testis. It evaluates normal expression in the adult, embryo, disease states and healing as well as the reason for the abnormal expression like a mutation, rearrangement, or novel adult expression due to a change in methylation status. Normal expression and the extent of this expression will contribute negative values whereas a neoantigen caused by a chromosomal rearrangement expressed only in cancer will contribute a positive value. The overall specificity score of the TP must be positive to continue to Step 2.

Functional Connectivity is valued based on the scientific evidence that is available to connect the protein's function to a function pivotal to the perpetuation of the cancer, where without its expression, the C-RC of the patient's form of cancer is unlikely to have regenerative capacity. Importantly, the method distinguishes the biological priority of target proteins as they relate to the perpetuation of a tumor. For example, although targeting "driver" mutations (a mutation that confers a growth advantage) is considered desirable, some changes considered to be driver mutations will be auxiliary factors to regenerative mechanisms. That is, a protein that better enables a cancer to spread or enables it to grow more rapidly to form the bulk of a tumor may be by definition a "driver mutation" without being pivotal to regeneration and will have a lower impact on curative potential. The method of step one distinguishes the difference, which will be reflected in the Functional Connectivity score.

Also provided are T-cell antigens with a high curative potential, high potency and high probability of T cell recognition as not all parts, if any of a TP will be antigenic. The second step in the process is the determination of T cell epitopes within the HP-TP. This part of the process improves the discovery of potential T cell antigens across major HLA types. It enables a rapid read of a cancer target's potential as a source of antigen for immunotherapy while improving on the epitope selection process.

There are different levels of targetable cancer antigens; cancer antigens that are targetable because they are limited to non-vital organs such as the prostate; Antigens that are present in normal tissues at a low frequency or concentration, but specifically upregulated in cancer, creating the possibility of a differential response that limits the cancer while diminishing the chance of side-effects in normal tissues; antigens that are present only in the germ line (cancer germline antigens (CGAs) formerly termed cancer-testis antigens (CTAs)), which are primarily limited to the testis (which is immune-privileged). Some CGAs may show slight expression in the ovary as well; and antigens that are cancer neoantigens where genetic deletions, rearrangements, or mutation lead to the generation of novel sequence (neoantigens) within the expressed protein.

Epitope specificity is important to the eventual effectiveness of the immunotherapy—impacting its safety and potency. First, it impacts potency as off-target effects are minimized thus allowing for a more aggressive dosing with less side effects. Second, it is more likely to result in a more potent immune response with less down-regulation by T regulatory cells that would normally be activated to protect against auto-immunity of an antigen co-expressed in normal tissues. The more potent, targeted and sensitive the mechanism of the immunotherapy, the more specificity becomes an issue. For example, adoptive immunotherapy employing chimeric antigen receptors (CARs) rely on antibody recognition of cancer antigen thus requiring robust expression of the antigen on the cell surface, estimated to be at least 1,000 molecules. In contrast, adoptive immunotherapy employing TCRs for recognition of an HLA-presented epitope is exquisitely sensitive requiring only a single or few presented epitopes.

Specificity at the protein level is a requirement for an HP-TP and is determined in step one. However, the core nonamer epitopes identified in step two may be present in other non-related proteins. Thus, the third step in the process calculates off-target potential of an epitope; no off-target potential being most preferred for optimal use of TCR-based immunotherapy and to realize its highest curative potential.

The T-cell antigens include a core sequence of nine amino acids homologous to a sequence expressed within a qualified HP-TP; 2) a calculated high probability of T cell recognition and response; 3) a high degree of molecular specificity for the HP-TP or family of HP-TP where the sequence bares little to no homology to peptides of normal adult human proteins in the implied probabilities of observing precise sequence alignment between the intended target and off-target sequences; and 4) a predicted antigenicity comparable to or superior to known, clinically-active T-cell antigens. The nine amino acid sequences are identified based on a linear sequence. However, it is appreciated by those skilled in the art that the antigen is recognized based on consensus, in many cases as a motif, therefore amino acid substitutions that do not cause a configurational change or where a motif is intact are considered equivalent antigens. While nine amino acids is a typical and highly useful length for cleaved amino acid sequences in the context of both HLA and TCR binding, the epitope may be shorter, six, seven or eight amino acids, or part of a longer epitope, typically, ten, eleven or twelve amino acids in length.

The sequence is linear, meaning that it is a contiguous sequence within a protein of several hundred to several thousand amino acids, really no limit. The sequence does have conformational elements and sidechain charge elements that allow highly specific and accurate binding to both HLA and TCR sequences, ultimately allowing efficient binding and activation.

Also provided is a method for reprograming T cells to selectively attack tumor cells capable of perpetuating a tumor. The method includes engineering the T cells with TCR receptors that recognize the epitopes disclosed herein.

A method for treating a cancer patient that includes reinfusing T cells modified to recognize the epitopes disclosed herein are also provided.

BRIEF DESCRIPTION OF THE DRAWINGS

FIG. 1 is a schematic showing the steps for identifying HP-Ag sequences. 1, High curative potential, high potency, high probability filter; link established to regeneration/perpetuation of cancer population. Curative input+Algorithm I; 2, Manually combine algorithm data with or without computational Algorithm II of T-cell Epitope functional Parameters (Multiple HLA Class I types); 3, Manually computed for specificity using Basic Local Alignment Search tool.

DETAILED DESCRIPTION OF THE INVENTION

I. Definitions

Highly curative ("HC") refers to a therapy that achieves permanent regression of a cancer in a majority of patients treated.

"ACT" is used herein interchangeably to mean "Adoptive Cell Therapy" or "Adoptive Cell Transfer", and refers to the transfer of T cells reactive to a patient's disease state, for example, cancer back into the patient. The T cells are preferably obtained from the patient.

The term "cancer's regeneration-capable cells" (C-RC) as used herein refers those cells within a tumor capable of perpetuating the tumor due to pivotal changes that misappropriate or abnormally maintain mechanisms of progenitor activation, renewal, or response.

"HP-ACT" as used herein refers to high curative potential Adoptive Cell Transfer.

"HP-TP" is used herein to mean HP target protein and it refers to protein targets expressed in a cancer, shared by individuals, that are specific for and pivotal/essential to the perpetuation/regeneration of the cancer.

"HP-Ag" as used herein refers to antigens expressed within an HP-TP that have a high probability of T cell recognition and a sequence specificity that enables an on-target potency not limited by on- and/or off-target toxicity.

The term "high probability" refers to a probability of eliciting a T cell response as good or better than known positive T cell antigens.

The term "high potency" refers to an antigen that can be used clinically in ways that maximize its potency with little or no on- or off-target toxicity to vital tissues.

The term "treatment" refers to the medical management of a patient with the intent to cure, ameliorate, stabilize, or prevent one or more symptoms of a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "tumor" refers to an abnormal mass of tissue containing neoplastic cells. Neoplasms and tumors may be benign, premalignant, or malignant.

The term "cancer" refers to a population of abnormal cells that displays uncontrolled growth, invasion upon adjacent tissues, and often metastasis to other locations of the body. The cancer can arise from different organs and types of tissue and can be a sarcoma, lymphoma, leukemia, carcinoma, blastoma, or germ cell tumor. The cancer can be an epithelial cancer (carcinoma) involving the parenchyma (functional tissue) of a vital organ, such as the mammary gland of the breast, the exocrine or endocrine glands and ducts of the pancreas, hepatocytes of the liver, alveoli of the lung and the lining of the gut.

II. Antigens with a High Curative Potential, High Potency and High Probability of T Cell Recognition (HP-Ag)

Peptide sequences homologous to sequences within HP target protein, having a high curative potential, high potency and high probability of T cell recognition have been identified. These are referred to as HP-Ag, having a combination of properties that enable the design and production of medically and commercially feasible HP-ACT. These include:

1) a core sequence of nine amino acids homologous to a sequence expressed within a qualified HP-TP. While the exercise can be done for all length variants, 9mer is the most common derivation of antigenic sequence. The nine amino acid sequences are identified based on a linear sequence. However, it is appreciated by those skilled in the art that the antigen is recognized based on consensus, in many cases as a motif, therefore amino acid substitutions that do not cause a configurational change or where a motif is intact are considered equivalent antigens. While nine amino acids is a typical and highly useful length for cleaved amino acid sequences in the context of both HLA and TCR binding, the sequence may be shorter, six, seven or eight amino acids, or part of a longer epitope, typically, ten, eleven or twelve amino acids in length.

The method identifies the core but the antigen binding characteristic can be tweaked with the addition of additional sequence (usually one amino acid to the end where the peptide binds the MHC).

2) a calculated high probability of T cell recognition and response determined using calculated values for predicted peptide chemistry, probability of effective HLA presentation including: HLA binding affinity, processing and transport efficiency, as well as binding stability and TCR antigenicity. Multiple values are calculated for key variables such as affinity and stability using available algorithms that employ different methods and datasets. The variables are weighted and the level of corroboration across parameters is determined based on data from known positive and negative T cell antigens.

3) a high degree of molecular specificity for the HP-TP or family of HP-TP and little to no homology to peptides of normal adult human proteins calculated as the fold difference between specific target and non-targets. Accordingly, the peptide sequences have a high probability of distinguishing normal cells from cancer cells.

HP-TP

A protein which qualifies as a HP-TP has at least the following characteristics:

1) its expression is linked to a function and/or pathway necessary for a type or stage of cancer to regenerate/perpetuate itself;

2) it is expressed in a population or subpopulation of one or more types of cancer; and 3) It is selectively expressed in such a way as to enable complete killing of expressing cells within the cancer while avoiding normal cells of vital organs.

The peptides are synthesized from in silico-qualified HP-Ag sequences and used as tools for HP-ACT design and development.

Potential targets for T cell therapy development, including HP-TP, can come from several sources such as viral epitopes, neoantigens caused by mutation or chromosomal rearrangements, re-expressed developmental proteins, proteins from immune-privileged tissues such as the testis, differentiation antigens limited to non-vital cells or tissues, fusion regions of hybrid proteins, in particular, shared regions in a fusion protein family, or epigenetically neo-expressed or re-expressed proteins such as cancer germline antigens (CGA) previously termed cancer testis antigens (CTA) linked to enabling function.

CGA (CTA) are recognized as promising targets for cancer immunotherapy because their normal expression is either strictly confined to, or selectively expressed in, the testis (Hoffman et al. *Proc. Natl. Acad. Sci.* 105(51):20422-20427 (2008)). However, CGA, which are normally associated with spermatogenesis in development and/or the adult, cover a broad range of proteins that differ in their function. These differing functions, if any, within the cancer will impact its curative potential. Some are discounted as HP-TP based on specificity and others, although high in specificity, will be discounted because of their lack of functional connection to cancer regeneration. Expression of a CGA in a cancer because of a change in methylation status for example is insufficient alone to qualify it as an HP-TP and source for HP-Ag of the methods disclosed herein. However, some CGAs do have an established functional connection to drivers of tumor regeneration, either as an important upstream component, or as an integral part of the growth cascade. In addition, certain cancer proteins, including some CGAs, will be linked indirectly to regeneration and be clinically important due to an enabling auxiliary function. For example, auxiliary target proteins (Aux-TP) may support progression of the cancer by enabling the tumor cells to metastasize. However, in all cases, both HP-TP and Aux-TP must meet requirements for expression and specificity in step one their only difference being either a direct (HP-TP) or indirect (Aux-TP) role in a cancer's regeneration.

Auxiliary Target Protein (Aux-TP)

The second or auxiliary target protein (aux-TP) has the most characteristics of an HP-TP including frequency and specificity. A functional connection to cancer regeneration and progression is enabling but not directly causative. Characteristics of Aux-TP peptides include:

1) A peptide comprising or containing a core peptide sequence of 9 amino acids homologous to a sequence expressed within a qualified Aux-TP, where the Aux-TP is:
   a. Linked to a function and/or pathway that supports the growth, metastasis or survival of tumor cells,
   b. Expressed in a population or subpopulation of one or more types of cancer,
   c. Selectively expressed in such a way as to enable complete killing of expressing cells within the cancer while avoiding normal cells of vital organs
2) Peptide sequences with a calculated high probability of T cell recognition and response determined using an integrated comprehensive algorithm or a curated combination of algorithms; and
3) Peptide sequences that have a high degree of molecular specificity for the Aux-TP or a family of Aux-TP and little to no homology to peptides of normal adult human proteins calculated as a fold difference between the specific target and non-targets.

III. Method of Identifying HP-Ag

Tumor-related T cell epitopes have been identified by screening tumor proteins, cDNA library cloning methods, and use of an algorithm alone or in combination to predict reactive sequences within either differentially expressed cancer proteins or neoantigens caused by a virus, mutation or translocation. Many studies have focused on the development of better diagnostics and cancer vaccines thus the need for molecular specificity or a functional connection to cancer regeneration, two requirements for an HP-Ag, have not been considered.

It is recognized that, in theory, potential targets for T cell therapy development, including HP-TP, can come from several sources such as viral epitopes, neoantigens caused by mutation or chromosomal rearrangements, re-expressed developmental proteins, proteins from immune-privileged tissues such as the testis, and differentiation antigens limited to non-vital cells or tissues. However, in spite of this general awareness, efforts have yielded few if any T-cell antigens, identified or proposed, as potential T-cell antigens for immunotherapy. Where enough information is presently available to evaluate them as potential HP-TP, most fail HP-TP criteria in a standardized assessment of HP-TP value using Algorithm I.

Methods of T-cell target identification employed to date have failed to discover T-cell targets and epitopes that can meet the criteria disclosed herein and thus be useful in the development of HP-ACT or other next-generation immunotherapies. This is likely due to 1) a failure to first identify targets linked to cancer regeneration, i.e., HP-TP, and 2) the methods used to distinguish and value potential T cell epitopes.

Empirical methods are laborious, costly, and importantly, have fallen short in their ability to find clinically-relevant Class I epitopes. As well, in silico methods have performed poorly as predictive tools. These deficiencies have become clearer as bench, pre-clinical and clinical data on the relationships between epitope chemistry and subsequent T cell response advances (Chowell, et al. *Proc Natl Acad Sci* 112:E1754; Lanzarotti, Mol Immunol 94:91 (2018)). It is increasingly evident that peptide antigen affinity to HLA, once thought to be the defining step in epitope prediction, is inadequate and the clinical relevance of previously established limits questionable.

The methods and compositions disclosed herein are based on studies to determine better predictive limits of each parameter—ultimately resulting in a pattern that is more likely to predict amino acid sequences that will be processed, bind certain HLA molecules, and result in T cell killing in vivo. Thus, the methods combine multiple measurements and methods of calculation across a broad range of parameters gathered from a variety of curated database algorithms (resources)—established using data from both viral and non-viral epitopes. Although the idea of combining multiple resources (for example, Calis J J A *Immunogenetics* 67:85 (2015); Doytchinova I A et al. *BMC Bioinformatics* 7:131 (2016)) and the use of machine learning (reviewed by Luo H et al. Bioinformatics and Biology Insights S3:21 (2015)) are known to be ways to improve predictive accuracy, to our knowledge, prior to this invention, others had not combined resource data with the purpose of using curated analysis and machine learning on the combination to form a new selection process with new parameter limits, resulting in a method that achieves markedly improved predictive performance.

Ultimately, the selection of HP-TP and the subsequent isolation of HP-Ag sequences capable of delivering effective, specific, and sustained interactions between engineered T cells and the C-RC requires a multi-faceted screening mechanism with the deliberate intent of enabling high curative potential. The screening acts as both a discovery tool and effective screening mechanism in a staged procession ejecting candidates with characteristics inconsistent with HP-TP, high probability of T-cell response and low on-target or off-target side effects (FIG. 1). It allows the systematic and rapid exclusion of large amounts of data to rapidly identify HP-TP as information becomes available. More specifically, identification of an HP-TP involves the valuation of three major parameters: Frequency and pattern of expression in types of cancer, the Specificity of the Protein expression compared to normal tissues and the Functional connection of the protein's function or involvement in a pathway that allows one to determine whether the protein is pivotal to the regenerative function and survival of the cancer. A positive or negative value for each major parameter is the sum of multiple characteristics that are numerically weighted based on how much the characteristic adds positive value or negative value to the protein functioning as an HP-TP.

More specifically, Frequency values are calculated based on whether the TP is expressed in multiple cancers, a specific type of cancer of single origin, or a shared phenotype arising from multiple origins. Then the TP is graded within the category based on the frequency of expression and the number of advanced diagnoses for the cancer target(s). A TP must have a positive frequency score to proceed to Step 2.

Specificity is valued based on normal expression, the novelty of adult expression based on its being a neoantigen due to mutation or rearrangement, a re-expressed developmental protein, or a protein with novel adult expression, such as certain cancer testis antigens normally confined to the testis. Normal expression and the extent of this expression will contribute negative values whereas a neoantigen caused by a chromosomal rearrangement expressed only in cancer will contribute a positive value. The overall specificity score of the TP must be positive to continue to Step 2.

Functional Connectivity is valued based on the degree of scientific evidence that is available to connect the protein's function to a function pivotal to the perpetuation of the cancer, where without its expression, the cancer cell is unlikely to have regenerative capacity. Science that specifically demonstrates that the protein is involved in developmental processes or other stem cell biology adds positive value. TP involved in pathways that are enabling (like assisting migration) but not pivotal to the survival and perpetuation of the cancer, are not assigned any positive value for this parameter. A TP must have a positive functional connectivity value to qualify as an HP-TP. However, TP determined to be involved in a non-pivotal, i.e., auxiliary function can proceed to Step 2 as an Aux-TP if the TP has positive Frequency and Specificity values. Candidate TP that have insufficient scientific information to score its functional connectivity are put on hold awaiting additional information.

Science that specifically demonstrates that the protein is involved in developmental processes or other stem cell biology adds positive value. TPs involved in pathways that are enabling (like assisting migration for example) but not pivotal to the survival and perpetuation of the cancer, are not assigned any positive value for this parameter. A TP must have a positive functional connectivity value to qualify as an HP-TP. However, TP determined to be involved in a non-pivotal, i.e., auxiliary function can proceed to Step 2 as an Aux-TP if the TP has positive Frequency and Specificity values. Candidate TP that have insufficient scientific information to score its functional connectivity are put on hold awaiting additional information. The frequency data may change with the availability of larger cancer data sets representing more diverse patient populations; with additional research, new functional connections may be discovered that can impact the scoring of functional connectivity. However, reasons for lack of specificity are less likely to change provided the data is accurate.

Although the safety issues that arise due to lack of specificity may be abrogated by the incorporation of molecular "brakes" that can stop an adverse T cell reaction (for example, Budde et al. *PLoS ONE* 8(12): e82742 (2013)), such safety measures are unlikely to increase the curative potential of the therapy. Likewise, the addition of complementary treatments like the use of checkpoint inhibitors in conjunction with the ACT therapy to broaden the immune response to tumor antigens are unlikely to overcome major targeting weakness or the significantly reduce the variability of response in the majority of patients, similar to the TIL limitations, while adding the possibility of additional side effects.

Scores for some cancer targets that have been tested clinically in ACT, were compared against some TP candidates using the step one process (shown in the Table below) illustrates that protein expression (measured in Frequency) has been the primary basis for ACT target selection. Not all promising TP candidates will pass the three criteria of an HP-TP.

| Target Protein | Basis for evaluation | Frequency | Specificity | Functional Connectivity | Qualifies as an HP-TP? |
|---|---|---|---|---|---|
| Mesothelin | Clinical ACT Target | 18 | −19 | −4 | No |
| Folate Receptor Alpha | Clinical ACT Target | 14 | −24 | 3 | No |
| PSCA | Clinical ACT Target | 14 | −24 | −4 | No |
| gp100 | Clinical ACT Target | 16 | −15 | −4 | No |
| MAGE A3 | CGA/Clinical ACT target | 14 | −4 | −1 | No |
| NY-ESO-1 | CGA/Clinical ACT target | 7 | 0 | 0 | No |
| WT-1 | Clinical ACT Target | 18 | −24 | 11 | No |
| EGFRVIII | Clinical ACT Target | 7 | 0 | 0 | No |
| ROR1 | Clinical ACT Target | 18 | −16 | 8 | No |
| L1CAM | Clinical ACT Target | 14 | −31 | 8 | No |
| SSX | Clinical ACT Target | 14 | −13 | 6 | No |
| BRD4-NUT | CGA (NUT)/HP-TP candidate | 9 | 10 | 4 | Yes |
| AKAP4 | CGA/HP-TP candidate | 14 | 4 | 6 | Yes |
| TMPRSS2-ERG | HP-TP candidate | 13 | 12 | 4 | Yes |
| BORIS (CTCFL) | CGA/HP-TP candidate | 18 | −9 | 3 | No |
| ALK fusion | HP-TP candidate | 4 | 6 | 4 | Yes |
| LUZP4 (HOMTES 85) | CGA/HP-TP candidate | 7 | 6 | 4 | Yes |
| ETV6-NKRT3 | HP-TP candidate | 4 | 6 | 4 | Yes |
| LY6K | HP-TP candidate | 20 | 6 | −4 | No as HP-TP; Yes as Aux-TP |

The three-category method selects for curative potential through the scoring of strengths and weaknesses across diverse types of target proteins. A mandated series of parameters is researched and scored to avoid false assumptions (such as the biological priority of a driver mutation) that have limited one from achieving maximum curative potential in the past.

Alternatively, the selection may be done without numerical weighting of characteristics by constructing a scientific argument and conclusion by combining curated literature searches and data mining. Sequence analysis to identify HP-Ag is determined based on calculated values for predicted peptide chemistry, probability of effective HLA presentation including: HLA binding affinity, processing and transport efficiency, as well as binding stability and TCR antigenicity. Multiple values are calculated for key variables such as affinity and stability using available algorithms that employ different methods and datasets derived from a combination of broadly available algorithms at BIMAS (Bioinformatics and Molecular Analysis Section, NIH), SYFPEITHI, and/or Net MHC pathway (described in Tenzer, et al., *Cell Mol. Life Sci.* 62(9):1025-1037 (2005)) among others where multiple parameters are valued. The parameters are weighted and the level of corroboration across parameters is determined based on data from known positive and negative T cell antigens).

An exemplary method for identifying HP-TP and related HP-Ag is diagramed in FIG. 1. In general, the method includes three steps: identifying target proteins as HP-TP; performing an epitope evaluation; and screening of the HP-Ag specificity and off-target potential.

A. Step 1: Identifying HP-TPs

This first step utilizes a combination of known potential target data from basic and clinical research as well as specific proteomic data generated from specialized culture, manipulation and proteomic analysis of tumor-derived C-RC. HP-TPs are identified through (i) focused, curated literature and database searches as well as (ii) primary experimental data using C-RC stimulated to grow in vitro from human tumor samples. This primary data may include the derivation of subtractive proteomic profiles of CR-C against the tumor bulk as well as normal tissues and experimentally-derived normal regenerative cells. Candidate proteins are further selected from the differentially expressed proteins identified through literature data and/or laboratory data.

In one embodiment, a protein is identified for its target potential based on (i) the parameters that determine whether the target is reachable and practical based on pattern of expression within a type of cancer or across multiple types of cancer, the clinical ability to reasonably identify/screen for the patient population for therapy and clinically test for efficacy, (ii) its ability to discriminate cancer cells from normal cells (Specificity), and (iii) the strength of its functional relationship to the cancer's ability to perpetuate itself (Functional Connectivity).

The first step is the discovery of HP proteins that 1) they are reliably expressed in cancer 2) adult expression is limited to abnormal and non-vital tissue to be safely targeted by T cell therapy and 3) have a biological connection to a cancer's ability to perpetuate itself, or regenerate. The method of step one of the HP process incorporates data from curated text mining (based on the ideas of Swanson (reviewed by Bekhuis T., *Biomedical Digital Libraries* 3:2 doe 10.1186/1742-5581-3-2 (2006)) of the cancer, regenerative medicine and stem cell literature as well as gene expression data. Also, data can come from using in vitro stimulation of regeneration and tumor modeling (U.S. Pat. No. 9,977,025). Step one not only identifies protein candidates but also identifies nexuses within functional networks, where important regenerative functions connect and where certain functions can be rate limiting. This can be done with the help of systems biology methods. The analysis informs one where to look for evidence of a protein's curative potential and can lead to the discovery of additional HP protein candidates. Network analysis can be assisted by systems biology resources such as STRING (Szklarcryk D et al. Nucleic Acids Res. 47:D607-613 (2019)). An example of one such nexus is nuclear transport, where a protein change causes modified mRNA transport leading to changes in gene transcription that result in dysregulation of differentiation and the disruption of cell lineage. For example, LUZ P4 is a CGA protein expressed in some cancers. Being a CGA protein is a quality that in itself might make it a therapeutic target, but information that LUZP4 impacts nuclear transport in cancer (Viphakone N et al., Nucleic Acids Research 43:2353 (2015)) makes it a potential HP target protein (HP-TP); both properties are necessary for high curative potential.

Although expression is the most obvious quality of a cancer target, alone, it is not enough to determine a target's curative potential. Therefore, a way to reliably compare candidates that factors in its functional connection to curative potential is needed. First, to ensure that the therapy is being deliberately designed for curative potential and second, to ensure that the negative clinical impact fostered by missing the regeneration-capable component is avoided.

Assessment at step one provides some practical assurance that the therapy developed based on the HP-TP will have adequate commercial value to be able to ultimately reach the patients that need the therapy. The method also evaluates antigen type and expression patterning as a related but separate category, further refining the analysis and selection of high value targets. Preferably, the information associated with the potential target proteins is screened using the method of Step 1 that assigns positive and negative numerical values to the multi-variate set of weighted parameters, either adding to or subtracting from the curative value of the HP-TP. To qualify as an HP-TP, the TP must have a positive frequency value, positive specificity, and positive confirmed or probable functional connectivity based on known science and/or laboratory data. To qualify as an Aux-TP, the TP must have a positive frequency value, and positive specificity but does not require positive functional connectivity.

This screen establishes the protein target as either an HP-TP or Aux-TP and assigns a target value of the candidates in the initial pool for further prioritization.

(1) Frequency

Data is screened for expression profiles consistent with a shared expression amongst a definable group of patients. Measure of commercial feasibility and value is an additional outcome and benefit of this step. In some embodiments, a protein's frequency within a cancer type and/or expression in multiple cancers is sufficient to positively value the protein target frequency. A definable population refers to a patient population that can be defined based on characteristics of their history and/or tumor, for example, a non-small cell lung cancer patient population of never smokers that lack an Epidermal Growth Factor Receptor mutation. Positive scores are assigned based on frequency ranges. Higher frequencies within a population have a higher value. A low frequency of <10% of a definable population is considered rare and given a negative value for its ability to reach that population. Frequency also values the total advanced diagnoses of the cancer(s) per year. The more advanced diagnoses, the higher the added value. When the protein is expressed in more than one type of cancer, the % expression and number of advanced diagnoses are additive. The maximum score is achieved for any target expressed in >60% of the definable population with total advanced diagnoses of >100,000/yr. Since HP-ACT is likely to be a curative therapy, even low frequency scores have positive value. It is anticipated that as the experience in HP-ACT develops and methods of screening improve, reaching patients with rarer mutations will become increasingly feasible therefore although a high frequency value is more practical and allows prioritization during the critical period of HP-ACT therapeutic development, less frequent abnormalities might be feasibly reached as well.

(ii) Specificity

Data is screened to determine the specificity of the target protein and in some embodiments additionally, expression profiles consistent with potential efficacy. In one embodiment, expression of the protein is compared between normal cells, non-cancerous but diseased cells (i.e., cells from other disease states), and cancerous cells. Expression shared with normal and non-cancerous diseased cells severely limits the feasible potency of the ACT using an antigen from the target protein, due to increased risk of collateral damage. The nature of HP-ACT therapy requires a very stringent specificity to avoid serious collateral damage to normal tissue. To pass specificity, expression of the candidate HP-TP must be limited to abnormal cells, normal tissues that non-vital or are sufficiently immune-privileged able to be managed to protect them from T cell activity. The following are examples. A low level of expression in normal tissue disqualifies the TP even though the expression may be much higher in the cancer. Ideally, the TP is only expressed in the abnormal cancer cells of the adult or postnatal child. However, a protein expressed in a cancer and also in the normal testis would still qualify because the testis is both non-vital and immune-privileged. A protein expressed in the cancer, the testis and the rods of the retina would qualify because the retina also has some degree of immune privilege and the eye can be protected through local delivery of immunosuppressive drugs, without risk to the rest of the body. A protein that is expressed in cancer, the testis and the glial cells of the brain would not qualify because of the possibility of serious injury to the brain.

(iii) Functional Connectivity

Data is screened for specific involvement in pathways or mechanisms enabling perpetuation of the tumor. A driver mutation will give a cancer a growth advantage over other tumor cells. Within this group, there will be driver mutations that are essential and ones that are non-essential but beneficial to tumor growth and maintenance like some epigenetic changes caused by the primary mutation. Functional connectivity requires that the protein be an essential or pivotal change, capable of directly or indirectly maintaining survival and growth capacity of the cells—where conversely, lack of expression will end the cancer cell's growth and regenerative capacity. Ideally, the change is associated with the progenitor phenotype through the prolongation or promotion of an undifferentiated state or block of differentiation through perturbation of genes associated with regeneration and differentiation such as Myc, Wnt, BCatenin, Notch, Sox2, Hedgehog, p21 etc. For example, a chromosomal rearrangement that causes constitutive expression of anaplastic lymphoma kinase (ALK) results in abnormal tyrosine kinase activity abnormally affecting several major signaling pathways involved in cell cycle progression, differentiation, and survival including Ras, PLCgamma, and JNK among others (reviewed by Chiarle et al. *Nature Reviews Cancer* 8:11-23 (2008)), normally controlled by other kinases and features consistent with a regeneration-capable phenotype. ALK signaling alone can cause transformation further supporting its pivotal nature (Chiarle et al. *Nature Reviews Cancer* 8:11-23 (2008)). A second example is a translocation that causes constitutive activation of a BET bromodomain. BET bromodomains are regulatory factors for c-Myc (Delmore et al. *Cell* 146:904-917 (2011)). MYC has been called the master regulator of cell proliferation and is involved in coordinated upregulation of many features important for regenerative capability: cell division, metabolic adaptation, and survival Delmore et al. *Cell* 146:904-917 (2011). Therefore, an abnormally active BET bromodomain will drive regenerative capability through MYC. Targeting the translocated bromodomain will therefore target the regeneration-capable cells because of its functional connectivity to MYC. A third example is the novel expression of an upstream regulatory protein such as an AKAP that now causes disregulation of a pivotal kinase, protein kinase A (PKA). PKAs balance growth and differentiation through differential cAMP signaling (Neary et al. *Oncogene* 23:8847-8856 (2004)). This differential effect is also seen in cancers (reviewed by Caretta et al. *Cancers* 3:913-926 (2011)). Therefore abnormal neoexpression of AKAP4 (A-kinase anchoring protein 4), a protein capable of binding and directing PKAs and normally only expressed in the testis, has the potential to disrupt the PKA balance and thus the balance of growth and differentiation, an essential aspect of organogenesis, regeneration and thus tumor formation. A protein capable of disrupting PKA towards an inhibition of differentiation will have a functional connectivity to a cell's regenerative capability. In these three examples, each is a protein pivotal to the perpetuation of the cancer although through different means. However in each case, this connection gives the TP a functional connectivity to the regeneration-capable cells of the cancer. Cells not expressing these proteins are unlikely to be regeneration capable. A protein may also establish functional connectivity through other known associations with development, embryonic stem cell renewal or natural and induced pluripotency.

B. Step 2: Epitope Evaluation

In this step, target proteins are broken down into overlapping immunogenic peptides to ascertain the breadth of the potential T cell driven immune response. Relevant peptide characteristics evaluated in this step include immunogenicity, chemistry and antigen processing, biochemical binding properties, and the specificity of peptide sequence in terms of potential immune response cross-reactivity. Understanding the full spectrum of peptidic antigen characteristics enables selection of the highest value epitopes taking into consideration how the target protein is recognized at the molecular level by the immune system and how its epitopes are processed, presented, and responded to by effector T cells to obtain true HP TCR epitopes. HP-Ag represent the active output of this multifaceted screening mechanism and are the substantive physical tool used to isolate high quality reactive TCR in the context of various HLA (human leukocyte antigen) types. This serves as the basis for ACT to treat intractable solid tumors specifically and effectively.

Step 2 is a combination of curated analysis and machine learning. Redundant measures spanning different resource platforms are desired. The input used to evaluate overlapping sequences can come from a variety of resources that can include the Immune Epitope Database (IEDB http://www.iedb.org); NetMHC (Reliable prediction of T-cell epitopes using neural networks with novel sequence representations. Nielsen, et al. *Protein Sci.*, (2003) 12:1007-17); Rankpep (Reche P A, et al. *Human Immunology* 63, 701 709 (2002)); SYFPEITHI (Rammensee, H-G et al. *Immunogenetics* 50: 213-219 (1999)); MHCPred (Guan, P. et al., *Appl Bioinformatics* (2006) 5:55) among others (Soria-Guerra, et al. *J Biomed Informatics,* 53:405 (2015)).

The method of Step 2 can evolve. The data inputs will change as one or more data resources become obsolete, are added to, or are otherwise updated and expanded. Not all changes will add predictive value or be of equal weight. Thus, changes in a resource's relationship to the epitope selection process is (re)assessed as needed to determine its impact on predictive value. Likewise, resources that are determined by machine learning and manual analysis to carry little to no predictive weight or show non-informative disagreement with more highly weighted results (corroborated using multiple resources) are eliminated or replaced as new resources become available.

Step 2 parameters include but are not solely limited to:
Binding energy of the peptide to a Class I HLA molecule
Presence of a known motif to a Class I HLA molecule
Similarity to known Class I HLA-binding peptides
Consensus of HLA Class I binding
Calculations that employ different mathematical methods such as Advanced Neural Networks (ANN) or Support Vector Machine (SVM)
The likelihood of proteasomal processing and presentation
Estimations of binding affinity including those based on amino acid sequence as well as amino acid interactions
Ranking of peptides within the target protein
Immunogenicity prediction based on amino acid position within core nonamer sequences The method of Step 2 is first established by the agnostic consolidation of parameters derived from multiple resources. Patterns and potential discrepancies across resource inputs are identified by manual analysis which includes comparison of consolidated results using validated T cell epitopes of HLA A2. Further patterns, limits, relationships and weighting are then developed with the use of machine learning. Training data sets consisting of nonamer sequences classified as positive or negative in relation to T cell epitopes were analyzed using supervised learning techniques. More specifically, the data was first imported from CSV format to a computer algebra system (Mathematica) in order to facilitate this analysis. Second, threshold levels for each variable are determined to provide optimal univariate classification. Third, various combinations of the variables are considered to construct a multivariate classification algorithm based on applying thresholds to the relevant variables. The computerized results are reviewed against the detailed data and curated results. Machine learning establishes new limits for some parameters. New, and in some cases more flexible limits to certain parameters are then incorporated into the curated analysis. Likewise, curation of the computerized results against the detailed data identifies outliers and areas for improvement in the computerized selection. The combination of both curated analysis and machine learning, which includes patterns too complex for ready manual identification and assessment, results in a superior predictive tool (used to identify the epitopes claimed in the invention).

The epitope selection method of Step 2 was tested for accuracy using HLA A2 epitopes from a blind list of validated:
  Positive human T cell epitopes from the Los Alamos database
  Negative human epitopes from Los Alamos and MHCDM 4.0 data

| # of nonamer sequences | # of true positives | # of true negatives | # of test positives | # of test negatives |
|---|---|---|---|---|
| 266 | 43 | 223 | 117 | 149 |

Step 2 Accuracy

| Validated positives identified correctly | Validated negatives identified correctly | False negatives identified by CES | False positives identified by CES |
|---|---|---|---|
| 38/43 (88%) | 144/223 (65%) | 5/43 (12%) | 79/223 (35%) |

It will be recognized by those skilled in the art that as experience increases, the Step 2 method can become entirely computerized although including a curated (re)analysis is preferred when first testing a new data resource or parameter for inclusion in the process. Resources not incorporated into the method of Step 2 can be used to check one or more aspects of the method's performance or to provide additional information on epitopes identified by the method.

C. Step 3. Screen of HP-Ag Specificity and Off-Target Potential

The Basic Local Alignment Search Tool for proteins (BLASTp; https://blast.ncbi.nlm.nih.gov/Blast.cgi) is a publicly available tool that finds regions of similarity between protein sequences. It analyzes alignments against sequence databases and reports the statistical probability of the match (Expect value (E value)). The selected peptide sequences are screened for peptide specificity and off target reactivity potential using a BLASTp screen employing the *Homo sapiens* RefSeq protein database and parameters optimized for short sequence analysis and preference for minimal substitution, compositional adjustments, and residue substitution as specificity for the intended target sequence is of utmost importance. E values returned for both on-target and off-target returned results create a composite value reflecting the fold difference between the average On-target and average Off-target BLASTp generated values. This fold difference value can be considered the overall specificity rating. The greater the specificity rating the more specific the target sequence. The candidate HP-Ag sequences that passed with high specificity and low off-target potential were qualified as HP-Ag. A specificity rating based on a fold difference value greater than 500 gives reasonable implied probability that reactivity against a protein other than the intended target would be unlikely to occur. This evaluative result would then be confirmed in further preclinical studies. This was the first iteration of the Step three method (Step 3.V1) and results are included herein.

However, BLASTp is primarily designed to find alignments to identify unknown sequences, determine the relatedness of genes and proteins, as well as investigate possible functional and evolutionary relationships across species. The output of a BLASTp sequence alignment reports a Max Score (The highest alignment score within the database sequence), Total Score (a measure of the total alignments within a database sequence), E value (the statistical probability of a correct match), % Identity and % Query Coverage. The purpose of BLASTp output is not specifically designed for the evaluation of off-target potential, however BLASTp data can be used to formulate a multi-faceted measure of the off-target potential of amino acid sequences identified in step two. The earlier iteration of the method (Step 3.V1) relied exclusively on E values as a measure of the likelihood that an amino acid sequence identified in step two would be specific for the HP-TP. E values for protein sequences of all related proteins were deemed on-target for the calculation of fold-difference. E values are important to the primary purpose of BLASTp, i.e., finding protein relationships over relatively long sequences. However, the usefulness of the E value for purposes of defining sets of off-target peptides is less meaningful. Therefore, Step 3.V1 was too simplistic, lacked curated examination of target results, and relied only on the E value. We improved on the method (Step 3.V2), which still uses E values as a surrogate measure for the calculation of off-target potential but that now incorporates the Max Score, % Identity and % Query Coverage as well as manual curation of identical sequences. The method now employs a three-tier calculation to more accurately deal with both on- and off-target related proteins and partial sequence alignments.

The first tier, defined by Max Score, identifies exact matches of nonamer sequences to identify both non-related and related proteins that would result in on-target or off-cancer target reactivity. The first tier is a manually curated assessment of 1° specificity. Manual curation allows for the inclusion of different isoforms, different nomenclature, related, targetable cancer specific proteins, and the identification of related non-targetable proteins. This 1° assessment of target specificity identifies the lowest E value for the first tier that is then used as an on-target reference value for subsequent calculation of off-target potential. If a non-cancer-specific protein is identified in the first tier, the reference on-target value is zero. However, if the sequence is part of a cancer-specific/targetable protein, including a CGA, the lowest E value within the first tier is used to calculate fold difference.

The second tier is defined by the sequence coverage within a protein allowing for amino acid substitutions, additions or subtractions. The lowest E-value within the second tier is used as a surrogate to calculate the fold difference between tier one and tier two as a measure the off-target potential of variable, but similar sequences. The third tier involves the measure of identical sequence coverage covering a partial sequence. The lowest E-value of the third tier and the amino acid coverage, are used to derive a value for the third tier. The fold-differences between on- and off-target potential of the second and third tiers are calculated using the on-target reference value of the first tier. The lowest fold-difference, and thus most likely measure of off-target reactivity, determines the final potential for off-target response. As in the earlier iteration, a 500-fold difference is used as the cut-off for the minimal difference between on- and off-target potential.

It is known to those skilled in the art that T cell recognition and response to sequence is complex. For example, peptide antigen chemistry and potential cross-reactivity can impact off-target T cell recognition in several ways (Adams J J et al. (2011) Immunity 35:681-693). Thus, further improvements to tier two can include ranking of amino acid differences as to their impact on chemistry, geometry, position, flexibility, and stability affecting not only peptide binding within the HLA cleft but subsequent TCR-peptide-HLA recognition. Also, the potential for off-target effects may be further refined with empirical testing combined with machine learning.

IV. Method of Using HP-Ag

The HP-Ag disclosed herein can be used as in vitro tools to enable the development of cancer immunotherapies targeting cancer regeneration. The use of ACT is severely limited for most solid cancers because of the inability to direct enhanced T cell killing to biologically-relevant tumor markers, i.e., proteins essential to the recurrence of the cancer. These proteins enable the cancer cells to survive and regenerate the cancer. ACT that targets a tumor's C-RC is particularly needed in cancers of vital organs, where complete ablation of a normal, functionally critical cell type is not feasible. ACT is also one of the most promising options for the treatment of late-stage metastatic cancers but most likely only if high probability, high potency, high specificity T-cell antigens can be identified within proteins essential to regenerative capacity. While the use of TIL increases the opportunity for relevant tumor reactivity, its ultimate effectiveness is limited by a lack of directing T cell response to peptide antigens (Ag) with high curative potential, high potency and high probability (collectively denoted as "HP") of T cell antigens (HP-Ag).

Tumor-reactive TIL may be used to discover antigenic tumor protein targets. However, this is laborious and the TIL approach to target discovery has several drawbacks that limit the discovery of HP-Ag. Methods that rely on a patients' immune response to identify T cell epitopes can be highly individualized and can miss many potentially valuable antigens. In many patients the immune response has gone through countless refinements and insults leading to skewed, less than optimal and often ineffective T cell killing. Inherent selection of antigen by an individual's immune system is a major drawback to the development of HP ACT (HP-ACT) because of its bias towards certain antigens within a diverse mutational landscape that may be biochemically preferred by the T cell but not useful for killing the C-RC.

The presence of reactive TILs in patients that have advanced cancer indicates that mere T cell recognition within the tumor is not enough. Aside from supporting the immune response with T cell checkpoint blockade or the use of interleukins, there must be an adequate number of T cells within the tumor or in the circulation. While this is something that ACT can achieve, for it to be an HP-ACT therapy, some of these T cells must respond to at least one peptide antigen that is pivotal to the C-RC phenotype.

Irrespective of the complex and differing mutational landscape in each individual, there are proteins pivotal to perpetuation and the C-RC that are likely to be shared by genetic subtypes of cancer. If one can purposefully target those pivotal proteins involved in key pathways that are needed for the type of cancer to persist and use it an effective modality like ACT, then it creates the opportunity to eliminate the cancer using a single or a minimal number of targets. There are additional practical advantages to targeting a protein responsible for a key oncogenic pathway: it means that expression of the protein is more likely to be one that persists as the tumor progresses and metastasizes. This is evidenced in the expression of at least two HP-TP proteins (AKAP4 and TMPRSS2-ERG) described herein. In addition, if the C-RC driver is lost due to mutation, the likelihood is that those cancer cells will have evolved into something less lethal, if they survive at all. Using ACT as the modality targeted to the C-RC will eliminate the cancer before it has an opportunity to develop resistant/alternative clones. Therefore, the combination of a C-RC target and the TCR-based modality deliver the therapy's high curative potential.

Methods used to discover epitopes as presented in antigen presenting cells (APC), such as dendritic cells, fail to fully consider the connective steps required to move an immune response from APC and antigen digest to presentation and activation of effector T cells. In many patients these steps are flooded with irregularities from previous treatments and immune regulators leading to a lower probability of epitope effectiveness. These methods do not evaluate the value of the protein associated with the target up front leading to a large amount of work for data that may be of low curative value. Solely genomic methodologies do not necessarily capture the exome and may be limited by pre- and post-transcriptional regulation, making epitope evaluation of little translatable value without substantial further investigation. Strictly screening stem cell exomes, either genomic or proteomic, limits targets to normal developmental or proliferative antigens and may miss mutation-, translocation-derived or novel expressed antigens. Moreover, most proliferative or metabolic antigens are likely conserved and in use in normal tissue turnover.

Genomic screens with limited additional expression patterning analysis can lead to simple overexpression candidates. This is exemplified by the studies of Ochsenreither, et al. (Ochsenreither, et al. *Blood* 119(23):5492-5501 (2012)) where, after a large effort, Cyclin-A1 presented as a viable target, yet, the normal expression pattern of Cyclin-A1 makes it a poor target, highly susceptible to off-target responses or possibly normal immune regulatory diminution of the response. Multiplatform analyses based on primarily genomic (Hoadley, et al. *Cell* 158(4):929-944 (2014)) data have been performed with relatively predictable results uncovering genetic mutations and amplifications clustered in well-known pathways such as p53 and PI3kinase within the subtypes these categorize. There remains a need for methods for identifying T The methods disclosed herein avoid deficiencies experienced using other methods of epitope identification. An HP target protein (HP-TP) is established and its associated HP-Ag sequences are identified beforehand, then TIL as well as donor PBMC (peripheral blood mononuclear cells) serve as a source of reactive T cells for T cell receptor (TCR) isolation and cloning for HP-ACT development.

Development of HP-ACT against solid tumors involves:
1. The identification of high curative potential tumor protein targets (HP-TP) that are integral/pivotal to the ability of that cancer to regenerate, i.e., perpetuate itself.
2. The identification of peptide sequences within the protein sequence of an HP-TP that have a high probability of eliciting T cell killing (HP-Ag sequence).
3. Qualification of the sequence specificity based on the fold difference between the specific target and non-targets.

One benefit to directing ACT to peptide sequences associated with cancer regeneration is that HP-TP are more apt to be common drivers in a regenerative cancer phenotype and thus shared by individuals with a certain type of cancer and, in some cases, even across multiple types of cancer.

HP-Ag peptides can be used singly or in combination in a variety of methods known to those skilled in the art to select and expand native cytotoxic T lymphocytes (CTLs) that respond to HP-TP (HP-CTL) from patients and donors, or alternatively, to select and clone native TCRs, for the design of TCR vectors and the engineering of HP-CTLs for use in HP-ACT.

The result of the three-step process are sets of HP epitopes that can be used for the selection of reactive T cells and the cloning of TCRs for use in high curative potential immunotherapy. The peptides are preferably used in conjunction with HLA multimers using methods known to those skilled in the art. The method of the invention identifies the sequence of an HP-Ag as well as the HLA type(s) that are likely to present the peptide in vivo. These data are then used to manufacture the HP-Ag:HLA complexes that will capture T cells and their high curative potential TCRs in vitro. Many of the clinically-relevant TCRs to HP-Ag will lie in the moderately high to low affinity range (the physiological range estimated to be between a $K_D$ of 100 to 1 (Hebeisen et al. 2015 Front. Immunol. 6:582)). Therefore, to realize the high curative potential of the adoptive immunotherapy requires isolation of the best functional TCR matches within a range of functional avidities.

Although useful for assessment of T cell response, functional in vitro assays used as a principle screening method for TCRs are dependent on cell response. Due in part to the transient, variable state of the cells, the assay can miss about 50% of TCRs that would be capable of responding to the antigen of interest in vivo (Dolton et al. Front Immunol 2018 9:1378). To capture a more comprehensive sample of T cells that recognize the HP-Ag of interest, screening is done in vitro using the HP-Ag:HLA complexes optimized to achieve the sensitivity needed to isolate physiologically high to low affinity and avidity TCRs.

The pairing of HP-Ag and the type of HLA Class I HLA heavy chain is determined by, and unique to the invention (for example, the AKAP4 epitope MLKRLVSAL will be complexed with either HLA-A2, B8 or B15, and DMSNIV-LML with HLA-A2 only). HLA Class I heavy chains are synthesized and then folded with the HLA light chain (beta-2 microglobulin) and synthesized HP-Ag to form HP-Ag:HLA (Method summarized by Horlock, Experimental techniques, British Society for Immunology, https://www.immunology.org/public-information/bitesized-immunology/experimental-techniques/production-mhc-class-i-tetramers).

Monomers of HP-AG:HLA are biotinylated and bound together by fluorochrome-linked stepavidin (Ramachandiran et al. J Immunol Methods 2007 319 (1-2) 13-20) to form tetramers of HP-Ag:HLA (HP-Ag:HLA-T). Tetramers can be grouped onto larger aggregates with the addition of dextran. Higher order multimers of hpHLA act as an adjuvant by increasing avidity due to more TCR interactions per molecule (Dolton et al. Front Immunol 2018 9:1378). The methods of tetramer production are known to those skilled in the art and the production of custom tetramers can be efficiently synthesized in the laboratory (Leisner et al. 2008 PLoS One 3(2):e1678) or obtained through custom commercial services.

The sensitivity of a tetramer-based screen is adequate to capture very high to moderately high affinity TCRs (Dolton et al. Front Immunol 2018 9:1378). However, it is less sensitive than cell response-dependent functional assays without steps to further enhance and stabilize detection of TCR binding to HP-Ag:HLA-T. These methods are known to those skilled in the art (Dolton et al. Immunology 2015 146:11-22; Dolton et al. Front Immunol 2018 9:1378).

The T cells are modified by exposure to the protein kinase inhibitor (PKI) such as Dasatinib (Lissina et al. *J Immunol Methods* 2009 340(1): 11-24). Reversible inhibition by PKI acts as an adjuvant by preventing TCR triggering and down-regulation thereby lowering the affinity threshold for HP-Ag:HLA-T-TCR interaction (Dolton et al. *Front Immunol* 2018 9:1378). T cells exposed to Dasatinib will bind HP-Ag:HLA more efficiently producing stronger signal at lower HP-Ag:HLA concentrations (Lissina et al. *J Immunol Methods* 2009 340(1): 11-24). In addition, PKI inhibition decreases HP-Ag:HLA-T-TCR-induced apoptosis, important for the capture of an expandable T cell population.

The binding of TCR to HP-Ag:HLA-T on PKI-treated T cells is improved using a fluorochome-labeled antibody against the fluorochrome of the HP-Ag:HLA-T. This antibody not only increases the fluorochrome signal but acts as a "crosslinking" antibody stabilizing the bound HP-Ag:HLA-T-Ab multimers at the T cell surface (Tungatt et al. *J Immunol* 2015 194(1):463-74).

It also acts as an immunochemical bridge for either a fluorochrome- or a magnetic bead-conjugated anti-fluorochrome antibody. Optimization using a PKI with the "crosslinking" antibody is estimated to increase the capture of TCR 40-fold (Dolton et al. Front Immunol 2018 9:1378) making it the most sensitive method for the capture of anti-HPAg TCRs.

Labeled T cells can be sorted by fluorochome-based sorting or, preferably via the magnetic beads. TCRs can then be cloned from the captured T cells and incorporated into vectors for further testing of the TCRs and selection for use in the genetic modification of patient or donor T cells. Alternatively, patient T cells isolated by optimized HP-AG:HLA-T binding can be expanded and used in autologous adoptive cell transfer.

Significant value can be placed on the ability to isolate antigen targets that lead directly to high value TCRs reactive to those targets, however to do so against multiple expressed targets further increases the chance of curative results. Combining intracellular as well as surface expressed antigen targets can be used to optimize and specifically tailor the treatment to the specific cancer sub-type and stage and minimize disease relapse and/or metastasis.

In a preferred embodiment, the HP-Ag sequences are used as tools to select naturally occurring TCRs for the subsequent design and production of modified or unmodified CTLs for adoptive cell transfer. One or more HP-Ag peptides can be used alone or incorporated into molecular and cellular technologies and systems to selectively expand and adoptively transfer back to the patient large numbers of CTLs that respond to presented HP-Ag epitopes or set of HP-Ag epitopes. HP-Ag peptides can also be incorporated into peptimers or loaded into antigen presenting cells and cell lines to isolate and clone T cell receptors (TCRs). The cDNA from the cloned receptors can then be incorporated into vectors to genetically engineer patient T cells that will now recognize and kill tumor cells expressing the HP-TP. Current vector technologies utilizing lentiviral expression and packaging systems allow for a wide variety of selective and targeted protein expression combinations controlled by separate promoter sequences. This can now be done in such a way that multi-chain proteins such as TCRs along with secondary augmenting or adjuvant proteins can be expressed from a single vector under the guidance of separate control elements allowing optimization of TCR expression. The latter case does not require the patient to have native T cells that respond to the HP-TP of their cancer.

Examples of how the disclosed epitopes may be used in T-cell focused immunotherapies include the use of HP-Ag for selection TCRs for the subsequent development of non-cell-based soluble TCR technologies such as ImmTAC (Immune mobilizing monoclonal TCR (T cell receptors) Against cancer) (Immunocore) or the use of surface-expressed HP-TPs as antigens to design ACT therapies based on the use of chimeric antigen receptors (CAR-ACT) (Reviewed in Shi, et al., *Molecular Cancer,* 13:219 (2014)—both therapies acting at the T cell level. Preferably, the HP-Ag are used in HP-ACT therapies employing cloned native TCRs alone or in combination with co-expressed immunomodulatory cytokines.

The immune system includes two key recognition systems, antibodies, which target cell surface proteins, and T cell receptors, which target HLA-presented peptide antigens potentially derived from virtually any intracellular protein. ImmTACs are HLA-peptide targeting bi-specific biologics which include an engineered T cell receptor based targeting system fused to an anti-CD3 scFv based effector function. ImmTACs function by binding to defined HLA-peptides with extremely high affinity (typically <50 pM), simultaneously decorating the target cell with lower affinity (nM) CD3 specific scFv fragments. Any T cell that comes into direct physical contact with an ImmTAC-decorated cancer cell is automatically redirected to kill the cell, regardless of the T cell's native antigen specificity.

In some cases it is desirable to direct T cell killing to more than one target. At a minimum, one target must be an HP-TP for it to be an HP-ACT therapy. However, it may be desirable to eliminate the entire cancer (all cancerous cells of the tumor) using ACT. While the expansion of tumor T cell killing to other targets, a phenomenon known as antigen spreading, is likely during HP-ACT, it may be desirable to ensure more directed T cell killing to stop metastasis, better ensure the elimination of the bulk of the tumor or rapidly attenuate bulk tumor growth to eliminate the possibility of future changes or mutations in the remaining cells that could render them regeneration-capable. This can be achieved by the inclusion of T cells that respond to an enabling auxiliary function.

It will be evident to those skilled in the art that the use of the HP-TP and/or HP-Ag as described in the present invention need not be limited to HP-ACT and can be used to improve the clinical potential of many types of cancer immunotherapy through improved targeting of a specific T cell response to cancer regeneration.

EXAMPLES

Example 1. Distinguishing High Curative Potential Target Proteins (HP-TP) and Aux-TP from Non-HP-TP and Non-Aux-TP Using Mesothelin as the Example The cell surface protein mesothelin has been identified and developed as a target for ACT. Mesothelin is used to illustrate the difference between simply a "cancer marker" or TP and an HP-TP or Aux-TP and how they are qualified. The process applied in this example is not limited to the protein of the example but is generally applicable to all expressed cancer proteins.

Mesothelin is a cell surface protein highly expressed in mesothelioma, as well as ovarian, pancreatic, and a subset of lung cancers (Somers et al. *Biomarker Insights* 9:29-37 (2014)). It is a cell surface protein that begins as a precursor that is then split into the cell-membrane-associated protein mesothelin and a soluble megakaryocyte potentiation factor (Somers et al. *Biomarker Insights* 9:29-37 (2014)). Experts in the field of cancer immunotherapy consider surface-bound mesothelin a clinically viable candidate for ACT, particularly employing chimeric antigen receptor (CAR) modified T cells because of its surface expression (CAR-ACT requires surface expression of the TP because of its reliance on antibody-based target recognition for the initiation of T cell killing.) The supposition is that mesothelin is targetable by ACT because it is highly expressed in cancer compared to normal mesothelium. However, there are several aspects of mesothelin as a TP for ACT that could discount its value as either a HP-TP or Aux-TP. Testing of the target protein is a necessary first step in determining whether the identification of HP-Ags for HP-ACT development is possible and feasible.

Mesothelin's target potential was analyzed based on the parameters of frequency, pattern of expression, and its clinical and commercial feasibility (Frequency), its ability to discriminate cancer cells from normal cells (Specificity), and the strength of its functional relationship to the cancer's ability to perpetuate itself (Functional Connectivity). To qualify, the TP must have a positive frequency based on the degree the target is shared within a cancer population and the size of the population, specificity, and a high confirmed or probable functional connectivity.

Step 1. Qualification of Mesothelin as an HP-TP or Aux-TP

A. TP Frequency

Mesothelin expression in cancer qualifies it as a potential TP based on frequency of expression in multiple cancers. Mesothelin is a proteolytic cleavage product of a mesothelin precursor which when cleaved gives rise to a secreted megakaryocyte potentiation factor and the GPI-membrane anchored mesothelin, the potential cancer protein target. Mesothelin is elevated in mesothelioma and is currently used in its diagnosis, prognosis and monitoring (Hollevoet et al. *Am. J. Respir. Crit. Care Med.* 181:620-625 (2010); Creaney et al. *Clin. Cancer Res.* 17:1181-1189 (2011)). It is also highly expressed in ovarian cancer (Chang et al. *Proc. Natl. Acad. Sci.* USA 93:136-140 (1996)), pancreatic cancer (Argani et al. *Clin. Cancer Res.* 7:3862-3868 (2001)) and the majority of lung adenocarcinomas (Ho et al. *Clin. Cancer Res.* 13:1571-1575 (2007)). Its frequency within a cancer type and high expression in multiple cancers is sufficient to positively value mesothelin target frequency for ACT.

B. TP Specificity

Mesothelin is expressed at lower levels in normal mesothelium of the peritoneum, pericardium and pleura and possibly the trachea (Chang et al. *Proc. Natl. Acad. Sci.* USA 93:136-140 (1996)). Also, its expression is shown to increase in renal disease (Somers et al. *Biomarker Insights* 9:29-37 (2014)). Expression shared with normal and non-cancerous diseased cells severely limits the feasible potency of the ACT due to risk of collateral damage to the peritoneal lining, pleura and pericardium as well as the kidney. This is particularly important in the cancer treatment as many chemotherapeutics, which the patients may have been treated with prior to ACT therapy are known nephrotoxins, where the compromised kidney will also express elevated levels of mesothelin. Differential expression is not enough to overcome the reduction in value because of a loss of both potential potency and potential on-target collateral damage due to lack of specificity. Importantly, the increased expression in the impaired kidney indicates that mesothelin upregulation may be a more generalized wound-healing-associated response and most likely not limited to just the impaired kidney. This lack of specificity gives mesothelin a strong negative value as a TP for ACT.

C. TP Functional Connectivity

Mesothelin failed specificity alone would be sufficient to disqualify it as either an HP-TP and Aux-TP, however, the analysis of its functional connectivity was performed for purposes of the example. Mesothelin's functional connectivity was measured based on its relationship and significance to normal function, tumor function, and in particular, cancer regeneration. Sufficient information existed to assess its probable connection to cancer regeneration and determine its functional connectivity through analysis of protein function, connection to key developmental (regenerative), cell proliferation and survival pathways. A curated literature search found that mesothelin is functionally linked to aspects of tissue remodeling associated with a wound healing response through its association with elevated levels of MMP 7 and IL6-IL6R. Upregulation of a single MMP is not likely to be an essential driver integral to a cancer's ability to regenerate. Even if expressed in metastatic C-RC, mesothelin's biological role in MMP-7 upregulation is less likely to be constant within the C-RC population of the tumor, particularly if they are not actively undergoing metastasis. Therefore this functional connection added no positive value to mesothelin as an HP-TP target.

An increase in mesothelin expression correlates with a rise in IL6-IL6R expression and its actions through the activity of NFkappaB, a major signaling hub in the wound healing response. This response is not specific to cancer as evidenced by the rise in mesothelin as well as IL6 (Ranganathan et al. *Am. J. Physiol. Renal Physiol.* 304:F1054-F1065 (2013)) in kidney disease and its constitutive baseline expression in mesothelial linings. Mesothelin expression leading to IL6 expression and action is a wound healing phenotype that enables cell attachment, survival and continued growth in an inflammatory environment. Knockout studies in mice have found no observed effect on growth and development. Therefore mesothelin upregulation is likely in response to a pivotal change that will drive the cancer rather than the cause of it. Even though it can lead to an increase in IL6, the cytokine levels can be increased for other reasons. This eliminates its values as an HP-TP and discounts mesothelin's value as a necessary auxiliary function in the cancer.

Mesothelin is reported to bind MUC16 (CA125) (Gubbels et al. *Molecular Cancer* 5:50-64). CA125 is described as an ovarian cancer tumor marker. Mesothelin binding to MUC16 is believed to contribute to the cell-cell adherence of metastatic cells to increase metastatic tumor mass as well as the adherence of ovarian cancer cells to the peritoneum. (Felder et al. *Molecular Cancer* 13:129-143 (2014)). However MUC16 is expressed in normal endometrium, lung and amnion and mesothelia among other tissues (Wang et al. *Differentiation* 76(10):108101092 (2008)). The interaction between mesothelin and MUC16 observed in ovarian cancer is therefore an upregulated normal function, devaluing it as an Aux-TP capable of discriminating the C-RC of a cancer. Differential expression is not sufficient to positively value the target protein.

When all factors are valued for their positive and negative measures of frequency, specificity and functional connectivity, mesothelin passes the frequency measure, fails to qualify based on specificity, and fails functional connectivity (Table 1). Mesothelin would not move forward to evaluation of the protein sequence for high probability HP-Ag sequences (Step 2).

TABLE 1

Step 1 Calculation of Mesothelin's HP-TP potential

| Candidate HP-TP | Frequency | Specificiy | Functional Connectivity | Qualifies as an HP-TP? |
|---|---|---|---|---|
| Mesothelin | 18 | −19 | −4 | No |

This is in sharp contrast to the justification and pursuit of mesothelin as a viable ACT target by several groups. Rather, Step 1 predicts that the mesothelin target will be incapable of generating an HP-ACT therapy.

Example 2. Comparison of HP-Ag Derivation Against an Alternative Method of Target and Epitope Identification for ACT Targeting Cancer Stem Cells Many methods to date have had the intent of improving cancer vaccines rather than ACT therapy so their deficiencies in discrimination of HP-TP and HP-Ag are not surprising. However, some approaches have been designed with the goal of identifying cancer proteins and epitopes for ACT targeting cancer stem cells. One such example is the work of Ochsenreuther et al. (2008) (Ochsenreither, et al. *Blood* 119(23):5492-5501 (2012)) where they describe a protein and epitope discovery approach for ACT therapy to target leukemic stem cells in acute myeloid leukemia. Both the target and HLA A2 9 amino acid (9mer) epitopes identified by Ochsenreuther et al. *Blood* 119(23):5492-5501 (2012) were compared using the stepwise, gated approach and associated analysis disclosed herein. The complete protein sequence was then analyzed using Step 2 of the methods herein to determine whether this approach would have identified similar or different antigenic sequences. The results illustrate the impact of the approach on both practical and scientific terms, the difference in resulting output, as well as the benefits and efficiency of the disclosed methods to identify HP-Ag.

Ochsenreuther et al. (2012) employed microarray expression analysis including more than 100 probe sets of leukemic stem cells, hematopoietic stem cell subpopulations, and peripheral tissues to ultimately identify a single candidate, Cyclin A-1 (CCNA1), the only target found after subsequent RT-PCR. Cyclin A-1 is detected in over 50% of AML patients, is associated with cell proliferation, produces leukemia in mice and is minimally expressed in normal tissues other than the testis. This assessment of the TP led Ochsenreuther et al. (2012) to characterize it as a cancer-testis antigen and more specifically, a leukemia-testis antigen suitable for ACT development. They then pulsed dendritic cells with Cyclin A-1 peptides and used the pulsed cells to stimulate clones of reactive T cells from two normal donors. The method identified 8 immunogenic peptides across at least 3 HLA types. Focusing on HLA A*0201, they noted that their cell-based selection method was able to identify a reactive 11 amino acid sequence (11mer) that was not predicted in their use of three in silico methods (SYFPEITHI, BIMAS, IEDB analysis resource) although the in silico methods did identify a 10mer and 15mer at this location.

For comparison, Cyclin A-1 and its epitopes were screened according to the methods disclosed herein. Cyclin A-1 was first evaluated as an HP-TP based on the parameters of frequency, pattern of expression, and its clinical and commercial feasibility (Frequency), its ability to discriminate cancer cells from normal cells (Specificity), and the strength of its functional relationship to the cancer's ability to perpetuate itself (Functional Connectivity).

Step 1. Qualification of Cyclin A-1 as an HP-TP or Aux-TP

A. Frequency

Expression of the protein in 50% of AML was sufficient to qualify it for frequency. Its expression has also been described in other cancers such as prostate (Weigiel et al. JNCI 100(14):1022-1036 (2008)), breast (Khaja et al. *PLoS ONE* 8(8):e72210 (2013)) and non-small cell lung cancer (Kosacka et al. in vivo 23:519-526 (2009)), which added to its positive frequency.

B. Specificity

Cyclin A-1's presumed specificity was noted by Ochsenreuther et al. (2012) as a compelling characteristic for targeted ACT. However, a curated mining of the literature and other available information found evidence that Cyclin A-1 was not restricted to the normal testis. Cyclin A-1 is expressed at low levels in normal human hematopoietic tissue, which is not surprising given its strong association with leukemia. While this would add to its functional connectivity, specificity is discounted because of it. When Cyclin A-1 was first discovered as new form of Cyclin A (Yang et al. *Cancer Res.* 57:913-920 (1997)). It was reported that Cyclin A-1 mRNA was found by northern blot analysis preferentially in testis but to a lesser extent also in the normal brain. In van der Meer et al. *Reproduction* 127:503-511 (2004) reported its expression at low levels in normal mice in the olfactory bulb, hippocampus and amygdala of the adult brain. More recently, Cyclin A-1 expression has been linked to circadian rhythm and sleep in *Drosophila* (Rogulja et al. *Science* 335(6076):1617-1621 (2012)). In 2001 a study looking at the differential methylation status of the Cyclin A-1 promoter reported that although Cyclin A-1 was predominantly expressed in the testis, modest levels could be detected by RT-PCR in the spleen, prostate, leukocytes, colon and thymus (Müller-Tidow *FEBS Letters* 490:75-78 (2001)). Combined, this data suggests that while Cyclin A-1 is preferentially expressed in the testis, it would not be unexpected to find the protein in other normal tissues, of most concern, in portions of the brain and hematopoietic tissue. This would discount it as an HP-Ag candidate based on inadequate specificity.

C. Functional Connectivity

Cyclin A-1 is associated with meiosis in sperm and linked to regeneration. For example, its expression appears needed for induced pluripotent stem cells to achieve a non-tumorigenic pluripotent state (McLenachan Stem Cells and Development 21(15):2891-2899 (2012)) and Cyclin A-1 is expressed in normal CD34+ hematopoietic stem cells (Yang et al. *Blood* 93:2067-2074 (1999)) that establish a connection to regeneration, at least in the hematopoietic system. It other tissues Cyclin A-1 appears to have different functions that would not be connected to mechanisms of regeneration. There is sufficient knowledge to connect Cyclin A-1 to the C-RC in the case of leukemias.

Cyclin A-1 meets the criteria of an HP-TP in frequency and functional connectivity (when restricted to leukemia). However Cyclin A-1 has insufficient specificity to qualify it as either an HP-TP or Aux-TP because of its expression in the normal brain (with confirmation needed in humans), its potential to interfere with hematopoiesis, which discounts its potential potency, and indication that it can be expressed in other tissue like the colon depending on circumstances. Therefore successful use of Cyclin A-1 would require further information and study in order to qualify it as an HP-TP with a high likelihood that it would not qualify as more is known. Cyclin A-1 would not proceed to Step 2 in the methods disclosed herein. Nevertheless, this example proceeded to Step 2 epitope discovery in order to compare the methods disclosed herein, to the methods of Ochsenreuther et al (2012) for epitope discovery.

These studies focused on HLA A2 epitopes identified by both approaches. Ochsenreuther et al. (2012) identified 4 HLA A2 9mers: YAEEIYQYL (SEQ ID NO:1), AETLYLAVN (SEQ ID NO:2), FLDRFLSCM (SEQ ID NO:3) and ASKYEEIYP (SEQ ID NO:4) as well as one 11mer, SLIAAAAFCLA (SEQ ID NO:5). Using a comprehensive comparative analysis of multiple, corroborative parameters, two of the four 9mers were identified as being high probability T cell epitopes: FLDRFLSCM (SEQ ID NO:3) and sequence YAEEIYQYL (SEQ ID NO:1) by the methods of Step 2. The remaining two 9mers showed a low probability of being strong T cell epitopes based on weak calculated binding affinity, stability (dissociation half-times) as well as predicted antigenicity and chemistry and thus would not qualify as candidate HP-Ag using the methods disclosed herein. It also points to the idea that in vitro selection to identify epitopes may not guarantee robust T cell reactivity.

The use of three well-established algorithms, SYFPEITHI (Rammensee, Bachmann, Stevanovic: *MHC ligands and peptide motifs*. Landes Bioscience 1997 (International distributor—except North America: Springer Verlag GmbH & Co. KG, Tiergartenstr. 17, D-69121 Heidelberg), BIMAS (Parker, K C., M A. Bednarek, and J. E. Coligan. *J. Immunol.* 152:163 (1994).) and IEDB (Tenzer et al. *Cell Mol Life Sci* 62(9):1025-37 (2005)) failed to identify the 11mer, a fact Ochsenreuther et al. (2012) used to support their case for the superiority of biological fishing for the identification T cell antigens. However, the in silico process disclosed herein not only identified a high probability core 9mer sequence within the 11mer peptide (SLIAAAAFCLA (SEQ ID NO:5)): LIAAAAFCL (SEQ ID NO:6), it also identified an additional high probability candidate incorporating a portion of the 11mer sequence: YLPSLIAA (SEQ ID NO:7). This illustrates that the deficiency is not in the use of in silico methods per se but that one needs more comprehensive in silico methods, combined in a corroborative system preferably tested using positive and negative controls.

Step 2 identified additional candidates with properties equal to or superior than those previously found by the investigators. In practice, when the identified core 9 mer sequences are used for selection of T cells, that testing can include the addition of peptides on either end of the 9mer core. Therefore unlike the Ochsenreuther approach, the process disclosed herein has a much higher likelihood of capturing the most robust antigen(s) for T cell selection. Very few 9mers (the most likely to bind well to CD8+ TCRs (Doan et al. *Lippincott's Illustrated Reviews: Immunology Second Edition* Wolters Kluwer Baltimore (2013)) and in particular, A2 epitopes had been identified by the laborious Ochsenreuther process. In contrast, Step 2 of the process disclosed herein identified several additional candidate HP-Ag in HLA A2, increasing the likelihood of yielding antigenic peptides with a high probability of TCR reactivity.

HLA A2 high probability 9mer peptides within Cyclin A-1 were selected from a total of 457 sequences using Step 2. Sequences that were selected both manually and by Algorithm II are shown in Table 2. Ochsenreuther et al. (Ochsenreither, et al. *Blood* 119(23):5492-5501 (2012)) sequences are included in bold.

TABLE 2

9mer peptides within Cyclin A-1 with HLA specificity

| Target | HLA Specificity | Core 9mer sequence | HP Sequence based on the method of Step 2 |
|---|---|---|---|
| Cyclin A-1 | A2 | AIMYPGSFI (SEQ ID NO: 8) | Yes |
| Cyclin A-1 | A2 | YLSWEGPGL (SEQ ID NO: 9) | Yes |
| Cyclin A-1 | A2 | MAFAEDVYEV (SEQ ID NO: 10) | Yes |
| Cyclin A-1 | A2 | TLKSDLHFL (SEQ ID NO: 11) | Yes |
| Cyclin A-1 | A2 | SLGTDVINV (SEQ ID NO: 12) | Yes |
| Cyclin A-1 | A2 | YQYLREAEI (SEQ ID NO: 13) | Yes |
| Cyclin A-1 | A2 | RTILVDWLV (SEQ ID NO: 14) | Yes |
| Cyclin A-1 | A2 | ILVDWLVEV ((SEQ ID NO: 15) | Yes |
| Cyclin A-1 | A2 | KLRAETLYL (SEQ ID NO: 16) | Yes |
| Cyclin A-1 | A2 | FLDRFLSCM (SEQ ID NO: 3) | Yes |
| Cyclin A-1 | A2 | VLRGKLQLV (SEQ ID NO: 17) | Yes |
| Cyclin A-1 | A2 | QLLKMEHLL (SEQ ID NO: 18) | Yes |
| Cyclin A-1 | A2 | KVLAFDLTV (SEQ ID NO: 19) | Yes |
| Cyclin A-1 | A2 | NLAKYVAEL (SEQ ID NO: 20) | Yes |
| Cyclin A-1 | A2 | SLLEADPFL (SEQ ID NO: 21) | Yes |
| Cyclin A-1 | A2 | YLPSLIAAA (SEQ ID NO: 22) | Yes |
| Cyclin A-1 | A2 | LIAAAAFCL (SEQ ID NO: 6) | Yes |
| Cyclin A-1 | A2 | FTGYSLSEI (SEQ ID NO: 23) | Yes |
| Cyclin A-1 | A2 | SLSEIVPCL (SEQ ID NO: 24) | Yes |
| Cyclin A-1 | A2 | SLMEPPAVL (SEQ ID NO: 25) | Yes |
| Cyclin A-1 | A2 | YAEEIYQYL (SEQ ID NO: 1) | Yes |
| Cyclin A-1 | A2 | AETLYLAVN (SEQ ID NO: 2) | No |
| Cyclin A-1 | A2 | ASKYEEIYP (SEQ ID NO: 4) | No |

* The combination estimates aspects of epitope chemistry, biochemistry, processing, and immunogenicity.

Bold indicates epitopes also identified by Ochsenreuther et al. (Ochsenreither, et al. *Blood* 119(23):5492-5501 (2012)) although LIAAAAFCL (SEQ ID NO:6) was identified within a 11mer.

This example illustrates a key difference between the methods disclosed by Ochsenreuther and the methods disclosed herein. The Ochesenreuther approach relies on the T cell reactivity to define the antigenic targets, leaving open the possibility for individual bias in immune response, the second relies on unbiased in silico chemistry and biochemistry, which is only then followed by a search of T cells reacting to the specific antigen. The identification of multiple epitopes increases the likelihood of finding suitable TCRs against the target.

Example 3. The Derivation of HP-Ag Peptides Homologous to Sequences within NUTM (1) Fusion Protein Expressed in NUT Midline Cancers (NMC) and Other NUT Associated Soft Tissue and Visceral Tumors BRD4-NUT ((bromodomain containing 4 protein-nuclear protein in testis) is a fusion protein present in a subset of NUT midline cancers. The BRD4-NUT fusion is the most common NUT fusion and thus served as the standard for analysis. However, other fusion partners exist in NUT midline carcinoma as well as other soft tissue and visceral tumors (Dickson K, et al. *Am J Surg Pathol* 42:636-645 (2018). All NUT-associated tumors are poorly differentiated and highly aggressive tumors. NUT midline carcinomas are non-operable with few treatment options (French *Nature Reviews Cancer* 14:149-150 (2014)). Recently, bromodomain inhibitors have been tested in NUT midline cancers with promising but temporary results (Stathis A, et al. *Cancer Discovery* 6:492 (2016)). If the fusion proteins causing NMC and other NUT-related tumors contained a feasible, safe and potent ACT target, it would offer a valuable treatment option for NUT-associated cancers. It has been found that although the NUT fusion partner can vary, there is little variation in the NUT portion of the fusions (Thompson-Wicking, et al. *Oncogene* 32:4664-4674 (2013) making the broad targeting of NUT-related fusions possible using a single or a few epitopes that will be shared between the fusions. These studies were commenced by evaluating the BRD4-NUT fusion protein in NMC for its target potential based on the parameters of frequency, pattern of expression, and its clinical and commercial feasibility (Frequency), its ability to discriminate cancer cells from normal cells (Specificity), and the strength of its functional relationship to the cancer's ability to perpetuate itself (Functional Connectivity). Since NUT is a CGA only normally expressed in the testis, epitopes related to NUT will be adequately cancer-specific for the NUT fusion proteins.

Step 1. Qualification of BRD4-NUT as an HP-TP or Aux-TP

A. TP Frequency

The BRD4-NUT fusion protein is expressed in approximately 50% of NUT mid-line carcinomas. This high frequency of expression within NUT midline carcinomas gave it a sufficient positive frequency value. The reported frequency of BRD4-NUT cancers is also likely to rise with increased screening, now prompted because of the availability of cancer drugs that target active bromodomains. In addition, there is increasing awareness that heretofore uncharacterized aggressive soft tissue and visceral tumors may indeed represent NUT-associated cancer (Dickson et al. *Am J Surg Pathol* 42:636-645 (2018)).

B. TP Specificity

NUT (also referred to as NUTM1) is a CGA with expression confined to the testis, which under normal circumstances is believed to be involved in the control of the histone acetylase p300 both in post-meiotic male germ cells of the testis. Expression of NUT alone does not necessarily target C-RC, the cells with the most functional significance for the patient.

Finding HP-Ag sequences with homology to sequences within the cancer-specific region of BRD4-NUT has two benefits 1) it ensures that the ACT will target cells that have the active bromodomain driving the cancer while leaving BRD4 activity in normal cells unrecognized and 2) it will target abnormal, cancer-specific NUT expression. All NUT-associated fusions are cancer specific and thus they will have a positive specificity value. Examples of other oncogenic NUT fusions include BRD3-NUT, MXD1-NUT, BCORL1-NUT AND CIC-NUT.

C. TP Functional Connectivity

BRD4 fusion with the CGA-NUT results in abnormal bromodomain activity and abnormal histone acetylation involving p300. The bromodomain motif is a key aspect of epigenetic regulation. In development, lack of BRD4 is lethal. BRD4 has been reported as a key regulator of embryonic stem cell (ES) renewal and pluripotency regulated principally through Nanog expression (Liu et al. *Cell Death Differ.* 21(12):1950-1960 (2014)). BRD4 is down-regulated upon ES differentiation. In cancers, BRD4 regulates c-Myc and selectively binds large clusters of enhancers that control tumor oncogenes (Liu et al. *Cell Death Differ.* 21(12):1950-1960 (2014)). Malregulated BRD4 leads to a loss of proliferative control at least in part, through mechanisms related to stem cell biology. Yan et al. (*J. Biol. Chem.* 286:27663-27675 (2011)) have described BRD4's ability to block differentiation of NUT midline carcinoma cells through downstream repression of c-fos. Bromodomain activity has been established as a cancer drug target.

The NUT component of the fusion binds to and activates the histone acetyl-transferase p300 causing histone hyperacetylation. It is believed that BRD4-NUT sequesters p300 in a self-perpetuating manner, creating a loop that recruits more fusion protein and p300 (Reynoird et al. *The EMBO Journal* 29:2943-2952 (2010). The sequester of p300 prevents its interaction with pro-differentiation genes (Schaefer et al. *Genes Chromosomes Cancer* 57:446-451 (2018)). The histone hyperacetylation is not associated with transcription rather this action is believed to be analogous to NUT's possible role in post-meiotic male germ cells where there is a turn-off of transcriptional activity associated with chromatin compaction (Reynoird et al. *The EMBO Journal* 29:2943-2952 (2010). Important to cancer, the p300 protein modulates the action of p53 (Lill et al. *Nature* 387:823-827 (1997)). Experimentally, release of p300 through the knockdown of BRD4-NUT restores p53-dependent regulation and cell differentiation (Reynoird et al. *The EMBO Journal* 29:2943-2952 (2010). Because both the abnormally active bromodomain as well as the impact of the NUT fusion on histone acetylation and the sequestering of p300, the likelihood that NUT fusion proteins will be active in the C-RC is high and represent a pivotal change capable of defining and driving the cancer supported both clinically (Dickson et al. *Am J Surg Pathol* 42:636-645 (2018)) and experimentally (Thompson-Wicking et al., *Oncogene* 32:4664-4674 (2013). BRD4-NUT's association with development, block of cell differentiation as well as embryonic stem cell renewal provides additional links to C-RC biology. This connection to the C-RC can be further corroborated in C-RC derived from Nut midline carcinoma using technology that activates a regenerative response in vitro.

The potential therapeutic value of the BRD4-NUT was positive for frequency, specificity and functional connectivity (Table 3).

TABLE 3

Step 1 Calculation of BRD4-NUT HP-TP potential

| Candidate HP-TP | Frequency | Specificity | Functional Connectivity | Qualifies as an HP-TP? |
|---|---|---|---|---|
| BRD4-NUT | 9 | 10 | 4 | Yes |

Positive assessment of Frequency, Specificity and Functional Connectivity qualified BRD4-NUT to advance to Step 2.

Step 2. Identification of Candidate HP-Ag Sequences

The BRD4-NUT sequence used to identify high probability candidate HP-Ag:

(SEQ ID NO: 26)
EPSLKNSNPDEIEIDFETLKPSTLRELERYVTSCLRKKRKPQAEKVDVIA

GSSKMKGFSSSESESSSESSSSDSEDSETASALPGPDMSMKPSAALSPSP

ALPFLPPTSDPPDHPPREPPPQPIMPSVFSPDNPLMLSAFPSSLLVTGDG

GPCLSGAGAGKVIVKVKTEGGSAEPSQTQNFILTQTALNSTAPGTPCGGL

EGPAPPFVTASNVKTILPSKAVGVSQEGPPGLPPQPPPPVAQLVPIVPLE

KAWPGPHGTTGEGGPVATLSKPSLGDRSKISKDVYENFRQWQRYKALARR

HLSQSP

Overlapping 9 peptide sequences where evaluated manually and using a comprehensive integrated algorithm that assigned weighted values to the sequence's chemistry, antigen processing, HLA specificity, and binding kinetics and that incorporated known positive and negative T cell epitopes as controls. A total of 298 sequences within the BRD4-NUT fusion region were screened.

TABLE 4

Candidate HP-Ag sequences (9-mer sequences) in the BRD4-NUT with their HLA A2 specificity

| Target | HLA Specificity | Core 9mer sequence | HP Sequence based on the method of Step 2* |
|---|---|---|---|
| BRD4-NUT | A2 | TLRELERYV (SEQ ID NO: 27) | Yes |
| BRD4-NUT | A2 | MLSAFPSSL (SEQ ID NO: 28) | Yes |
| BRD4-NUT | A2 | SAFPSSLLV (SEQ ID NO: 29) | Yes |
| BRD4-NUT | A2 | ILPSKAVGV (SEQ ID NO: 30) | Yes |
| BRD4-NUT | A2 | ALPGPDMSM (SEQ ID NO: 31) | Yes |
| BRD4-NUT | A2 | MSMKPSAAL** (SEQ ID NO: 32) | Yes |
| BRD4-NUT | A2 | AALSPSPAL** (SEQ ID NO: 33) | Yes |
| BRD4-NUT | A2 | AQLVPIVPL (SEQ ID NO: 37) | Yes |

*The combination estimates aspects of epitope chemistry, biochemistry, processing, and immunogenicity.
**Identified as a candidate sequence for more than one HLA type.

Several sequences were identified as having comparable molecular characteristics as good or better than well-characterized epitopes with known in vivo immunogenicity and in particular, T cell reactivity. Upon analyzing multiple target proteins, the data showed that not all parameters were consistent between proteins, emphasizing the need for multiple, corroborative data points. Sequences that did not reach consensus were re-examined manually. Sequences from some target proteins showed a very high consensus between the computerized Algorithm II and manual selection whereas in others, the algorithm identified additional sequences not selected manually. This was true of BRD4-NUT. Algorithm II identified one sequence that was simply missed in the manual selection (AQLVPIVPL (SEQ ID NO:37). In addition, it identified 3 sequences that were not selected because of border-line values in some parameters discounted in the manual selection. These sequences were now converted to "yes" with the support of Algorithm II (which mathematically takes into account positive and negative controls). Of interest was the fact that two of the three conversions were identified manually for other HLA types. Sequences not reaching consensus were put on hold. The sequences able to reach consensus for A2, or positively identified manually in other HLA types, advanced to Step 3.

Available data for HLA-A2 are the most complete data available, including the availability of control data. This data was used to construct Algorithm II. However, there were sufficient available data covering most parameters to manually select epitopes for additional HLA types from the comprehensive data set. Results using the scheme validated for A2 by Algorithm II can be used for the manual curation of non-A2 sequences. In turn the selections can then be used to adjust Algorithm II to handle the non-available data points and accommodate evaluation of additional HLA types. The most common HLA types could be analyzed. Further experiments focused on major HLA types that, in addition to A2, would be present in a majority of patients in North America, Europe and Asia (Table 5).

TABLE 5

Candidate HP-Ag sequences (9-mer sequences) in BRD4-NUT with their HLA specificity

| Target | HLA Specificity | Core 9 mer sequence | HP Sequence based on methods of Step 2* |
|---|---|---|---|
| BRD4-NUT | A3, A11 | CLSGAGAGK (SEQ ID NO: 38) | Yes |
| BRD4-NUT | A3, A1 | VIAGSSKMK (SEQ ID NO: 39) | Yes |
| BRD4-NUT | A3 | YVTSCLRKK (SEQ ID NO: 40) | Yes |
| BRD4-NUT | B7 | KPQAEKVDV (SEQ ID NO: 41) | Yes |
| BRD4-NUT | B7, B8 | MSMKPSAAL** (SEQ ID NO: 32) | Yes |
| BRD4-NUT | B7 | KPSAALSPS SEQ ID NO: 42) | Yes |

TABLE 5-continued

Candidate HP-Ag sequences (9-mer sequences) in BRD4-NUT with their HLA specificity

| Target | HLA Specificity | Core 9 mer sequence | HP Sequence based on methods of Step 2* |
|---|---|---|---|
| BRD4-NUT | B7 | AALSPSPAL*** (SEQ ID NO: 33) | Yes |
| BRD4-NUT | B7 | SPSPALPFL (SEQ ID NO: 43) | Yes |
| BRD4-NUT | B7 | SPALPFLPP (SEQ ID NO: 44) | Yes |
| BRD4-NUT | B7 | PPQPIMPSV (SEQ ID NO: 45) | Yes |
| BRD4-NUT | B7 | APGTPCGGL (SEQ ID NO: 46) | Yes |
| BRD4-NUT | B7 | GPAPPFVTA (SEQ ID NO: 47) | Yes |
| BRD4-NUT | B7 | LPPQPPPPV (SEQ ID NO: 48) | Yes |
| BRD4-NUT | B7 | QPPPPVAQL (SEQ ID NO: 49) | Yes |
| BRD4-NUT | A3, A11 | AGAGKVIVK (SEQ ID NO: 200) | Yes |
| BRD4-NUT | A3, A11 | NVKTILPSK (SEQ ID NO: 201) | Yes |
| BRD4-NUT | A3, A11 | LVPIVPLEK (SEQ ID NO: 202) | Yes |
| BRD4-NUT | A11 | IEIDFETLK (SEQ ID NO: 203) | Yes |
| BRD4-NUT | A11 | ETLKPSTLR (SEQ ID NO: 204) | Yes |
| BRD4-NUT | A11 | RYVTSCLRK (SEQ ID NO: 205) | Yes |
| BRD4-NUT | A11 | YVTSCLRKK (SEQ ID NO: 206) | Yes |
| BRD4-NUT | A11 | TSCLRKKRK (SEQ ID NO: 207) | Yes |
| BRD4-NUT | A24 | LSPSPALPF (SEQ ID NO: 208) | Yes |
| BRD4-NUT | A24, B15 | PQPIMPSVF (SEQ ID NO: 209) | Yes |
| BRD4-NUT | A24 | VFSPDNPLM (SEQ ID NO: 210) | Yes |
| BRD4-NUT | A24 | FSPDNPLML (SEQ ID NO: 211) | Yes |
| BRD4-NUT | A24 | LSAFPSSLL (SEQ ID NO: 212) | Yes |
| BRD4-NUT | A24 | VTASNVKTI (SEQ ID NO: 213) | Yes |
| BRD4-NUT | A24 | ISKDVYENF (SEQ ID NO: 214) | Yes |
| BRD4-NUT | B7 | SVFSPDNPL (SEQ ID NO: 215) | Yes |
| BRD4-NUT | B7, B8, B15 | MLSAFPSSL (SEQ ID NO: 28) | Yes |
| BRD4-NUT | B7 | PPVAQLVPI (SEQ ID NO: 216) | Yes |
| BRD4-NUT | B7 | VATLSKPSL (SEQ ID NO: 217) | Yes |
| BRD4-NUT | B7; B8, B15 | RQWQRYKAL (SEQ ID NO: 218) | Yes |
| BRD4-NUT | B8 | LERYVTSCL (SEQ ID NO: 219) | Yes |
| BRD4-NUT | B8 | CLRKKRKPQ (SEQ ID NO: 220) | Yes |
| BRD4-NUT | B8 | LRKKRKPQA (SEQ ID NO: 221) | Yes |
| BRD4-NUT | B8 | RKKRKPQAE (SEQ ID NO: 222) | Yes |
| BRD4-NUT | B8 | NFILTQTAL (SEQ ID NO: 223) | Yes |
| BRD4-NUT | B8 | ALARRHLSQ (SEQ ID NO: 224) | Yes |
| BRD4-NUT | B15 | ALPGPDMSM (SEQ ID NO: 31) | Yes |
| BRD4-NUT | B15 | TQTALNSTA (SEQ ID NO: 225) | Yes |

TABLE 5-continued

Candidate HP-Ag sequences (9-mer sequences) in BRD4-NUT with their HLA specificity

| Target | HLA Specificity | Core 9 mer sequence | HP Sequence based on methods of Step 2* |
|---|---|---|---|
| BRD4-NUT | B15 | GLEGPAPPF (SEQ ID NO: 226) | Yes |
| BRD4-NUT | B15 | AQLVPIVPL (SEQ ID NO: 37) | Yes |
| BRD4-NUT | B15 | RSKISKDVY (SEQ ID NO: 227) | Yes |
| BRD4-NUT | B15 | ISKDVYENF (SEQ ID NO: 214) | Yes |
| BRD4-NUT | B15 | WQRYKALAR (SEQ ID NO: 228) | Yes |

NA = not yet available.
***Identified as a candidate sequence for more than one HLA type.

Step 3. Screen of Candidate HP-Ag for Specificity and Off-Target Potential

The candidate HP-Ag peptide sequences were then screened for peptide specificity and off target reactivity potential using a BLASTp screen employing parameters optimized for short sequence analysis and preference for minimal substitution and compositional adjustments (Step 3.V1). Probability values for both On-target and Off-target returned results are then analyzed and a composite algorithm-generated value is used to determine an overall specificity rating. The greater the composite value the more specific the target sequence.

Analysis was first developed empirically and then an algorithm was designed for this evaluation to provide consistency and reduce potential bias.

Candidate HP-Ag sequences that passed with a difference in off-target potential of 500-fold or more were qualified as HP-Ag (Table 6).

TABLE 6

HP-Ag sequences identified in the BRD4-NUT fusion region using the method of Step 3.V1

| Candidate HP sequence (HLA Specificity) | SEQ ID NO: | Specificity Rating (Fold Difference between Specific Target and Non-Target) | Qualified HP-Ag? |
|---|---|---|---|
| TLRELERYV (A2) | 27 | 1.33E+03 | Yes |
| ALPGPDMSM (A2, B15) | 31 | 5.11E+03 | Yes |
| MSMKPSAAL (A2, B7, B8) | 32 | 1.87E+03 | Yes |
| CLSGAGAGK (A3, A11) | 38 | 9.1E+02 | Yes |
| VIAGSSKMK (A3, A11) | 39 | 1.9E+03 | Yes |
| KPQAEKVDV (B7) | 41 | 8.67E+02 | Yes |
| SPALPFLPP (B7) | 44 | 4.24E+03 | Yes |
| PPQPIMPSV (B7) | 45 | 2.13E+03 | Yes |
| APGTPCGGL (B7) | 46 | 2.28E+03 | Yes |
| GPAPPFVTA (B7) | 47 | 6.76E+02 | Yes |
| AGAGKVIVK (A3, A11) | 200 | 6.70E+02 | Yes |
| NVKTILPSK (A3, A11) | 201 | 6.79E+02 | Yes |
| LVPIVPLEK (A3, A11) | 202 | 5.77E+02 | Yes |
| IEIDFETLK (A11) | 203 | 2.12E+03 | Yes |
| PQPIMPSVF (A24, B15) | 209 | 5.07E+02 | Yes |
| VFSPDNPLM (A24) | 210 | 4.80E+03 | Yes |
| FSPDNPLML (A24) | 211 | 4.86E+03 | Yes |
| VTASNVKTI (A24) | 213 | 1.93E+03 | Yes |

TABLE 6-continued

HP-Ag sequences identified in the BRD4-NUT fusion region using the method of Step 3.V1

| Candidate HP sequence (HLA Specificity) | SEQ ID NO: | Specificity Rating (Fold Difference between Specific Target and Non-Target) | Qualified HP-Ag? |
|---|---|---|---|
| ISKDVYENF (A24, B15) | 214 | 2.23E+03 | Yes |
| SVFSPDNPL (B7) | 215 | 1.27E+03 | Yes |
| PPVAQLVPI (B7) | 216 | 1.65E+03 | Yes |
| RQWQRYKAL (B7, B8, B15) | 218 | 1.07E+04 | Yes |
| LERYVTSCL (B8) | 219 | 2.86E+03 | Yes |
| CLRKKRKPQ (B8) | 220 | 1.07E+03 | Yes |
| RKKRKPQAE (B8) | 222 | 7.40E+02 | Yes |
| NFILTQTAL (B8) | 223 | 1.79E+03 | Yes |
| TQTALNSTA (B15) | 225 | 9.40E+02 | Yes |
| GLEGPAPPF (B15) | 226 | 7.61E+02 | Yes |
| RSKISKDVY (B15) | 227 | 3.29E+03 | Yes |
| WQRYKALAR (B15) | 228 | 5.91E+03 | Yes |
| AEPSQTQNF (A24) | 229 | 2.89E+03 | Yes |
| EIEIDFETL (A24) | 230 | 1.64E+03 | Yes |
| YKALARRHL (B8) | 234 | 2.27E+03 | Yes |

The sequences identified with a passing off-target potential were subjected to the more stringent three-tier specificity calculation method (Step 3.V2). Twelve of 33 epitopes failed the more comprehensive test. A score of zero indicates that the sequence failed first-tier specificity. A number greater than zero indicates that the sequence failed in either the second- or third-tier calculation of fold-difference in Off-target potential. NUT is a CGA and therefore is not expressed in normal tissue outside of the testis so peptides within NUT but not BRD4, were be included as cancer-specific epitopes of the HP-TP fusion protein. The Sequences that passed step 3V.2 are shown in Table 7.

TABLE 7

BRD4-NUT Epitopes Evaluated Using Third Step, Three-tier Specificity Calculation

| HLA | SEQUENCE | Sequence ID | 1° Specificity PASS or FAIL | Highest Off-target potential from second and third tiers | Final Result |
|---|---|---|---|---|---|
| A2 | TLRELERYV | 27 | FAIL | 0.00E+00 | FAIL |
| A2, B15 | ALPGPDMSM | 31 | PASS | 1.78E+03 | PASS |
| A2, B7, B8 | MSMKPSAAL | 32 | PASS | 3.69E+03 | PASS |
| A3, A11 | CLSGAGAGK | 28 | PASS | 6.10E+02 | PASS |
| A3, A11 | VIAGSSKMK | 39 | FAIL | 0.00E+00 | FAIL |
| B7 | KPQAEKVDV | 41 | FAIL | 0.00E+00 | FAIL |
| B7 | SPALPFLPP | 44 | PASS | 1.08E+02 | FAIL |
| B7 | PPQPIMPSV | 45 | PASS | 1.00E+03 | PASS |
| B7 | APGTPCGGL | 46 | PASS | 5.90E+02 | PASS |
| B7 | GPAPPFVTA | 47 | PASS | 3.81E+02 | FAIL |
| A3, A11 | AGAGKVIVK | 200 | PASS | 5.23E+02 | PASS |

TABLE 7-continued

BRD4-NUT Epitopes Evaluated Using Third Step, Three-tier Specificity Calculation

| HLA | SEQUENCE | Sequence ID | 1° Specificity PASS or FAIL | Highest Off-target potential from second and third tiers | Final Result |
|---|---|---|---|---|---|
| A3, A11 | NVKTILPSK | 201 | PASS | 1.39E+03 | PASS |
| A3, A11 | LVPIVPLEK | 202 | PASS | 1.08E+02 | FAIL |
| A11 | IEIDFETLK | 203 | FAIL | 0.00E+00 | FAIL |
| A24, B15 | PQPIMPSVF | 209 | PASS | 3.76E+03 | PASS |
| A24 | VFSPDNPLM | 210 | PASS | 1.40E+03 | PASS |
| A24 | FSPDNPLML | 211 | PASS | 1.84E+04 | PASS |
| A24 | VTASNVKTI | 213 | PASS | 1.49E+03 | PASS |
| A24, B15 | ISKDVYENF | 214 | PASS | 9.33E+02 | PASS |
| B7 | SVFSPDNPL | 215 | PASS | 2.18E+03 | PASS |
| B7 | PPVAQLVPI | 216 | PASS | 2.30E+03 | PASS |
| B7, B8, B15 | RQWQRYKAL | 218 | PASS | 1.13E+04 | PASS |
| B8 | LERYUTSCL | 219 | FAIL | 0.00E+00 | FAIL |
| B8 | CLRKKRKPQ | 220 | FAIL | 0.00E+00 | FAIL |
| B8 | RKKRKPQAE | 222 | FAIL | 0.00E+00 | FAIL |
| B8 | NFILTQTAL | 223 | PASS | 3.30E+03 | PASS |
| B15 | TQTALNSTA | 225 | PASS | 4.66E+03 | PASS |
| B15 | GLEGPAPPF | 226 | PASS | 1.53E+03 | PASS |
| B15 | RSKISKDVY | 227 | PASS | 2.75E+04 | PASS |
| B15 | WQRYKALAR | 228 | PASS | 6.90E+01 | PASS |
| A24 | AEPSQTQNF | 229 | PASS | 1.36E+04 | PASS |
| A24 | EIEIDFETL | 230 | FAIL | 0.00E+00 | FAIL |
| B8 | YKALARRHL | 234 | PASS | 1.70E+01 | FAIL |

Twelve off the thirty-three sequences that passed Step 3.V1 failed using the more stringent and comprehensive Step 3.V2 method. Peptides with zero Off-target potential failed first-tier specificity. All other failures were due to insufficient fold-difference between on-target and off-target potential.

Example 4. HP-Ag Peptides Homologous to Sequences within ALK Fusion Proteins Expressed in Cancer Anaplastic lymphoma kinase (ALK) was first discovered as part of the fusion protein NPM-ALK in anaplastic large cell lymphoma. ALK fusion proteins have been recognized as oncogenic and the constitutive ALK activity caused by ALK translocations is a current target of several cancer drugs that block ALK activity. The predominant ALK fusion proteins are NPM-ALK, EML4-ALK and TMP3-ALK as well as additional less frequent translocations. However, normal ALK expression is seen in neural development and it remains at a low level in the adult brain. Also, ALK has a 64% homology to leukocyte tyrosine kinase (Turner et al. *Leukemia* 19:1128-1134 (2005)) and it belongs to the insulin receptor superfamily (Mourali et al. *Molecular and Cellular Biology* 26:6209-6222 (2006)). These facts could place safe targeting of ALK by ACT out of reach. These studies were conducted based on the hypothesis that ALK positive tumors could be targeted for HP-ACT by specifically targeting the novel sequence formed by the fusion. Of particular interest was a linker region shared by the ALK fusion proteins. Identifying specific antigenic sequences within this region would make ALK positive cancers feasible indications for ACT therapy, in particular, HP-ACT.

The first step in these studies was evaluating the fusion protein for its target potential based on the parameters of frequency, pattern of expression, and its clinical and commercial feasibility (Frequency), its ability to discriminate cancer cells from normal cells (Specificity), and the strength of its functional relationship to the cancer's ability to perpetuate itself (Functional Connectivity).

Step 1. Qualification of ALK Fusion Family Members as HP-TP or Aux-TP

A. TP Frequency

The first step was performed based on the hypothesis that suitable HP-Ag neoantigens might be present within the novel fusion regions of the ALK fusion proteins. This would allow safe targeting of ALK by ACT while being able to use a target to treat multiple ALK positive cancers. A sequence region was found that was shared by multiple ALK fusions including EML4-ALK, NPM-ALK and TMP-ALK:

(SEQ ID NO: 50)
KGAEIKTTNEVVLAVEFHPTDANTIITCGKSHIFFWTWSGNSLTRKQGIF

GKYEKPKFVQCLAFLGNGDVLTGDSGGVMLIWSKTTVEPTPGKGPKGVYQ

LSKQLKAHDGSVFTLCQMRNGMLLTGGGKDRKIILWDHDLNPEREIMELQ

SPEYKLSKLRTSTIMTDYNPNYCFAGKTSSISDLKEVPRKNITLIRGLGH

GAFGEVYEGQVSGMPNDPSPLQ.

Overall, EML4-ALK frequency in non-small cell lung cancer has been reported at 4-13% (Shaw et al. *J. Clinical Oncology* 27(26):4247-4253 (2014)). Work on ALK drug targeting has helped define a subset of patients where the frequency of EML4-ALK rises to 22% for patients with a history of little to no smoking (Shaw et al. *J. Clinical Oncology* 27(26):4247-4253 (2014)) and climbs to 33% for patients that do not have a mutation in epidermal growth factor receptor (EGFR mutations are present approximately 22% of NSCLC) (Shaw et al. *J. Clinical Oncology* 27(26):4247-4253 (2014)). According to SEER statistics, there are over 400,000 patients with lung cancer in the US alone, with an estimated 224,210 new cases and 159,260 deaths expected in 2014. Even 4% of these numbers was sufficient to qualify EML4-ALK based on number of patients. Feasibility is increased by the ability to triage the large patient population. Also, EML4-ALK may be applicable to additional indications, which would further increase its value. NPM-ALK is present in approximately 43% of anaplastic large cell lymphoma stratified by age to as high as 83% in pediatric patients compared to 31% in adults. The high frequency within ALCL qualifies it as a feasible target for ACT in this indication.

One example of an indication that might not achieve a feasible frequency on its own is the rare inflammatory myofibroblastic tumor (IMT). IMTs represent about 1% of lung tumors and it is estimated that up to 50% of IMTs will be TMP3-ALK positive. Of note is that IMT can occur anywhere in the body. While IMT is more common in the lung in young patients, it has been reported in people of all ages (Gleason et al. *J. Clin. Pathol.* 61:428-437 (2008)). Although these tumors have a low metastatic potential, recurrence can be as high as 40% attributed to the lack of ability to entirely remove the tumor. IMT has been historically described using a number of terms, making its total prevalence difficult to estimate.

B. TP Specificity

Nucleophosmin (NPM) is a ubiquitous 'housekeeping' protein involved in many basic cell functions including DNA replication, protein formation and cell cycle progression. Targeting epitopes common to normal NPM would not be feasible. The same is true of the other ALK fusion partners; echinoderm microtubule-associated protein like protein 4 (EML4), binds and stabilizes mictotubules, the third major fusion partner tropomyosin 3 is a normal component of the cytoskeleton. All three are important for normal cell function and so the fusion of ALK now under their regulation drives constitutive ALK activity. Normal anaplastic lymphoma kinase (ALK) is more tightly expressed. In mice it appears during neural development and then remains in low amounts in the adult nervous system. In humans, ALK is detected in some pericytes (the contractile cells of the microvasculature throughout the body) and in glia in some areas of the brain (Passoni et al. *Blood* 99:2100-2106 (2002)). Both NPM-specific regions and ALK-specific regions will lack the specificity needed to qualify it as an HP-TP candidate. However, ALK fusions are specific to cancer and rare disease. Targeting the fusion region allows selective targeting of cells containing the abnormal ALK fusion while avoiding cells with normal NPM and ALK expression giving the fusion protein a positive specificity value, if the antigen is within the unique region particular to the fusion protein.

C. TP Functional Connectivity

ALK has been shown to be a powerful driver of oncogenesis. The expression of ALK is driven by the fusion partner so the different ALK fusions exhibit preferential cancer expression for example: NPM-ALK in anaplastic lymphoma kinase; EML4-ALK in non-small cell lung cancer; TMP3-ALK in inflammatory myofibroblastic tumors. In all cases, the fusion results in constitutive expression of ALK. It acts through at least three pathways with many interconnections: The Ras-ERG pathway, well-established as a driver of cell-cycle progression, the JAK-STAT and STAT 3 pathways, involved in proliferation and survival respectively, and PI3K involved in survival and proliferation (Chiarle et al. *Nature Reviews Cancer* 8:11-23 (2008)). More recently, NPM-ALK has been connected to increased Sox2 expression, Sox2 an important stem cell protein involved in the maintenance of pluripotency in normal stem cells (Gelebart et al. *Blood Cancer J.* 2:e82; doi:10.1038/bcj.2012.27 (2012)). ALK is normally a transmembrane protein however the fusion renders it cytoplasmic, eliminating it as a candidate for CAR ACT. Since ALK activity acts as a pivotal driver in ALK+ cancers, the likelihood that C-RC would have to contain the fusion protein is high (Passoni et al., *Blood* 99:2100-2106 (2002)) and the chance that cells lacking the fusion protein would be C-RC in an ALK-fusion positive cancer is low. The dependence on ALK activity afforded by the translocation established a positive connection to the C-RC of the cancer. Cells lacking expression of the ALK fusion would be unlikely to perpetuate the cancer.

Curated analysis qualified the family of ALK fusion proteins as HP-TP and continuation to Step 2.

TABLE 8

Step 1 Calculation of ALK fusion HP-TP potential

| Candidate HP-TP | Frequency | Specificity | Functional Connectivity | Qualifies as an HP-TP? |
|---|---|---|---|---|
| ALK fusion | 4 | 6 | 4 | Yes |

Step 2. Identification of Candidate HP-Ag Sequences

This example is not the first attempt to identify ALK T cell antigens suitable for cancer immunotherapy and so in addition to identifying fusion region antigens, Step 2 as disclosed herein was tested against the previous derivation of ALK fusion epitopes. In 2002, Passoni et al. (Passoni et al. *Blood*, 99:2100-2106 (2002)) identified several potential T cell antigens to target abnormal ALK activity in anaplastic lymphoma kinase that harbors an NPM-ALK translocation. The Passoni strategy was to avoid the ubiquitous NPM and focus on the more restricted and differentially expressed ALK. ALK-specific targeting will have insufficient specificity to qualify ALK kinase-region antigens for HP-ACT, making peptides from the ALK kinase region unsuitable for HP-ACT development. This experiment aimed to compare the Passoni method of epitope identification with the method of Step 2 as disclosed herein, in their ability to discern T reactive epitopes. The ability to predict the 9 amino acid core sequences identified by Passoni, using step 2 as disclosed herein was assessed.

Passoni began their studies by assessing potential binding of ALK peptides using a single method that estimated binding to HLA A2, and selecting 22, 9 and 10 amino acid peptides within and bordering the kinase region of ALK. Passoni then tested the peptides for their ability to mount a response in transgenic mice as well as in vitro, using transgenic mouse lymphocytes and naïve normal human donor lymphocytes. Of the 22 predicted peptides, 9 exhibited strong binding to HLA A2 with sufficient stability to likely elicit a T cell response. In vivo, 7 of the 9 peptides were able to mount a T cell response in mice transgenic for HLA A2. Differences in outcome emphasized that affinity alone without sufficient stability was an ineffective predictor of T cell response. They identified two 10 amino acid peptides that were capable of stimulating a T cell response in transgenic mice, killing of NPM-ALK positive cells, and that could stimulate T cells from one of three normal patients.

The selection process disclosed herein factors in affinity and stability as well as other parameters for more efficient identification of potential epitopes. Step 2 was able to identify core 9mers within the 10mer antigens with some important additional information. Of the 9mer sequences within the 22 peptides selected by Passoni Step 2 would have eliminated 7 epitopes before T cell selection and would have identified all 9 positive responders for T cell screening. Of the 9 reactive peptides, Passoni ultimately identified SLAMLDLLHV (SEQ ID NO:51) and GVLLWEIFSL (SEQ ID NO:52) as reactive human T cell antigens. Step 2 identified LAMLDLLHV (SEQ ID NO:53) and VLLWEIFSL (SEQ ID NO:54) as high probability epitopes and therefore would have selected for core 9 amino acid sequences within the peptides selected as best by Passoni. However, within GVLLWEIFSL (SEQ ID NO:52), Step 2 predicted VLLWEIFSL (SEQ ID NO:54) to be a very strong epitope whereas GVLLWEIFS was not. This is supported by Passoni's own data which showed that transgenic animals immunized with the VLLWEISFSL peptide generated HLA A2 T cells that exhibited better T cell lysis (E/T ratio of 48-24-21) than mice immunized with GVLLWEIFSL (SEQ ID NO:52) (E/T ratio of 24-15-15). Within SLAMLDLLHV (SEQ ID NO:51), the SLAMLDLLH (SEQ ID NO:199) 9mer did not qualify as an epitope in these studies, although LAMLDLLHV (SEQ ID NO:53) did, again suggesting that the reactivity was more dependent on the C-terminal portion of the peptide. This provides evidence that the Step 2 screen is able to capture high probability T cell epitopes with greater efficiency and predictability while providing additional information that can aid the use of the sequences as tools for T cell selection and ACT design.

While Passoni believed that they had to avoid targeting NPM because of its ubiquitous nature, they believed that ALK cross-reactivity would be non-existent. However, recent clinical experience in the use of MAGE A3 (Melanoma-associated antigen 3) targets for ACT (a target noted by Passoni as support for the safety of such targets back in 2002), make it clear that ALK itself is unlikely to be a feasible target for ACT despite its natural antigenicity. This barrier to ALK fusions as an ACT target is eliminated if novel, antigenic sequence can be found in the fusion protein.

The following sequence: KGAEIKTTNEVV-LAVEFHPTDANTIITCGKSHIFFWTWSGNSLTRKQGIF GKYEKPKFVQCLAFLGNGDVLTGDSGGVM-LIWSKTTVEPTPGKGPKGV YQL-SKQLKAHDGSVFTLCQMRNGMLLTGGGKDR KIILWDHDLNPEREI MELQSPEYKLSKLRTSTIMT-DYNPNYCFAGKTSSISDLKEVPRKNITL IRGLGHGAF-GEVYEGQVSGMPNDPSPLQ (SEQ ID NO:55) was used for the discovery of HP-Ag peptides. Bold indicates sequence shared by EML4-ALK isoforms, NPM-ALK and TMP3 ALK.

Overlapping 9 amino acid sequences within the master sequence were evaluated manually and by computer algorithm valuing the sequence's chemistry, antigen processing, HLA specificity, and binding kinetics. A total of 212 peptides were analyzed. Several sequences stood out as having comparable molecular characteristics as good or better than well-characterized epitopes with known in vivo immunogenicity and in particular, T cell reactivity. The system was developed using HLA A2 as the model but most common HLA types could be analyzed. Major HLA types were chosen, that would represent a majority of patients in major populations.

High Probability ALK fusion region sequences with their HLA specificity are shown in Table 9.

TABLE 9

High Probability ALK fusion sequences (candidate HP-Ag sequences) with their HLA specificity

| Target(s) | HLA Specificity | Core 9mer sequence | SEQ ID NO: |
|---|---|---|---|
| EML4-ALK | A2, A11 | TTNEVVLAV | 56 |
| EML4-ALK | A2 | VLAVEFHPT | 57 |
| EML4-ALK | A2, A24 | KFVQCLAFL | 58 |
| EML4-ALK | A2 | FLGNGDVLT | 59 |
| EML4-ALK | A2 | VLTGDSGGV | 60 |
| EML4-ALK | A2, B15 | MLIWSKTTV | 61 |
| EML4-ALK | A2 | KIILWDHDL | 62 |
| EML4-ALK | A2 | ILWDHDLNP | 63 |
| EML4-ALK; NPM-ALK; TMP3-ALK | A2 | ELQSPEYKL | 64 |
| EML4-ALK | A2 | GMPNDPSPL | 65 |
| EML4-ALK | A3, A11 | WSGNSLTRK | 66 |
| EML4-ALK | A3, A11 | TTVEPTPGK | 67 |
| EML4-ALK | A3, A11 | SVFTLCQMR | 68 |
| EML4-ALK | A3, A11 | GMLLTGGGK | 69 |
| EML4-ALK; NPM-ALK; TMP3-ALK | A3, A11, B15 | RTSTIMTDY | 70 |
| EML4-ALK; NPM-ALK; TMP3-ALK | A3, B15 | IMTDYNPNY | 71 |
| EML4-ALK; NPM-ALK; TMP3-ALK | A3, A11 | KTSSISDLK | 72 |
| EML4-ALK; NPM-ALK; TMP3-ALK | A3 | ITLIRGLGH | 73 |

TABLE 9-continued

High Probability ALK fusion sequences (candidate HP-Ag sequences) with their HLA specificity

| Target(s) | HLA Specificity | Core 9mer sequence | SEQ ID NO: |
|---|---|---|---|
| EML4-ALK | B7 | HPTDANTII | 74 |
| EML4-ALK | B7 | KPKFVQCLA | 75 |
| EML4-ALK | B7 | TPGKGPKGV | 76 |
| EML4-ALK | B7 | NPEREIMEL | 77 |
| EML4-ALK; NPM-ALK; TMP3-ALK | B7, B8 | SPEYKLSKL | 78 |
| EML4-ALK; NPM-ALK; TMP3-ALK | B7 | VPRKNITLI | 79 |
| EML4-ALK | A24 | AFLGNGDVL | 80 |
| EML4-ALK | A24, B15 | CQMRNGMLL | 81 |
| EML4-ALK; NPM-ALK; TMP3-ALK | A24, B8 | CFAGKTSSI | 82 |
| EML4-ALK | A11 | GGVMLIWSK | 235 |
| EML4-ALK | A11 | VYQLSKQLK | 236 |
| EML4-ALK | A11 | LTGGGKDRK | 237 |
| EML4-ALK; NPM-ALK; TMP3-ALK | A11 | QSPEYKLSK | 238 |
| EML4-ALK; NPM-ALK; TMP3-ALK | A11 | ISDLKEVPR | 239 |
| EML4-ALK | B8 | EIKTTNEVV | 240 |
| EML4-ALK | B8 | NSLTRKQGI | 241 |
| EML4-ALK | B8, B15 | SLTRKQGIF | 242 |
| EML4-ALK | B8 | YEKPKFVQC | 243 |
| EML4-ALK | B8, B15 | QLKAHDGSV | 244 |
| EML4-ALK | B8 | LCQMRNGML | 245 |
| EML4-ALK | B8 | GGKDRKIIL | 246 |
| EML4-ALK; NPM-ALK; TMP3-ALK | B8 | LSKLRTSTI | 247 |
| EML4-ALK; NPM-ALK; TMP3-ALK | B8 | EVPRKNITL | 248 |
| EML4-ALK | B15 | ITCGKSHIF | 249 |
| EML4-ALK | B15 | LKAHDGSVF | 309 |
| EML4-ALK; NPM-ALK; TMP3-ALK | B15 | IMELQSPEY | 34 |

Step 3. Screen of Candidate HP-Ag for Specificity and Off-Target Potential

The selected peptide sequences were then screened for peptide specificity and off target reactivity potential using a BLASTp screen employing parameters optimized for short sequence analysis and preference for minimal substitution and compositional adjustments as specificity for the intended target sequence is of utmost importance. Probability values for both On-target and Off-target returned results are then analyzed and a composite algorithm-generated value is used to determine an overall specificity rating. The greater the composite value the more specific the target sequence.

Analysis was first developed empirically and then an algorithm was designed for this evaluation to provide consistency and reduce potential bias.

Candidate HP-Ag sequences that passed with low off-target potential using the method of Step 3.V1 are shown in Table 10.

TABLE 10

HP-Ag sequence identified in EML4-ALK

| Candidate HP sequence (HLA Specificity) | Specificity Rating Assessed Fold Difference between Specific Target and Non-Target Using Step3.V1 method | SEQ ID NO: |
|---|---|---|
| TTNEVVLAV (A2) (A11) | 6.55E+02 | 56 |
| VLAVEFHPT (A2) | 9.53E+02 | 57 |
| KFVQCLAFL (A2, A24) | 1.47E+03 | 58 |
| FLGNGDVLT (A2) | 1.24E+03 | 59 |
| MLIWSKTTV (A2), (B15) | 1.60E+04 | 61 |
| KIILWDHDL (A2) | 1.54E+04 | 62 |
| ILWDHDLNP (A2) | 7.00E+03 | 63 |
| *ELQSPEYKL (A2) | 1.70E+03 | 64 |
| GMPNDPSPL (A2) | 3.67E+03 | 65 |
| WSGNSLTRK (A3), (A11) | 4.35E+03 | 66 |
| TTVEPTPGK (A3), (A11) | 1.10E+03 | 67 |
| SVFTLCQMR (A3), (A11) | 1.24E+03 | 68 |
| *RTSTIMTDY (A3), A11, B15) | 1.57E+04 | 70 |
| *IMTDYNPNY (A3)(B15) | 1.95E+04 | 71 |
| *ITLIRGLGH (A3) | 6.95E+02 | 73 |
| HPTDANTII (B7) | 9.22E+02 | 74 |
| KPKFVQCLA (B7) | 9.33E+02 | 75 |
| *SPEYKLSKL (B7)(B8) | 2.25E+03 | 78 |
| *VPRKNITLI (B7)(B8) | 3.08E+03 | 79 |
| AFLGNGDVL (A24) | 1.57E+03 | 80 |
| *CQMRNGMLL (A24)(B15) | 2.25E+04 | 81 |
| *CFAGKTSSI (A24)(B8) | 2.29E+03 | 82 |
| GGVMLIWSK (A11) | 4.2E+03 | 235 |
| LTGGGKDRK (A3, A11) | 6.44E+02 | 237 |
| QSPEYKLSK (A3, A11) | 2.68E+03 | 238 |
| *ISDLKEVPR (A11) | 9.33E+02 | 239 |
| EIKTTNEVV (B8) | 1.17E+03 | 240 |
| NSLTRKQGI (B8) | 6.71E+02 | 241 |

TABLE 10-continued

HP-Ag sequence identified in EML4-ALK

| Candidate HP sequence (HLA Specificity) | Specificity Rating Assessed Fold Difference between Specific Target and Non-Target Using Step3.V1 method | SEQ ID NO: |
|---|---|---|
| SLTRKQGIF (B8)(B15) | 9.99E+02 | 242 |
| YEKPKFVQC (B8) | 1.15E+03 | 243 |
| LCQMRNGML (B8) | 2.25E+04 | 245 |
| *EVPRKNITL (B8) | 3.02E+03 | 248 |
| ITCGKSHIF (A24)(B15) | 2.25E+03 | 249 |

*also identified in NPM-ALK; TMP3-ALK

The following sequences did not qualify as HP-Ag: SEQ ID NO: 34 (also identified in NPM-ALK; TMP3-ALK); SEQ ID NO:35; SEQ ID NO:60; SEQ ID NO:69; SEQ ID NO:72, SEQ ID NO:76; SEQ ID NO: 77; VYQLSKQLK (A11, A24) (SEQ ID NO: 236); QLKAHDGSV (B8)(B15) (SEQ ID NO:244; GGKDRKIIL (B8) (SEQ ID NO:246); LSKLRTSTI (B8) (SEQ ID NO:247) (also identified in NPM-ALK; TMP3-ALK); and LKAHDGSVF (B15) (SEQ ID NO:309).

Sequences qualified using Step 3.V1 were re-evaluated using Step 3.V2 a more stringent and comprehensive evaluation of off-target potential. All sequences failed Step 3.V2 specificity at the first tier. However, there were two sequences that failed with exception as they both contained a specific partial sequence present within EML4-ALK Variant 4, a variant not covered by the master sequence. ELQSPEYKL (SEQ ID 64) and SPEYKLSKL (SEQ ID 78) both contained SPEYKL identified by the Step 3.V2 analysis.

```
fusion protein EML4-ALK variant 4 [Homo sapiens]
GenBank: BAG75147.1
GenPept Identical Proteins Graphics
>BAG75147.1 fusion protein EML4-ALK
variant 4 [Homo sapiens]
                                      (SEQ ID NO: 456)
MDGFAGSLDDSISAASTSDVQDRLSALESRVQQQEDEITVLKAALADVLR

RLAISEDHVASVKKSVSSKGQPSPRAVIPMSCITNGSGANRKPSHTSAVS

IAGKETLSSAAKSGTEKKKEKPQGQREKKEESHSNDQSPQIRASPSPQPS

SQPLQIHRQTPESKNATPTKSIKRPSPAEKSHNSWENSDDSRNKLSKIPS

TPKLIPKVTKTADKHKDVIINQEGEYIKMFMRGRPITMFIPSDVDNYDDI

RTELPPEKLKLEWAYGYRGKDCRANVYLLPTGEIVYFIASVVVLFNYEER

TQRHYLGHTDCVKCLAIHPDKIRIATGQIAGVDKDGRPLQPHVRVWDSVT

LSTLQIIGLGTFERGVGCLDFSKADSGVHLCVIDDSNEHMLTVWDWQRKA

KGAEIKTTNEVVLAVEFHPTDANTIITCGKSHIFFWTWSGNSLTRKQGIF

GKYEKPKFVQCLAFLGNGDVLTGDSGGVMLIWSKTTVEPTPGKGPKGVYQ

ISKQIKAHDGSVFTLCQMRNGMLLTGGGKDRKIILWDHDLNPEREIEICW

MSPEYKLSKLRTSTIIVITDYNPNYCFAGKTSSISDLKEVPRKNITLIRG

LGHGAFGEVYEGQVSGMPNDPSPLQVAVKTLPEVCSEQDELDFLMEALII

SKFNHQNIVRCIGVSLQSLPRFILLELMAGGDLKSFLRETRPRPSQPSSL

AMLDLLHVARDIACGCQYLEENHFIHRDIAARNCLLTCPGPGRVAKIGDF

GMARDTYRASYYRKGGCAMLPVKWMPPEAFMEGIFTSKTDTWSFGVLLWE

IFSLGYMPYPSKSNQEVLEFVTSGGRMDPPKNCPGPVYRIMTQCWQHQPE

DRPNFAIILERIEYCTQDPDVINTALPIEYGPLVEEEEKVPVRPKDPEGV

PPLLVSQQAKREEERSPAAPPPLPTTSSGKAAKKPTAAEVSVRVPRGPAV

EGGHVNMAFSQSNPPSELHRVHGSRNKPTSLWNPTYGSWFTEKPTKKNNP

IAKKEPHERGNLGLEGSCTVPPNVATGRLPGASLLLEPSSLTANMKEVPL

FRLRHFPCGNVNYGYQQQGLPLEAATAPGAGHYEDTILKSKNSMNQPGP
```

3 amino acids were added on either side of the 6 amino acid core to create a test sequence (CWMSPEYKLSKL) (SEQ ID NO: 457) for further analysis using Step 3.V2. The sequence was specific for EML4-ALK Variant 4 however it appeared that the partial sequence CWMSPEYKL was what conferred specificity. SPEYKLSKL (SEQ ID NO: 78) was identified as a T cell epitope as part of the original test sequence (SEQ ID 55) but failed Step 3.V2. The six amino acid sequence SPEYKL is present in ALK tyrosine kinase receptor. Sequence to the left of SPEYKL created the fusion-specific sequences. Further studies investigated how far the potential neoantigen region extended in the N terminal direction in Variant 4. The nonamers IEICWMSPE (SEQ ID NO:458), EIEICWMSP (SEQ ID NO:459), REIEICWMS (SEQ ID NO:460), EREIEICWM (SEQ ID NO:461), PEREIEICW (SEQ ID NO:462), NPEREIEIC (SEQ ID NO:463), LNPEREIEI (SEQ ID NO:464) maintained neoantigen specificity before overlapping with EML4, defining the fusion-specific region as LNPEREIEICWMSPEYKL (SEQ ID NO:464). The 18 amino acid sequence then underwent epitope analysis to determine the presence of T cell antigens Using the method of Step 2 that combines algorithm resources to identify and confirm T cell antigens and the HLA type likely to bind the peptides, a core seven amino acid sequence emerged CWMSPEY (SEQ ID NO:465) as common within identified T cell epitopes of varying length, corroborated by multiple resources. Exemplary Sequences and their HLA Binding partners are shown in Table 11. The epitopes of Step 2 were retested using Step 3.V2. The data is shown also shown in Table 11,

TABLE 11

Exemplary Sequences and their binding partners;
Neoantigens present within EML4-AL Variant 4

| HLA | SEQUENCE | Sequence ID | Lowest fold-difference from second and third tiers | Step 3.V2 PASS or FAIL |
|---|---|---|---|---|
| B15, A11 | EICWMSPEY | aa 8-16 of SEQ ID NO: 464 | 7.33E+04 | PASS |
| A11, A3 | EICWMSPEYK | aa 8-17 of SEQ ID NO: 464 | 8.33E+05 | PASS |
| A11 | IEICWMSPEYK | aa 7-16 of SEQ ID NO: 464 | 1.08E+07 | PASS |
| B15, B44 | IEICWMSPEY | aa 7-17 of SEQ ID NO: 464 | 1.25E+06 | PASS |
| A11, A3 | ICWMSPEYK | aa 9-17 of SEQ ID NO: 464 | 5.50E+04 | PASS |
| A24 | CWMSPEYKIL | aa 10-18 of SEQ ID NO: 464 | 4.40E+04 | PASS |
| A24 | ICWMSPEYKL | aa 9-18 of SEQ ID NO: 464 | 5.44E+05 | PASS |
| A24 | EICWMSPEYKL | aa 8-18 of SEQ ID NO: 464 | 7.71E+06 | PASS |

Example 5. HP-Ag Peptides with Sequence Homology to the Fusion Region of TMPRSS2-ERG Expressed in Prostate Cancer The potential of the TMPRSS2-ERG as an HP-TP was evaluated using curated literature research as well as data from protein and genome databases.

Step 1. Qualification of TMPRSS2-ERG as HP-TP or Aux-TP

A. TP Frequency

Translocations of the ERG gene have resulted in several different fusion proteins in addition to TMPRSS2-ERG: EWS-ERG in Ewing's sarcoma and FUS-ERG in myeloid leukemia as well as NDRG1-ERG in prostate cancer. ETS fusions rank third in all advanced prostate cancer mutations and over 80% are ERG fusions (Robinson et al. *Cell* 161:1215 (2015)). The TMPRSS2-ERG fusion pair is present on average in approximately 50% of all prostate cancers. This qualifies it for frequency.

B. TP Specificity

The fusion gene is abnormal and will not be present in normal cells giving the target a high specificity.

C. TP Functional Connectivity

ERG (ETS-regulated gene), an erythroblast transformation-specific (ETS) transcription factor is abnormally upregulated by the translocation and fusion. Notably, ETS family members are associated with embryonic development, cell proliferation and differentiation (Gene cards). TMPRSS2 (transmembrane protease, serine 2) expression is higher or lower depending on the stage of prostate cancer and may not be pivotal in all stages of prostate cancer. ERG was then evaluated for its significance to prostate cancer biology. ERG's inherent function has been linked with self-renewal (Casey et al. *PLoS One* 7(7):e41668 (2012)). There is evidence that ERG promotion of self-renewal can fuel the accumulation of additional mutations in the proliferative cell compartment and eventually some mutations may overcome the need for ERG expression, even in some TMPRSS2-ERG containing cancers. However, more recent clinical data on expression of the fusion protein in metastases suggest excellent retention of the fusion protein's expression in metastatic disease (Robinson et al. *Cell* 161:1215 (2015)).

Step 1 directs the use of this target toward cancers where ERG-driven self-renewal is still a factor in the cancer's regeneration and establishes the potential relative value of the target as a treatment early in the process so that the potential targets are neither missed nor improperly properly used.

TMPR22-ERG fulfilled the requirements of an HP-TP

TABLE 12

Step 1 Calculation of TMPRSS2-ERG HP-TP potential

| Candidate HP-TP | Frequency | Specificity | Functional Connectivity | Qualifies as an HP-TP? |
|---|---|---|---|---|
| TMPRSS2-ERG | 13 | 12 | 4 | Yes |

Step 2. Identification of Candidate HP-Ag Sequences
The TMPRSS2-ERG sequence used was:

(SEQ ID NO: 83)
MTASSSSDYGQTSKMSPRVPQQDWLSQPPARVTIKMECNPSQVNGSRNSP

DECSVAKGGKMVGSPDTVGMNYGSYMEEKHMPPPNMTTNERRVIVPADPT

LWSTDHVRQWLEWAVKEYGLPDVNILLFQNIDGKELCKMTKDDFQRLTPS

YNADILLSHLHYLRETPLPHLTSDDVDKALQNSPRLMHARNTGGAAFIFP

NTSVYPEATQRITTRPVSYR

A total of 212 overlapping 9 amino acid sequences were analyzed for each HLA type shown and relevant sequences identified (Table 13).

Step 3. Screen of Candidate HP-Ag Sequences for Specificity and Off-Target Potential The selected peptide sequences were then screened for peptide specificity and off target reactivity potential using a BLASTp screen employing parameters optimized for short sequence analysis and preference for minimal substitution and compositional adjustments as specificity for the intended target sequence is of utmost importance. Probability values for both on-target and off-target returned results are then analyzed and a composite algorithm-generated value is used to determine an overall specificity rating. The greater the composite value the more specific the target sequence.

Analysis was first developed empirically and then an algorithm was designed for this evaluation to provide consistency and reduce potential bias. The Step 3.V1 method was further refined by adding manual curation of 1° specificity and a more comprehensive utilization of BLASTp in Step 3.V2.

Candidate HP-Ag sequences that passed with high specificity and low off-target potential were qualified as HP-Ag (Table 13).

TABLE 13

HP-Ag sequences in TMPRSS2-ERG determined using Step 3 V.1

| Candidate HP sequence (HLA Specificity) | Assessed Fold Difference between Specific Target and Non-Target | Qualified HP-Ag? | SEQ ID NO: |
|---|---|---|---|
| WLSQPPARV (A2) | 4.23E+03 | Yes | 84 |
| VIVPADPTL (A2) | 1.74E+03 | Yes | 86 |
| GLPDVNILL (A2) | 8.00E+02 | Yes | 87 |
| ILLSHLHYL (A2, A24, B8) | 1.04E+03 | Yes | 88 |
| KMECNPSQV (A2) | 1.11E+04 | Yes | 89 |
| KALQNSPRL (B7, B8) | 1E+03 | Yes | 90 |
| TLWSTDHVR (A3, A11) | 3.24E+03 | Yes | 91 |
| RQWLEWAVK (A3, A11, B27) | 2.00E+03 | Yes | 92 |
| LLFQNIDGK (A3, A11) | 7.00E+02 | Yes | 93 |
| KMTKDDFQR (A3, A11) | 2.91E+03 | Yes | 95 |
| LLSHLHYLR (A3, A11) | 6.40E+02 | Yes | 96 |
| HLTSDDVDK (A3, A11) | 1.45E+03 | Yes | 97 |
| FIFPNTSVY (A3, B15) FIFPNTSVY | 7.13E+02 | Yes | 98 |
| RITTRPVSY (A3, A11, B15) | 4.46E+03 | Yes | 100 |
| EYGLPDVNI (A24) | 1.95E+03 | Yes | 102 |
| VYPEATQRI (A24) | 1.43E+03 | Yes | 103 |
| SPRVPQQDW (B7) | 7.80E+03 | Yes | 104 |
| PPARVTIKM (B7) | 3.50E+03 | Yes | 105 |
| TPSYNADIL (B7) | 1.88E+03 | Yes | 107 |
| HARNTGGAA (B7) | 1.54E+03 | Yes | 109 |
| YPEATQRIT (B7) | 4.50E+03 | Yes | 110 |
| PRVPQQDWL (B27) | 9.18E+03 | Yes | 111 |
| ARVTIKMEC (B27) | 6.67E+03 | Yes | 112 |
| RRVIVPADP (B27) | 1.75E+03 | Yes | 113 |
| QRLTPSYNA (B27) | 1.33E+03 | Yes | 115 |
| ARNTGGAAF (B27) | 1.62E+03 | Yes | 117 |

TABLE 13-continued

HP-Ag sequences in TMPRSS2-ERG determined using Step 3 V.1

| Candidate HP sequence (HLA Specificity) | Assessed Fold Difference between Specific Target and Non-Target | Qualified HP-Ag? | SEQ ID NO: |
|---|---|---|---|
| SSDYGQTSK (A3, A11) | 1.49E+03 | Yes | 250 |
| GQTSKMSPR (A11) | 2.56E+03 | Yes | 252 |
| SQPPARVTI (A24) | 1.47E+03 | Yes | 253 |
| NYGSYMEEK (A11, A24) | 5.72E+03 | Yes | 254 |
| SYMEEKHMP (A24) | 3.62E+04 | Yes | 255 |
| VNILLFQNI (A24) | 1.14E+03 | Yes | 256 |
| HYLRETPLP (A24) | 2.43E+03 | Yes | 257 |
| NTGGAAFIF (A24) | 4.17E+03 | Yes | 258 |
| VPQQDWLSQ (B7) | 6.00E+03 | Yes | 259 |
| VPADPTLWS (B7) | 3.18E+03 | Yes | 260 |
| SPRLMHARN (B7) | 7.40E+03 | Yes | 261 |
| MTKDDFQRL (B8) | 7.59E+03 | Yes | 262 |
| LHYLRETPL (B8) | 2.90E+03 | Yes | 263 |
| LQNSPRLMH (B15) | 4.91E+03 | Yes | 264 |
| TVGMNYGSY (B15) | 8.75E+03 | Yes | 265 |
| WLEWAVKEY (B15) | 2.78E+04 | Yes | 266 |
| FQNIDGKEL (B15) | 1.47E+03 | Yes | 267 |

Additional candidate sequences and their HLA specificity are:

```
                            (SEQ ID NO: 85)
    (KMVGSPDTV (A2);

(SEQ ID NO: 94)
    NIDGKELCK (A3, A11);

(SEQ ID NO: 99)
    SVYPEATQR (A3, A11);

(SEQ ID NO: 101)
    ITTRPVSYR (A3, A11);

(SEQ ID NO: 106)
    LPDVNILLF (B7);

(SEQ ID NO: 108)
    LPHLTSDDV (B7);

(SEQ ID NO: 114)
    VRQWLEWAV (B27);

(SEQ ID NO: 116)
    LRETPLPHL (B27);

SEQ ID NO: 251)
    MTASSSSDY (A11, B15);
    and (SEQ ID NO: 268)
    TQRITTRPV (B15).
```

TMPRSS2-ERG epitopes identified by the earlier iteration of the algorithm (Step 3.V1) were evaluated for specificity using the three-tier method (Step 3.V2). Only one epitope passed the more extensive test, which included manually-curated tier one protein specificity. The exception was RITTRPVSY (SEQ ID No.100) identified as an epitope to HLA A3, A11 and B15 in step two. The three-tier method identified sequence as part of a neoantigen region (in bold, Sequence ID 100 underlined) within Isoform 1 (SEQ ID NO. 83) of the fusion protein.

```
                                    (SEQ ID NO: 83)
MTASSSSDYGQTSKMSPRVPQQDWLSQPPARVTIKMECNPSQVNGSRN

SPDECSVAKGGKMVGSPDTVGMNYGSYMEEKHMPPPNMTTNERRVIV

PADPTLWSTDHVRQWLEWAVKEYGLPDVNILLFQNIDGKELCKMTKD

DFQRLTPSYNADILLSHLHYLRETPLPHLTSDDVDKALQNSPRLMHARN

TGGAAFIFPNTSVYPEATQRITTRPVSYR
```

Examination of additional amino acids on either side of RITTRPVSY (SEQ ID NO:100) revealed multiple sequence variations that retained TMPRSS2-ERG neoantigen specificity.

The region contained several TMPRSS2-ERG-Specific peptides measured by the three-tier test:

TABLE 14

Analysis of neoantigen region using Step3.V2

| HLA | SEQUENCE | Sequence ID | Lowest fold-difference from second and third tiers | Step3.V2 PASS or FAIL |
|---|---|---|---|---|
| A3, A11, B15 | RITTRPVSY | 100 | 7.88E+04 | PASS |
| A3 | ITTRPVSYR | 101 | 1.66E+03 | PASS |
| ND | RITTRPVSYR | 449 | 6.03E+05 | PASS |
| ND | QRITTRPVSY | 450 | 2.10E+03 | PASS |
| ND | QRITTRPVS | 1-9 of SEQ ID NO: 450 | 6.86E+01 | FAIL |
| ND | TQRITTRPV | 1-9 of SEQ ID NO: 451 | 9.13E+00 | FAIL |
| ND | TQRITTRPVSY | 451 | 2.16E+03 | PASS |
| ND | ATQRITTRPVS | 454 | 5.67E+01 | FAIL |
| ND | RITTRPV R | 455 | 0.00E+00 | FAIL |

ND = Not Determined

ITTRPVSYR (SEQ ID NO:101) had passed step two of epitope selection but was listed as failing Step 3.V1. A check of ITTRPVSYR (SEQ ID NO:101) was performed with NetMHC 4.0 (http://www.cbs.dtu.dk/services/NetMHC-4.0) as an independent resource. Also, the impact of expanding the core RITTRPVSY (SEQ ID NO:100) sequence length to 10- and 11 amino acids was screened using NetMHC 4.0. One or two amino acids were added on either end of the core sequence. Arginine (R) (RITTRPVSYR) (SEQ ID NO:449) was added at the C-terminus, R being the C-terminus of the fusion protein and we added glutamine (Q) (QRITTRPVSY) (SEQ ID NO:450) plus or minus threonine (TQRITTRPVSY) (SEQ ID NO:451) to the N-terminus and analyzed the sequence variations using NetMHC 4.0. Results indicated that RITTRPVSYR (SEQ ID NO:449) would also bind with a Core of either RITTRPVSY (SEQ ID NO:100), or RITTRPV_YR (SEQ ID NO:452). The space in SEQ ID NO: 452 indicates that serine can be absent with the remaining sequences still having a core sequence that binds. Also, the sequence was predicted to bind through a core of ITTRPVSYR (SE IQ NO:101), an epitope identified by step two and HP-TP-specific by Step 3.V2 but previously eliminated by Step 3.V1. We believe this was an error as the three-tier method is designed to be more stringent and sequences 100 and 101 are highly similar. Also, NetMHC 4.0 indicated that the decamer QRITTRPVSY (SEQ ID NO:450) could act as a core sequence from this region. Therefore, the amino acid sequence variations (all principally containing (R)ITTRPVSY) (SEQ ID NO:453) that qualify as HP-Ag (by Step 2 and Step 3.V2) within a 13 amino acid region of TMPRSS2-ERG are: RITTRPVSY (SEQ ID NO:100), ITTRPVSYR (SEQ ID NO:101), RITTRPVSYR (SEQ ID NO:449)), QRITTRPVSY (SEQ ID NO:450) and TQRITTRPVSY 9 SEQ ID NO:451).

Example 6: HP-Ag Peptides Homologous to Sequences within the Cancer Testis Antigen A-Kinase Anchor Protein 4 (AKAP4 (AKAP82, Cancer Testis Antigen 99)

Cancer germline antigen AKAP4 is highly restricted to the sperm's fibrous sheath. It is essential for sperm motility (Miki, Dev Biol 248:331 (2002)). However, AKAP 4 has been reported to be widely and stably expressed in several human cancers making it a cancer biomarker and a potential candidate for ACT. The potential of AKAP4 as a target for cancer diagnostics as well as cancer immunotherapy, including adoptive immunotherapy has been recognized by others (Chiriva-Internati et al. The Prostate 72(1):12-23 (2012); US 2012/0263757 A1; WO2014127006A1)), though not necessarily to target the C-RC nor with any delineation of specific peptide antigens or their qualification. Identification of specific peptide epitopes is particularly important for ACT since AKAP4 is part of a larger family of AKAPs expressed in adult tissues. For its use in HP-ACT, manipulation must be at the level of the T cell (the most direct and robust mode of immune manipulation). AKAP4 has to qualify as an HP-TP or Aux-TP (Step 1), and HP-Ag sequences must be identified and qualified for HP-ACT development (Steps 2-3).

Step 1. Qualification of AKAP4 as an HP-TP or Aux-TP
A. TP Frequency

In a survey of AKAP4 expression in breast cancer specimens, Saini et al. (Saini et al. PLoS One 8(2):e57095 (2013)) found the protein expressed in 85% of breast cancer specimens regardless of stage, type and grade of the tumor. AKAP4 was also found in 89% of ovarian cancer specimens regardless of stage (Agarwal et al. OncoImmunology 2(5): e24270 (2013)). Its expression has also been described in cervical (Agarwal et al. Int. J. Gynecol. Cancer 23(4):650-658 (2013)), prostate (Chiriva-Internati et al. The Prostate 72(1):12-23 (2012)) and possibly non-small cell lung cancers (Rhadi et al. J. Clin. Oncol. 31 suppl:abstr e18527 (2013)). AKAP4 protein has also been found in multiple myeloma (Chiriva-Internati et al. Br. J. Haematol. 140:464-474 (2008)). AKAP4's high frequency of expression, independent of stage in at least two cancers, and its presence in multiple cancers gives it a high frequency value.

B. TP Specificity

Although there are many forms of AKAPs functioning in normal tissues, normal AKAP4 expression is specific to the sperm's fibrous sheath. It is a highly conserved protein across species indicating a very specific and specialized normal function. In cancerous lesions, AKAP4 expression is restricted to the cancer cells of the tumor and is not observed in the surrounding cells (Agarwal et al. *OncoImmunology* 2(5):e24270 (2013)). Tight, conserved normal expression and highly delimited expression in cancer patients contribute to a high Specificity Value for AKAP4.

C. TP Functional Connectivity

What was known about AKAP4 and its similar family member AKAP110 was used to determine whether AKAP4 qualified as a cancer driver that could have a pivotal connection to the propagation of AKAP4+ cancers. As a class of proteins, AKAPs hold protein kinase (PKA), the principal intracellular receptor for cyclic AMP (cAMP) and other signaling molecules in proximity to specific substrates within the cell. In doing so they orchestrate PKA activity. It is known that the AKAPs govern subcellular targeting of PKA activity to specific cellular compartments and target substrates. They also bind additional signaling molecules. PKA has a multi-functional role in control of cell proliferation, survival and differentiation and is one of the most recognized drivers of carcinogenesis.

AKAPs tether the PKA holoenzyme (a coenzyme and an apoenzyme), which consists of two regulatory subunits (R) and two catalytic subunits (C). AKAP RI and RII classes differ in their sensitivity to cAMP, pattern of phosphorylation and subcellular localization. AKAP4 (AP85) is a member of the AKAP110 family. Like AKAP110, AKAP4 has sites for both RIα and RIIα. It is known that AKAP110, a slightly larger family member than AKAP4, has both cyclic AMP-dependent and cyclic AMP-independent mechanisms for PKA activation (Andreeva et al. *J. Molecular Signaling* 2:13-21 (2007)). Therefore neoexpression of AKAP4 in somatic cells likely provides more than one upstream mechanism (cAMP dependent and independent) to disrupt PKA control.

AKAP4 exhibits abundant and broadly localized expression within cancer cells both in vitro and in vivo. AKAP4 has been shown to associate with microtubules when artificially expressed in normal somatic cells (Nipper et al. *Biology of Reproduction* 75:189-196 (2006)) suggesting that it is be capable of a broad intracellular distribution when abnormally expressed. Distribution of AKAP4 within cervical cancer cells was associated with mitochondria, golgi, the cytoplasm, as well as surface expression. This further supports AKAP4's potential to disrupt normal control of PKA. Mutated PKA is one of the most well-recognized and well-characterized cancer drivers. However in the case of AKAP4 positive cancers, since the abnormality is upstream of PKA, PKA will no longer drive the cancer in the absence of AKAP4. Experimental evidence for this is that when AKAP4 is silenced in AKAP4 positive cervical cancer cells in vitro, they lose colony forming ability, this ability being a hallmark of regeneration-capable cells. In cervical cancer cells and cell lines, colony forming ability was consistently slightly greater than 50% in the cancer cells, supporting its action in an albeit substantial subpopulation of the cancer cells. AKAP4 expression in tumor specimens correlated well with PCNA, a marker of cell proliferation. Silencing of AKAP4 expression led to formation of small, slow growing tumors in mice with a fibrous morphology as opposed to those with active AKAP4 that exhibited small epithelial morphology with high PCNA staining. This lends further support to AKAP4's pivotal connection to the propagation of epithelial cancer. Cells within AKAP4+ cancers lacking AKAP4 will be incapable of propagating the cancer. AKAP4's restriction to cancer cells in vivo, as well as its stable expression across type and stage of a cancer supports its essential role.

There is recent clinical support to AKAP4's significance in lung cancer. Gumireddy et al. (Gumireddy et al. *Oncotarget* 6(19):1-11 (2015)). reported that of 116 cancer testis antigens screened for diagnostic potential in 264 non-small cell lung cancer (NSCLC) patients and 135 control patients, only AKAP4 predicted the presence, recurrence and progression of NSCLC Its presence in the blood could distinguish between patients with cancerous and benign lesions, detect recurrence of the cancer following surgery before a tumor was detected and predicted the subsequent development of metastatic disease.

In addition to data mining of AKAP4 biochemistry and PKA action in cancer, AKAP4's role in cancer regeneration, more specifically the C-RC, can be corroborated using in vitro techniques able to specifically select the C-RC population from human tumors for analysis and experimental manipulation.

AKAP4 qualified as an HP-TP for multiple cancer indications.

TABLE 15

Step 1 Calculation of AKAP4 HP-TP potential

| Candidate HP-TP | Frequency | Specificity | Functional Connectivity | Qualifies as an HP-TP? |
|---|---|---|---|---|
| AKAP4 | 14 | 4 | 6 | Yes |

Step 2. Identification of Candidate HP-Ag Sequences

Qualified as an HP-TP, AKAP4 advanced to Step 2 where the protein was analyzed for high probability T cell epitopes. The AKAP4 sequence used for epitope analysis:

(SEQ ID NO: 118)
MNRPQNLRLEMTAAKNTNNNQSPSAPPAKPPSTQRAVISPDGECSIDDLS

FYVNRLSSLVIQMAHKEIKEKLEGKSKCLHHSICPSPGNKERISPRTPAS

KIASEMAYEAVELTAAEMRGTGEESREGGQKSFLYSELSNKSKSGDKQMS

QRESKEFADSISKGLMVYANQVASDMMVSLMKTLKVHSSGKPIPASVVLK

RVLLRHTKEIVSDLIDSCMKNLHNITGVLMTDSDFVSAVKRNLFNQWKQN

ATDIMEAMLKRLVSALIGEEKETKSQSLSYASLKAGSHDPKCRNQSLEFS

TMKAEMKERDKGKMKSDPCKSLTSAEKVGEHILKEGLTIWNQKQGNSCKV

ATKACSNKDEKGEKINASTDSLAKDLIVSALKLIQYHLTQQTKGKDTCEE

DCPGSTMGYMAQSTQYEKCGGGQSAKALSVKQLESHRAPGPSTCQKENQH

LDSQKMDMSNIVLMLIQKLLNENPFKCEDPCEGENKCSEPRASKAASMSN

RSDKAEEQCQEHQELDCTSGMKQANGQFIDKLVESVMKLCLIMAKYSNDG

AALAELEEQAASANKPNFRGTRCIHSGAMPQNYQDSLGHEVIVNNQCSTN

SLQKQLQAVLQWIAASQFNVPMLYFMGDKDGQLEKLPQVSAKAAEKGYSV

GGLLQEVMKFAKERQPDEAVGKVARKQLLDWLLANL

A total of 678 overlapping 9 amino acid sequences (9mers) were screened using a comprehensive evaluation of antigenicity, chemistry, biochemistry, processing, and HLA binding. Five prevalent HLA A and HLA B types found in major world populations were screened for candidate epitopes and candidate sequences identified (Tables 16 and 17).

TABLE 16

Candidate HP-Ag sequences in AKAP4 with their HLA specificity

| Target | HLA Specificity | Core 9mer sequence | SEQ ID NO: |
|---|---|---|---|
| | A2 | YVNRLSSLV | 120 |
| | A2 | GLMVYANQV | 122 |
| | A2, B8 | VLLRHTKEI | 124 |
| | A2 | VLMTDSDFV | 125 |
| | A2 | AMLKRLVSA | 126 |
| | A2 | SLQKQLQAV | 130 |
| | A2 | GQLEKLPQV | 131 |
| | A2 | LLDWLLANL | 132 |
| | A2 | VASDMMVSL | 133 |
| | A2 | LIVSALKLI | 139 |
| | A2, B8 | ALKLIQYHL | 140 |
| | A2 | SVGGLLQEV | 151 |
| | A2 | LLQEVMKFA | 152 |
| | A3 | KQMSQRESK | 156 |
| | A3, A11 | MVSLMKTLK | 159 |
| | A3 | VVLKRVLLR | 161 |
| | A3 | VLKRVLLRH | 162 |
| | A3, A11 | QSLSYASLK | 163 |
| | A3, A11 | QSLEFSTMK | 164 |
| | A3, A11 | QVSAKAAEK | 171 |
| | A11 | VVLKRVLLR | 178 |
| | A11 | ASANKPNFR | 181 |
| | A3, A11 | QSPSAPPAK | 182 |
| AKAP4 | B7, A24 | RPQNLRLEM | 183 |
| | B7, A24 | KPPSTQRAV | 184 |
| | B7, B8, A24 | SPRTPASKI | 186 |
| | B7, A24 | CPGSTMGYM | 189 |

TABLE 16-continued

Candidate HP-Ag sequences in AKAP4 with their HLA specificity

| Target | HLA Specificity | Core 9mer sequence | SEQ ID NO: |
|---|---|---|---|
| | B7, A24 | LPQVSAKAA | 191 |
| | B15 | SQSLSYASL | 194 |
| | B8, B15 | LQKQLQAVL | 197 |
| | B15 | LQWIAASQF | 198 |
| | A3, A11 | VSALIGEEK | 276 |
| | A3, A11 | NASTDSLAK | 277 |
| | A3 | KDLIVSALK | 278 |
| | A3, A11 | QSAKALSVK | 279 |
| | A3 | KCSEPRASK | 280 |
| | A24 | VSAVKRNLF | 291 |
| | A24, B7 | EPRASKAAS | 293 |
| | B8 | SVVLKRVLL | 298 |
| | B8 | EKETKSQSL | 300 |
| | B8 | VGKVARKQL | 301 |
| | B15 | ILKEGLTIW | 303 |
| | B15 | KLIQYHLTQ | 304 |
| | B15 | GLLQEVMKF | 305 |

Step 3. Screen of Candidate HP-Ag Sequences for Specificity and Off-Target Potential The selected peptide sequences were then screened for peptide specificity and off target reactivity potential using a BLASTp screen employing parameters optimized for short sequence analysis and preference for minimal substitution and compositional adjustments as specificity for the intended target sequence is of utmost importance. Probability values for both On-target and Off-target returned results are then analyzed and a composite algorithm-generated value is used to determine an overall specificity rating. The greater the composite value the more specific the target sequence.

Candidate HP-Ag sequences that passed with high specificity and low off-target potential (66 sequences) were qualified as HP-Ag (Table 17).

TABLE 17

| HP-Ag sequences in AKAP4 | | | |
|---|---|---|---|
| Candidate HP sequence (HLA Specificity) | SEQ ID NO: | Specificity RatingAssessed Fold Difference between Specific | Qualified HP-Ag using Step 3 V.1? |
| SIDDLSFYV (A2) | 119 | 1.59E+03 | Yes |
| RLSSLVIQM (A2, A3, B15) | 121 | 1.28E+03 | Yes |
| MMVSLMKTL (A2, B8) | 123 | 8.40E+02 | Yes |
| KMDMSNIVL (A2) | 127 | 2.50E+03 | Yes |

TABLE 17-continued HP-Ag sequences in AKAP4

| Candidate HP sequence (HLA Specificity) | SEQ ID NO: | Specificity Rating Assessed Fold Difference between Specific | Qualified HP-Ag using Step 3 V.1? |
|---|---|---|---|
| VLMLIQKLL (A2, A24, B8) | 128 | 1.14E+03 | Yes |
| YQDSLGHEV (A2) | 129 | 5.63E+02 | Yes |
| LIDSCMKNL (A2) | 134 | 3.94E+03 | Yes |
| NLHNITGVL (A2, B8) | 135 | 2.65E+03 | Yes |
| IMEAMLKRL (A2) | 136 | 7.30E+02 | Yes |
| MLKRLVSAL (A2, B8, B15) | 137 | 1.52E+03 | Yes |
| KINASTDSL (A2) | 138 | 8.90E+02 | Yes |
| DMSNIVLML (A2) | 141 | 2.90E+03 | Yes |
| IVLMLIQKL (A2) | 142 | 5.00E+03 | Yes |
| LLNENPFKC (A2) | 143 | 1.63E+03 | Yes |
| FIDKLVESV (A2) | 144 | 7.00E+02 | Yes |
| KLVESVMKL (A2, A3, B15) | 145 | 1.73E+03 | Yes |
| QLQAVLQWI (A2) | 147 | 2.03E+03 | Yes |
| FMGDKDGQL (A2, B8) | 148 | 3.33E+03 | Yes |
| KLPQVSAKA (A2) | 149 | 2.55E+02 | No |
| KAAEKGYSV (A2, B8) | 150 | 9.00E+02 | Yes |
| SLVIQMAHK (A3, A11) | 153 | 3.80E+03 | Yes |
| SICPSPGNK (A3, A11) | 154 | 2.50E+03 | Yes |
| FLYSELSNK (A3, A11) | 155 | 6.75E+02 | Yes |
| KEFADSISK (A3) | 157 | 5.50E+02 | Yes |
| SISKGLMVY (A3, B15) | 158 | 1.75E+03 | Yes |
| TLKVHSSGK (A3, A11) | 160 | 1.62E+03 | Yes |
| HLTQQTKGK (A3) | 165 | 3.83E+03 | Yes |
| KCGGGQSAK (A3) | 166 | 1.42E+03 | Yes |
| NIVLMLIQK (A3, A11) | 167 | 1.90E+03 | Yes |
| KLLNENPFK (A3, A11) | 168 | 1.74E+03 | Yes |
| KLCLIMAKY (A3, B15) | 169 | 9.50E+03 | Yes |
| SQFNVPMLY (A3, A11, B15) | 170 | 1.60E+04 | Yes |
| FYVNRLSSL (A24, B8) | 172 | 1.19E+03 | Yes |
| KYSNDGAAL (A24) | 173 | 1.37E+03 | Yes |
| QFNVPMLYF (A24) | 174 | 1.88E+04 | Yes |
| IQMAHKEIK (A11) | 175 | 5.50E+03 | Yes |
| ISPRTPASK (A3, A11) | 176 | 5.93E+02 | Yes |
| KQMSQRESK (A3, A11) | 177 | 1.37E+03 | Yes |
| MAQSTQYEK (A11) | 179 | 1.37E+03 | Yes |
| ASMSNRSDK (A3, A11) | 180 | 2.12E+03 | Yes |
| PPSTQRAVI (A24, B7) | 185 | 5.20E+02 | Yes |

TABLE 17-continued

HP-Ag sequences in AKAP4

| Candidate HP sequence (HLA Specificity) | SEQ ID NO: | Specificity Rating Assessed Fold Difference between Specific | Qualified HP-Ag using Step 3 V.1? |
|---|---|---|---|
| KPIPASVVL (A24, B7) | 187 | 5.79E+02 | Yes |
| DPKCRNQSL (A24, B7, B8) | 188 | 7.50E+03 | Yes |
| MPQNYQDSL (A24, B7, B8) | 190 | 3.84E+03 | Yes |
| CSIDDLSFY (B15) | 192 | 4.56E+03 | Yes |
| ETKSQSLSY (B15) | 193 | 4.89E+03 | Yes |
| NQSLEFSTM (B15) | 195 | 4.56E+03 | Yes |
| GMKQANGQF (B15) | 196 | 5.16E+02 | Yes |
| PIPASVVLK (A3, A11) | 275 | 9.68E+02 | Yes |
| ELDCTSGMK (A3) | 281 | 9.83E+03 | Yes |
| QANGQFIDK (A3, A11) | 282 | 6.75E+03 | Yes |
| QCSTNSLQK (A3, A11) | 283 | 2.98E+03 | Yes |
| RQPDEAVGK (A3, A11) | 284 | 1.84E+03 | Yes |
| YSELSNKSK (A11) | 285 | 9.14E+02 | Yes |
| SDMMVSLMK (A11) | 286 | 1.70E+03 | Yes |
| TDIMEAMLK (A11) | 287 | 6.44E+02 | Yes |
| FSTMKAEMK (A11) | 288 | 5.73E+03 | Yes |
| GNSCKVATK (A11) | 289 | 1.19E+03 | Yes |
| EVMKFAKER (A11) | 290 | 8.35E+03 | Yes |
| APPAKPPST (A24, B7) | 292 | 1.96E+02 | Yes |
| MNRPQNLRL (B8) | 294 | 2.49E+03 | Yes |
| NLRLEMTAA (B8) | 295 | 2.24E+03 | Yes |
| DLSFYVNRL (B8) | 296 | 2.20E+03 | Yes |
| KLEGKSKCL (B8) | 297 | 1.19E+03 | Yes |
| EAMLKRLVS (B8) | 299 | 8.92E+02 | Yes |
| GVLMTDSDF (B15) | 302 | 1.69E+03 | Yes |

The epitopes identified as cancer-specific HP-TP using Step 3.V1 were re-evaluated using the more stringent and comprehensive Step 3.V2 method. Fifty eight of sixty-six epitopes passed using Step 3.V2. The eight remaining epitopes failed based on insufficient differences in off-target potential calculated in the comparison of the second and/or third tier results.

AKAP4 Epitopes Evaluated Using Third Step

TABLE 18

Three-tier Specificity Calculation

| HLA | SEQUENCE | Sequence ID | 1° Specificity PASS or FAIL | Lowest Fold-Difference from Second and Third Tiers | Final Result |
|---|---|---|---|---|---|
| A2 | SIDDLSFYV | 119 | PASS | 2.82E+03 | PASS |
| A2, A3, B15 | RLSSLVIQM | 121 | PASS | 4.71E+03 | PASS |

TABLE 18-continued

Three-tier Specificity Calculation

| HLA | SEQUENCE | Sequence ID | 1° Specificity PASS or FAIL | Lowest Fold-Difference from Second and Third Tiers | Final Result |
|---|---|---|---|---|---|
| A2, B8 | MMVSLMKTL | 123 | PASS | 1.50E+01 | FAIL |
| A2 | KMDMSNIVL | 127 | PASS | 7.26E+03 | PASS |
| A2, A24, B8 | VLMLIQKLL | 128 | PASS | 1.06E+03 | PASS |
| A2 | YQDSLGHEV | 129 | PASS | 1.60E+03 | PASS |
| A2 | LIDSCMKNL | 134 | PASS | 1.29E+04 | PASS |
| A2, B8 | NLHNITGVL | 135 | PASS | 4.70E+03 | PASS |
| A2 | IMEAMLKRL | 136 | PASS | 7.70E+02 | PASS |
| A2, B8. B15 | MLKRLVSAL | 137 | PASS | 1.53E+03 | PASS |
| A2 | KINASTDSL | 138 | PASS | 1.12E+03 | PASS |
| A2 | DMSNIVLML | 141 | PASS | 2.90E+03 | PASS |
| A2 | IVLMLIQKL | 142 | PASS | 3.53E+04 | PASS |
| A2 | LLNENPFKC | 143 | PASS | 2.80E+04 | PASS |
| A2 | FIDKLVESV | 144 | PASS | 3.30E+03 | PASS |
| A2, A3, B15 | KLVESVMKL | 145 | PASS | 4.70E+03 | PASS |
| A2 | QLQAVLQWI | 147 | PASS | 7.5 | FAIL |
| A2, B8 | FMGDKDGQL | 148 | PASS | 3.38E+04 | PASS |
| A2 | KLPQVSAKA | 149 | PASS | 559 | PASS |
| A2, B8 | KAAEKGYSV | 150 | PASS | 548 | PASS |
| A3, A11 | SLVIQMAHK | 153 | PASS | 2.70E+04 | PASS |
| A3, A11 | SICPSPGNK | 154 | PASS | 6.70E+03 | PASS |
| A3, A11 | FLYSELSNK | 155 | PASS | 9.57E+03 | PASS |
| A3 | KEFADSISK | 157 | PASS | 1.57E+03 | PASS |
| A3, B15 | SISKGLMVY | 158 | PASS | 2.79E+04 | PASS |
| A3, A11 | TLKVHSSGK | 160 | PASS | 1.14E+03 | PASS |
| A3 | HLTQQTKGK | 165 | PASS | 6.33E+03 | PASS |
| A3 | KCGGGQSAK | 166 | PASS | 7.38E+02 | PASS |
| A3, A11 | NIVLMLIQK | 167 | PASS | 3.67E+03 | PASS |
| A3, A11 | KLLNENPFK | 168 | PASS | 2.11E+03 | PASS |
| A3, B15 | KLCLIMAKY | 169 | PASS | 2.59E+04 | PASS |
| A3, B11, B15 | SQFNVPMLY | 170 | PASS | 2.59E+04 | PASS |
| A24, B8 | FYVNRLSSL | 172 | PASS | 1.57E+03 | PASS |
| A24 | KYSNDGAAL | 173 | PASS | 2.23E+03 | PASS |
| A24 | QFNVPLMYF | 174 | PASS | 1.51E+02 | FAIL |
| A11 | IQMAHKEIK | 175 | PASS | 7.59E+03 | PASS |
| A3, A11 | ISPRTPASK | 176 | PASS | 5.06E+02 | PASS |
| A3, A11 | KQMSQRESK | 177 | PASS | 7.52E+02 | PASS |

TABLE 18-continued

Three-tier Specificity Calculation

| HLA | SEQUENCE | Sequence ID | 1° Specificity PASS or FAIL | Lowest Fold-Difference from Second and Third Tiers | Final Result |
|---|---|---|---|---|---|
| A11 | MAQSTQYEK | 179 | PASS | 4.06E+02 | FAIL |
| A3, A11 | ASMSNRSDK | 180 | PASS | 6.33E+03 | PASS |
| A24, B7 | PPSTQRAVI | 185 | PASS | 5.33E+02 | PASS |
| A24, B7 | KPIPASVVL | 187 | PASS | 7.67E+02 | PASS |
| A24, B7, B8 | DPKCRNQSK | 188 | PASS | 1.25E+03 | PASS |
| A24, B7, B8 | MPQNYQDSL | 190 | PASS | 5.28E+03 | PASS |
| B15 | CSIDDLSFY | 192 | PASS | 5.28E+03 | PASS |
| B15 | ETKSQSLSY | 193 | PASS | 1.90E+02 | FAIL |
| B15 | NQSLEFSTM | 195 | PASS | 5.45E+03 | PASS |
| B15 | GMKQANGQF | 196 | PASS | 3.03E+04 | PASS |
| A3, A11 | PIPASVVLK | 275 | PASS | 1.57E+03 | PASS |
| A3 | ELDCTSGMK | 281 | PASS | 1.86E+04 | PASS |
| A3, A11 | QANGQFIDK | 282 | PASS | 1.07E+04 | PASS |
| A3, A11 | QCSTNSLQK | 283 | PASS | 4.70E+03 | PASS |
| A3, A11 | RQPDEAVGK | 284 | PASS | 2.07E+03 | PASS |
| A11 | YSELSNKSK | 285 | PASS | 1.10E+03 | PASS |
| A11 | SDMMVSLMK | 286 | PASS | 1.50E+01 | FAIL |
| A11 | TDIMEAMLK | 287 | PASS | 1.85E+03 | PASS |
| A11 | FSTMKAEMK | 288 | PASS | 5.28E+03 | PASS |
| A11 | GNSCKVATK | 289 | PASS | 5.04E+03 | PASS |
| A11 | EVMKFAKER | 290 | PASS | 3.17E+04 | PASS |
| A24, B7 | APPAKPPST | 292 | PASS | 9.30E+01 | FAIL |
| B8 | MNRPQNLRL | 294 | PASS | 7.47E+02 | PASS |
| B8 | NLRLEMTAA | 295 | PASS | 1.57E+03 | PASS |
| B8 | DLSFYVNRL | 296 | PASS | 9.41E+02 | PASS |
| B8 | KLEGKSKCL | 297 | PASS | 3.98E+03 | PASS |
| B8 | EAMLKRLVS | 299 | PASS | 7.70E+01 | FAIL |
| B15 | GVLMTDSDF | 302 | PASS | 1.45E+03 | PASS |

Example 7. The Derivation of HP-Ag Peptides Homologous to LUZP4 (HOM-TES-85) Sequences Expressed in Cancers The potential of LUZP4 (leucine zipper protein 4) as an HP-TP was evaluated using curated literature research as well as data from protein and genome databases. LUZP4 is a cancer testis antigen that was identified by screening a cDNA bank enriched for testis-specific transcripts with seminoma patient serum (Türeci et al. *Ongogene* 21(24): 3879-88 (2002)). LUZP4 is a novel member of the leucine zipper protein family, which is involved in DNA binding and gene transcription.

Step 1. Qualification of LUZP4 as an HP-TP or Aux-TP
A. TP Frequency
LUZP4 is expressed in a number of cancers including: primary breast cancer (47%, Mischo et al. *Int J Cancer* 118(3):696 (2006)) liver (19%, Lou et al. *Cancer Immun* 2:11 (2002)), malignant melanoma (36%), gliomas (35%), ovarian cancers (31%), seminomas (31%), lung cancer (28%), liver (19%, Lou), colorectal tumors (9.5%) (Tureci et al. *Ongogene* 21(24):3879-88 (2002)) and Head and Neck Squamous Cell Carcinoma (HNSCC, 4%, Atanackovic et al. Cancer Biol Ther 5(9):1218 (2006)). The level of expression of LUZP4 in a wide variety of cancers qualifies it as a TP in regard to frequency.

B. TP Specificity

HOM-TES-85, a cancer testis antigen, is tightly silenced in normal tissues except for testis as determined by RT-PCR and Northern blot hybridization studies (Tureci et al. Ongogene 21(24):3879-88 (2002)). In addition, resting and activated peripheral blood mononuclear cells do not express LUZP4 indicating that it does not represent a physiological proliferation antigen. The lack of LUZP4 expression in normal tissue while frequently activated in a number of different cancers gave HOM-TES-85 a positive specificity value.

C. TP Functional Connectivity

LUZP4 is a cancer testis antigen and a member of the family of leucine zipper proteins, which is involved in RNA export, DNA binding and gene transcription. Studies reveal that LUZP4 localizes to the nucleus where it could impact the spliceosome or alternatively part of the transcriptosome in tumor cells (Tureci et al. Ongogene 21(24):3879-88 (2002)). Studies by Viphakone et al. (Viphakone et al. Nucleic Acids Res 43(4):2353 (2015)) indicate that LUZP4 has two regions that are involved in mRNA binding. LUZP4 can act as a novel mRNA export adaptor for the TREX export pathway. The TREX complex consists of multiple proteins that, together, are a major mRNA export pathway that links transcription elongation to mRNA transport from the nucleus to the cytoplasm. Export of mRNA is often dysregulated in cancer and there is a close link between packaging and export of mRNA and genome stability. For example, the TREX complex is highly expressed in breast cancers and is believed to drive aggressive breast cancer, impacting both tumor size and metastatic state (Guo et al. Cancer Res. 65:3011 (2015)). LUZP4 enhances RNA binding activity of the RNA binding domain of nuclear RNA export factor 1 (Nxf1) enhancing its binding activity. Nxf1 works in conjunction with another TREX export factor Alyref. LUZP4 is believed to compete with the normal export factor Alyref.

Another consideration is possible transcriptional function of the leucine zipper region of LUZP4. The leucine zipper region of LUZP4 shows an atypical amphipathy with clusters of hydrophobic residues exclusively shared by N-Myc proto-oncogene. Sequence analysis of the zipper region suggests a means for involvement of LUZP4 in transcriptional processes. The leucine zipper region of Myc proteins determines sequence specific DNA binding and is essential for myc biology as a cancer driver. Given the similarities between the leucine zipper region of N-Myc and LUZP4, it is likely the LUZP4 leucine zipper region can fulfill a similar function when abnormally expressed.

LUZP4 is highly expressed in melanoma where it is required for growth of melanoma in vitro (Viphakone et al. Nucleic Acid Res 43(4):2353 (2015)). In LUZP4 expressing multiple myeloma cell lines, LUZP4 knockdown eliminates the colony forming ability of the stem cell-like side population and their drug resistant properties (Wen et al. Br J Haematol 166:711 (2014)).

Study of the transcriptional network architecture of different types of breast cancer revealed that LUZP4 is a high degree gene in all breast cancer networks but HER2-enriched (Anda-Jauregui, G. et al. Front. Physiol. 7:568 (2016)). It was noted by the authors that all other luminal and basal forms share a common basal progenitor. The aberrant expression of LUZP4, its potential to impact cancer-associated alterations of transcriptional or post-transcriptional processes, and demonstrated dependence on its expression for qualities associated with C-RC qualifies it as a HP-TP antigen.

TABLE 19

Step 1 Calculation of LUZP4's HP-TP potential

| Candidate HP-TP | Frequency | Specificity | Functional Connectivity | Qualifies as an HP-TP? |
|---|---|---|---|---|
| LUZP4 | 7 | 6 | 4 | Yes |

Step 2. Identification of Candidate HP-Ag Sequences
The LUZP4 sequence used was:

(SEQ ID NO: 455)
MASFRKLTLSEKVPPNHPSRKKVNFLDMSLDDIIIYKELEGTNAEEEKNK

RQNHSKKESPSRQQSKAHRHRHRRGYSRCRSNSEEGNHDKKPSQKPSGF

KSGQHPLNGQPLIEQEKCSDNYEAQAEKNQGQSEGNQHQSEGNPDKSE

ESQGQPEENHESERSRNHLERSLSQSDRSQGQLKRHHPQYERSHGQYKR

SHGQSERSHGHSERSHGHSERSHGHSERSHGHSKRSRSQGDLVDTQSDL

IATQRDLIATQKDLIATQRDLIATQRDLIVTQRDLVATERDLINQSGRS

HGQSERHQRYSTGKNTITT

A total of 313 overlapping 9 amino acid sequences were analyzed for each HLA type shown. The peptides were evaluated for HLA alleles: A2, A3, A11, A24, B7, B8 and B15. Candidate HP-Ag LUZP4 sequences with their HLA specificity are shown in Table 20.

Step 3. Screen of HP-Ag Specificity and Off-Target Potential

The selected peptide sequences were then screened for peptide specificity and off target reactivity potential using a BLASTp screen employing parameters optimized for short sequence analysis and preference for minimal substitution and compositional adjustments as specificity for the intended target sequence is of utmost importance. Probability values for both on-target and off-target returned results are then analyzed and a composite algorithm-generated value is used to determine an overall specificity rating. The greater the composite value the more specific the target sequence.

TABLE 20

Candidate HP-Ag LUZP4 sequences with their HLA specificity; HP-Ag sequences that passed specificity and off-target potential using Step 3 V.1.

| Candidate HP sequence (HLA Specificity) | SEQ ID NO: | Assessed Fold Difference between Specific Target and Non-Target | Qualified HP-Ag using Step3 V.1? |
|---|---|---|---|
| SLDDIIIYK (A2, A3, A11) | 310 | 1.02E+03 | Yes |
| IIYKELEGT (A2) | 311 | 2.45E+03 | Yes |
| KVNFLDMSL (A2) | 312 | 2.36E+03 | Yes |

TABLE 20-continued

Candidate HP-Ag LUZP4 sequences with their HLA specificity; HP-Ag sequences that passed specificity and off-target potential using Step 3 V.1.

| Candidate HP sequence (HLA Specificity) | SEQ ID NO: | Assessed Fold Difference between Specific Target and Non-Target | Qualified HP-Ag using Step3 V.1? |
|---|---|---|---|
| FLDMSLDDI (A2) | 313 | 9.45E+02 | Yes |
| LIVTQRDLV (A2) | 314 | 9.55E+02 | Yes |
| KVPPNHPSR (A3, A11) | 315 | 2.07E+03 | Yes |
| QLKRHHPQY (A3, B8, B15) | 316 | 1.13E+04 | Yes |
| NSEEGNHDK (A11) | 317 | 4.10E+03 | Yes |
| PSQKPSGFK (A11) | 318 | 1.89E+03 | Yes |
| GQPLIEQEK (A11) | 319 | 1.78E+03 | Yes |
| QSDLIATQR (A11) | 320 | 1.25E+03 | Yes |
| RYSTGKNTI (A24) | 321 | 3.05E+03 | Yes |
| MASFRKLTL (B7, B8) | 322 | 2.38E+03 | Yes |
| HPSRKKVNF (B7, B8) | 323 | 2.53E+03 | Yes |
| SPSRQQSKA (B7) | 324 | 1.03E+03 | Yes |
| KPSQKPSGF (B7, B8) | 325 | 9.30E+02 | Yes |
| HPLNGQPLI (B7) | 326 | 1.29E+03 | Yes |
| PSRKKVNFL (B8) | 327 | 1.64E+03 | Yes |
| RKKVNFLDM (B8) | 328 | 9.73E+03 | Yes |
| GFKSGQHPL (B8) | 329 | 5.52E+03 | Yes |
| IATQRDLIV (B8) | 330 | 1.32E+03 | Yes |
| RQQSKAHRH (B15) | 331 | 7.54E+03 | Yes |
| EQEKCSDNY (B15) | 332 | 9.30E+03 | Yes |
| GQSERSHGH (B15) | 333 | 3.08E+03 | Yes |
| TQRDLIATQ (B15) | 334 | 2.29E+03 | Yes |
| TQRDLIVTQ (B15) | 335 | 2.71E+03 | Yes |
| TQRDLVATE (B15) | 336 | 1.20E+03 | Yes |
| GQSERHQRY (B15) | 337 | 4.77E+03 | Yes |
| MSLDDIIIY (B15) | 338 | 4.35E+03 | Yes |

The epitopes identified as cancer-specific HP-TP using Step 3.V1 were re-evaluated using the more stringent and comprehensive three-tier Step 3.V2 method. Twenty-seven of the twenty-nine epitopes passed using Step 3.V2. The two remaining epitopes failed based on <500-fold differences in off-target potential when compared with second-tier and/or third-tier results.

LUZP4 Epitopes Evaluated Using Third Step

TABLE 21

Three-tier Specificity Calculation

| HLA | SEQUENCE | Sequence ID | 1° Specificity PASS or FAIL | Lowest Fold-Difference from Second and Third Tiers | Final Result |
|---|---|---|---|---|---|
| A2, A3, A11 | SLDDIIIYK | 310 | PASS | 1.52E+03 | PASS |
| A2 | IIYKELEGT | 311 | PASS | 2.57E+02 | FAIL |
| A2 | KVNFLDMSL | 312 | PASS | 1.82E+03 | PASS |
| A2 | FLDMSLDDI | 313 | PASS | 5.84E+02 | PASS |
| A2 | LIVTQRDLV | 314 | PASS | 3.00E+03 | PASS |
| A3, A11 | KVPPNHPSR | 315 | PASS | 3.33E+03 | PASS |
| A3, B8, B15 | QLKRHHPQY | 316 | PASS | 6.23E+02 | PASS |
| A11 | NSEEGNHDK | 317 | PASS | 4.98E+03 | PASS |
| A11 | PSQKPSGFK | 318 | PASS | 2.38E+03 | PASS |
| A11 | GQPLIEQEK | 319 | PASS | 2.60E+03 | PASS |
| A11 | QSDLIATQR | 320 | PASS | 2.07E+03 | PASS |
| A24 | RYSTGKNTI | 321 | PASS | 8.64E+03 | PASS |

TABLE 21-continued

Three-tier Specificity Calculation

| HLA | SEQUENCE | Sequence ID | 1° Specificity PASS or FAIL | Lowest Fold-Difference from Second and Third Tiers | Final Result |
|---|---|---|---|---|---|
| B7, B8 | MASFRKLTL | 322 | PASS | 2.53E+03 | PASS |
| B7, B8 | HPSRKKVNF | 323 | PASS | 3.04E+03 | PASS |
| B7 | SPSRQQSKA | 324 | PASS | 6.05E+02 | PASS |
| B7, B8 | KPSQKPSGF | 325 | PASS | 1.04E+03 | PASS |
| B7 | HPLNGQPLI | 326 | PASS | 2.11E+03 | PASS |
| B8 | PSRKKVNFL | 327 | PASS | 2.82E+03 | PASS |
| B8 | RKKVNFLDM | 328 | PASS | 1.81E+04 | PASS |
| B8 | GFKSGQHPL | 329 | PASS | 9.07E+03 | PASS |
| B8 | IATQRDLIV | 330 | PASS | 1.98E+03 | PASS |
| B15 | RQQSKAHRH | 331 | PASS | 4.36E+03 | PASS |
| B15 | EQEKCSDNY | 332 | PASS | 7.26E+03 | PASS |
| B15 | GQSERSHGH | 333 | PASS | 6.33E+03 | PASS |
| B15 | TQRDLIATQ | 334 | PASS | 1.38E+03 | PASS |
| B15 | TQRDLIVTQ | 335 | PASS | 9.57E+03 | PASS |
| B15 | TQRDLVA1E | 336 | PASS | 1.01E+03 | PASS |
| B15 | GQSERHQRY | 337 | PASS | 2.64E+03 | PASS |
| B15 | MSLDDIIIY | 338 | PASS | 3.77E+02 | FAIL |

Example 8. The Derivation of HP-Ag Peptides Homologous to the ETV6-NTRK3 Sequences Expressed in Cancers The potential of ETV6-NTRK3 as an HP-TP was evaluated using curated literature research as well as data from protein and genome databases. ETV6-NTRK3 is a translocation shared by several rare cancers: secretory carcinoma of the breast, mammary analogue secretory carcinoma of the salivary glands (MASC), infantile fibrosarcoma and congenital mesoblastic nephroma. With the exception of MASC, these cancers are primarily cancers of infants, children, and young adults. The primary modality used to treat ETV6-NTRK3 fusion cancers is surgery however this can result in amputations and other disfigurement, for example, mastectomy in a child as young as 3 years old with secretory breast carcinoma (Euhus et al. *Cancer Cell* 2:347 (2002)) or amputation of a limb to remove infantile fibrosarcoma. Axial congenital fibrosarcomas are considered more aggressive with a recurrence rate as high as 33% (Blocker et al. *J Pediatr Surg* 22:665 (1987)) with metastases occurring in 13.5% without further therapy beyond surgery. Therefore, further treatment is indicated for patients where complete surgical removal is not possible. Although radiation and chemotherapy are used with good overall survival, the use of toxic chemotherapy on young infants could have life-long effects. Survivors require close follow-up as side effects can occur months to years after the therapy. A safe, targeted T cell therapy would avoid the serious consequences of current treatment options.

Step 1. Qualification of ETV6-NTRK3 as an HP-TP or Aux-TP

A. TP Frequency

ETV6-NTRK3-driven cancer is rare but present in several types of cancer. The fusion protein is present in 0.15% of breast cancers approximately 3,500 diagnoses per year. Most of these patients represent secretory breast carcinoma where ETV6-NTRK3 is expressed in over 90% of the cancers. Secretory breast carcinoma has a distinctive histopathology. Over 90% of MASC tumors are caused by the ETV6-NTRK3 fusion protein. However MASC represents only about 29 cases of head and neck cancer per year in the US. ETV6-NTRK3 is expressed in two congenital cancers: infantile or congenital fibrosarcoma and congenital mesoblastic nephroma, which are considered closely related cancers (Adem et al. *Mod Pathol* 14:1246 (2001)). Childhood soft tissue sarcomas represent 1% of all newly diagnosed cancers (Dana Farber Cancer Institute) or an estimated 16,600 cases per year. Congenital fibrosarcomas represent approximately 10% of childhood soft tissue sarcomas (an estimated 1,660 cases), commonly located in the extremities (71%) (Blocker et al. *J Pediatr Surg* 22:665 (1987). Twenty-nine percent of congenital fibrosarcomas are axial where surgical removal is not always possible (Grier et al. Cancer 56:1507 (1985); Blocker et al. *J Pediatr Surg* 22:665 (1987). Infantile or congenital fibrosarcoma and congenital mesoblastic nephromas are distinguished from other soft tissue fibrosarcomas by the young age of the patient (diagnosed at birth to the first 3 months of life). In MASC, ETV6-NTRK3 cancers also have distinctive histopathology making genetic screening confirmative rather than needed for primary diagnosis (Skalova, *Head and Neck Pathology* 7:530 (2013)). Therefore, it is possible to identify patients with MASC based on presentation and histopathology. Although an HCP therapy would help patients with all types of ETV6-NTKR3-positive cancers, the feasibility of ETV6-NTRK3 as an HP-TP is primarily driven by the incidence and ability to identify and reach patients with secretory carcinoma of the breast, further supported by the congenital cancers.

B. TP Specificity

The ETV6 (ets variant 6) is an ETS family transcriptional repressor expressed in many normal tissues including lung, colon, heart and salivary gland (see web-based Proteomics DB. The native protein plays a role in hematopoiesis. It, in itself is not specific to cancer and therefore not a target for CTL therapy. NTRK3 (neurotrophic tyrosine kinase, receptor, type 3) protein is reported in the normal brain and retina (Proteomics DB). The normal protein is not specific to cancer and thus not a target for CTL therapy. The fusion of ETV6 and NTRK3 result in unique sequences within the junctional region that are specific for ETV6-NTRK3, an oncogenic protein present only in cancer.

C. TP Functional Connectivity

NTRK3 is a membrane-bound receptor that upon binding of neurotropin, phosphorylates itself and the RAS-MAP kinase (MAPK) mitogenic pathway activating cyclin Dl and the phosphatidyl inositol-3-kinase (PI3K)-AKT cell survival pathway. Fusion of ETV6 with NTRK3 creates a potent protein tyrosine kinase leading to constitutive activation of the two NTRK3-mediated pathways. Both are required for the transforming ability of ETV6-NTRK3 (Tognon et al. *Cancer Research* 61:8909 (2001)) causing aberrant cell cycle progression, disrupting the balance between this progression and apoptosis. Expression of ETV60NTRK3 has been shown to be the primary event in secretory breast carcinoma evidenced by the retroviral transfer of the fusion protein into murine mammary glands giving rise to secretory breast carcinoma (Tognon et al. *Cancer Cell* 2:367 (2002). Li et al. (Li et al. *Cancer Cell* 12:542 (2007)) found that activation of the fusion oncogene in mice by Wap-Cre leads to 100% penetration of multifocal, malignant breast cancer through activation of activator protein 1 (AP1) transcription factor complex. The target of this action was the bipotent luminal progenitor cells of the mammary gland, supporting a C-RC context. This evidence qualified the functional connectivity of ETV6-NTRK3.

ETV6-NTRK3 Met the Three Criteria and Therefore Qualified as an HP-TP.

TABLE 22

Step 1 Calculation of ETV6-NKRT3's HP-TP potential

| Candidate HP-TP | Frequency | Specificity | Functional Connectivity | Qualifies as an HP-TP? |
|---|---|---|---|---|
| ETV6-NKRT3 | 4 | 6 | 4 | Yes |

Step 2. Identification of Candidate HP-Ag Sequences

The ETV6-NTRK3 sequences used to identify high probability candidate HP-Ag were:

(SEQ ID NO: 339)
VSPPEEHAMPIGRIADVQHIKRRDIVLKRELGEGAFGKVFLA and (SEQ ID NO: 340)
LDAGPDTVVIGMTRIPVIENPQYFRQGHNCHKPDTYVQHIKRRDIVLKR

ELGEGAF

Overlapping 9 amino acid sequences were analyzed for each HLA type shown. The peptides were evaluated for HLA alleles: A2, A3, A11, A24, B7, B8 and B15. Candidate HP-Ag sequences in ETV6-NTRK3 with their HLA specificity are shown in Tables 23 and 24.

TABLE 23

Candidate HP-Ag sequences in ETV6-NTRK3 with their HLA specificity

| Target | HLA Specificity | Core 9mer sequence | SEQ ID NO: |
|---|---|---|---|
| | A3, A11 | RIADVQHIK | 343 |
| | A3, A11 | ELGEGAFGK | 344 |
| | B7, B8 | MPIGRIADV | 350 |
| | B8 | VQHIKRRDI | 353 |

Step 3. Screen of HP-Ag Specificity and Off-Target Potential

The selected peptide sequences were then screened for peptide specificity and off target reactivity potential using a BLASTp screen employing parameters optimized for short sequence analysis and preference for minimal substitution and compositional adjustments as specificity for the intended target sequence is of utmost importance. Probability values for both on-target and off-target returned results are then analyzed and an algorithm-generated value is used to determine an overall specificity rating (Step 3 V.1). The greater the composite value the more specific the target sequence.

TABLE 24

HP-Ag sequences that passed specificity and off-target potential using the Step 3 V.1 method.

| Candidate HP sequence (HLA Specificity) | SEQ ID NO: | Specificity Rating (Fold Difference between Specific Target and Non-Target) | Qualified HP-Ag? |
|---|---|---|---|
| GAFGKVFLA (A2) | 341 | 1.49E+01 | No |
| VIGMTRIPV (A2) | 342 | 4.49E+03 | Yes |
| VIENPQYFR (A3, A11) | 345 | 5.81E+03 | Yes |
| DTYVQHIKR (A11) | 346 | 6.53E+03 | Yes |
| IGMTRIPVI (A24, B8) | 347 | 7.19E+02 | Yes |
| PVIENPQYF (A24) | 348 | 3.29E+03 | Yes |
| PPEEHAMPI (B7) | 349 | 5.63E+03 | Yes |
| KPDTYVQHI (B7) | 351 | 2.35E+03 | Yes |
| HIKRRDIVL (B7, B8) | 352 | 5.59E+03 | Yes |

The epitopes identified as cancer-specific HP-TP using Step 3.V1 were re-evaluated using the more stringent and comprehensive three-tier Step 3.V2 method. Three epitopes identified in Step 2 were missing from the Step 3.V1 table: RIADVQHIKR, ELGEGAFGK and VIENPQYFR. The thirteen HP-Ag candidates from Table 23 were assessed using the three-tier Step 3.V2 method. The data is shown in Table 25.

TABLE 25

Epitopes identified in step 3.V2

| HLA | SEQUENCE | Sequence ID | 1° Specificity PASS or FAIL | Lowest Fold-Difference from Second and Third Tiers | Step 3.V2 PASS or FAIL |
|---|---|---|---|---|---|
| A2 | GAFGKVFLA | 341 | FAIL | | |
| A2 | VIGMTRIPV | 342 | FAIL | | |
| A3, A11 | RIADVQHIK | 343 | PASS | 8.00E+02 | PASS |
| A3, A11 | ELGEGAFGK | 344 | FAIL | | |
| A3, A11 | VIENPQYFR | 345 | FAIL | | |
| A11 | DTYVQHIKR | 346 | FAIL | | |
| A24, B8 | IGMTRIPVI | 347 | FAIL | | |
| A24 | PVIENPQYF | 348 | FAIL | | |
| B7 | PPEEHAMPI | 349 | FAIL | | |
| B7, B8 | MPIGRIADV | 350 | PASS | 1.13E+01 | FAIL |
| B7 | KPDTYVQHI | 351 | FAIL | | |
| B7, B8 | HIKRRDIVL | 352 | FAIL | | |
| B8 | VQHIKRRDI | 353 | FAIL | | |

The sequence RIADVQHIK (Seq ID 343) with an HLA specificity of A3 and A11 was determined to be an ETV6-NKRK3-specific HP-TP suitable for HP-ACT.

Example 9. The Derivation of AuxP-Ag Peptides Homologous to LY6K Sequences Expressed in Cancers The potential of LY6K (lymphocyte antigen 6 complex, locus K) as an HP-TP was evaluated using curated literature research as well as data from protein and genome databases. LY6K is a cancer-testis antigen that belongs to the LY6 superfamily. LY6K shows a high homology to the low-molecular weight GPI-anchored molecule.

Step 1. Qualification of LY6K as an HP-TP or Aux-TP

A. TP Frequency

LY6K is expressed in 85% of gastric cancers (Ishikawa H et. al. *Gastric Cancer*. (1):173-80 (2014)), 88.2% of NSCLC and 95.1% of ESCC (Ishikawa N et. al. *Cancer Res*. 67(24): 11601-11 (2007)). The overexpression of LY6K has also been documented in a number of cancers including: gingivobuccal complex (GBC) cancers (Ambatipudi et. al., *Genes Chromosomes Cancer.* 51(2): 161-173. (2012)), breast cancer (Lee J et. al. *Oncol. Rep.* 16, 1211-1214 (2006)), bladder cancer (Matsuda R. *Br. J. Cancer* 104, 376-386 (2011)), and head and neck squamous cell carcinoma (de Nooij-van Dalen et. al. *Int J Cancer*. March 1; 103(6):768-74 (2003)). LY6K expression in 85% of gastric cancers as well as other cancers met the criteria for TP Frequency.

B. TP Specificity

LY6K is considered a cancer testis antigen. There are some discrepancies in reported protein expression in normal tissues using the available protein databases. Proteomics DB reports expression in the rectum and to a lesser extent, the ovaries while the Human Proteome Map from the Human Proteome Project reports no expression in any tissues other than the testis and ovaries. The Human Protein Atlas, although somewhat less reliable based on immunohistochemical localization in tumor samples, reports labeling only in the testis. A check of gene expression using GTex analysis shows very low level to no gene expression in all tissues but the testis.

Neo-expression of LY6K in multiple cancers has led to its proposed use as a serologic biomarker for lung and esophageal cancers (Ishikawa et al., *Cancer Res* 67:11601 (2007)). LY6K peptides are also being tested as a component in multi-peptide cancer vaccines for esophageal cancer (Kono e al. *J Translational Medicine* 10:141 (2012) and gastric cancer (Ishikawa et al. *Gastric Cancer* 17:173 (2014); Higashihara et al. *Int J Oncology* 44:662 (2014)). However, to our knowledge, no one has proposed or described the use of LY6K epitopes to design CTL-based therapy. LY6K was given a positive specificity value based on 1) Lack of LY6K protein expression in normal tissues other than testis and possibly the ovaries, supported by multiple databases, and 2) the fact that it is frequently newly expressed in a number of cancers, resulted in a positive value for cancer specificity.

C. TP Functional Connectivity

LY6K is a GPI-anchored protein. In sperm it is associated with testis-expressed gene 101 (TEX101). Together, these proteins are required for sperm migration into the oviduct (Fujihara et al. *Biology of Reproduction* 90:60 (2014)). The abnormal action of LY6K is associated a gain of function mutation. It lies in close proximity to other known oncogenes like MYC. Transfection of bladder cancer cells with LY6K enhances cell migration, invasion into extracellular matrix (Matrigel) and cell proliferation. Conversely, knock out of LY6K results in decreased ability to migrate and invade Matrigel with reduced proliferation (Matsuda et al. *Br. J. Cancer* 104; 376 (2011)). This is consistent with normal actions of LY6K in the enabling of sperm to migrate into the oviduct. Human LY6K belongs to the LY-6.urokinase-type plasminogen activator receptor (UPAR) superfamily. The urokinase system is involved in tissue remodeling and is associated with cancer spread through matrix turnover, ability to invade tissue stroma and migrate, enabled proliferation, apoptosis and angiogenesis (Hildebrand and Schaaf *Int. J. Oncology* 34:15 (2008)). Activating protein-1 (AP-1) transcription factors JunD and Fra-1 induce invasion and metastasis of breast cancer cells by increasing LY6K gene expression and the activation of Raf-1/MEK/ERK signaling pathway and up-regulation of matrix metalloproteases. (Kong et al. *J Biol Chem* 287:38889 (2012)). Therefore, the action of LY6K is to enable tumor growth and metastasis by supporting tissue remodeling and cell invasion. Its actions will be downstream of the pivotal changes in the cancer that will induce AP-1 transcription factors. Therefore LY6K is not an HP-TP but is rather an enabling Aux-TP.

TABLE 26

Step 1 Calculation of LY6K's HP-TP potential

| Candidate HP-TP | Frequency | Specificity | Functional Connectivity | Qualifies as an HP-TP? |
|---|---|---|---|---|
| LY6K | 20 | 6 | −4 | No as HP-TP; Yes, as Aux-TP |

Aux-TPs can serve as useful second or companion targets in an HP-ACT therapy, particularly in advanced cancer with active metastases.

Step 2. Identification of Candidate HP-Ag Sequences

Candidate HP-Ag sequences in LY6K with their HLA specificity are shown in Tables 26 and 27.

TABLE 26

Candidate HP-Ag sequences in LY6K with their HLA specificity

| Target | HLA Specificity | Core 9mer sequence | SEQ ID NO: |
|---|---|---|---|
| LY6K | A2 | GTMALLALL | 366 |
|  | A2 | MALLALLLV | 367 |
|  | A2 | ALLALLLVV | 368 |
|  | A2 | AILLLLASI | 374 |
|  | A2 | ILLLLASIA | 375 |
|  | A2 | LLLLASIAA | 376 |
|  | A2 | LLASIAAGL | 377 |
|  | A2, B8 | LALLLVVAL | 379 |
|  | A3, A11 | LLLVVALPR | 381 |
|  | B7 | APLGTMALL | 391 |
|  | B15 | CVIAAVKIF | 393 |

Step 3. Screen of HP-Ag Specificity and Off-Target Potential

The selected peptide sequences were then screened for peptide specificity and off target reactivity potential using a BLASTp screen employing the method of

| Candidate HP sequence (HLA Specificity) | SEQ ID NO: | Specificity Rating (Fold Difference between Specific Target and Non-Target) | Qualified HP-Ag? |
|---|---|---|---|
| LLVVALPRV (A2) | 369 | 1.05E+3003 | Yes |
| FMVAKQCSA (A2) | 370 | 1.54E+3004 | Yes |
| SMGESCGGL (A2) | 371 | 2.12E+3003 | Yes |
| GLWLAILLL (A2) | 372 | 7.07E+3002 | Yes |
| FLLEEPMPF (A2, B15) | 378 | 9.66E+3003 | Yes |
| KIFPRFFMV (A3) | 380 | 2.26E+3004 | Yes |
| RVWCHVCER (A3, A11) | 382 | 3.96E+3004 | Yes |
| NTFECQNPR (A11) | 383 | 1.34E+3004 | Yes |
| KWTEPYCVI (A24) | 384 | 4.10E+3004 | Yes |
| AAVKIFPRF (A24) | 385 | 1.78E+3003 | Yes |
| LWLAILLLL (A24) | 386 | 8.94E+3002 | Yes |
| APRADPPWA (B7) | 387 | 3.40E+3003 | Yes |
| RADPPWAPL (B7) | 388 | 9.60E+3002 | Yes |
| PPWAPLGTM (B7) | 389 | 1.21E+3004 | Yes |
| WAPLGTMAL (B7) | 390 | 3.58E+3003 | Yes |
| CCKIRYCNL (B8) | 392 | 4.02E+3004 | Yes |
| AVKIFPRFF (B15) | 394 | 3.19E+3003 | Yes |
| KQCSAGCAA (B15) | 395 | 1.76E+3003 | Yes |
| LLEEPMPFF (B15) | 396 | 1.34E+3004 | Yes |
| YLKCCKIRY (B15) | 397 | 1.49E+3004 | Yes |

Step 3 V.1. Probability values for both On-target and Off-target algorithm-generated value was used to determine an overall specificity rating. The greater the composite value the more specific the target sequence.

Table 27. HP-Ag Sequences that Passed Step 3 V.1.

Candidate sequences analyzed in Table 27 using the method of Step 3.V1 were re-assessed using the more stringent and comprehensive method of Step 3.V2. LY6K Epitopes Evaluated Using Third Step

TABLE 28

Three-tier Specificity Calculation

| HLA | SEQUENCE | Sequence ID | 1° Specificity PASS or FAIL | Lowest Fold-Difference from Second and Third Tiers | Final Result |
|---|---|---|---|---|---|
| A2 | GTMALLALL | 366 | PASS | 7.19E+01 | FAIL |
| A2 | MALLALLLV | 367 | PASS | 3.90E+02 | FAIL |
| A2 | ALLALLLVV | 368 | PASS | 9.53E+01 | FAIL |
| A2 | LLVVALPRV | 369 | PASS | 1.03E+03 | PASS |
| A2, A3 | KIFPRFFMV | 380 | PASS | 1.34E+05 | PASS |
| A2 | FMVAKQCSA | 370 | PASS | 6.90E+04 | PASS |
| A2 | SMGESCGGL | 371 | PASS | 2.95E+03 | PASS |
| A2 | GLWLAILLL | 372 | PASS | 3.50E+02 | FAIL |
| A2 | WLAILLLLA | 396 | PASS | 6.16E+02 | PASS |
| A2 | AILLLLASI | 374 | PASS | 1.01E+02 | FAIL |
| A2 | ILLLLASIA | 375 | PASS | 2.30E+01 | FAIL |
| A2 | LLLLASIAA | 376 | PASS | 6.75E+01 | FAIL |
| A2 | LLASIAAGL | 377 | PASS | 5.24E+02 | PASS |
| A2 | LALLLVVAL | 379 | PASS | 1.43E+03 | PASS |
| A2 | FLLEEPMPF | 378 | PASS | 4.71E+04 | PASS |
| A3, A11 | LLLVVALPR | 381 | PASS | 1.87E+02 | FAIL |
| A3, A11 | RVWCHVCER | 382 | PASS | 3.08E+04 | PASS |
| A11 | NTFECQNPR | 383 | PASS | 3.94E+05 | PASS |
| A24 | KWTEPYCVI | 384 | PASS | 4.05E+04 | PASS |
| A24 | AAVKIFPRF | 385 | PASS | 7.13E+02 | PASS |
| A24 | LWLAILLLL | 386 | PASS | 1.62E+03 | PASS |
| B7 | APRADPPWA | 387 | PASS | 8.47E+03 | PASS |
| B7 | RADPPWAPL | 388 | PASS | 4.00E+03 | PASS |
| B7 | PPWAPLGTM | 389 | PASS | 8.10E+03 | PASS |
| B7 | WAPLGTMAL | 390 | PASS | 2.42E+03 | PASS |
| B7 | APLGTMALL | 391 | PASS | 5.24E+02 | PASS |
| B8 | CCKIRYCNL | 392 | PASS | 1.29E+05 | PASS |
| B15 | CVIAAVKIF | 393 | PASS | 1.70E+04 | PASS |
| B15 | AVKIFPRFF | 394 | PASS | 2.23E+04 | PASS |
| B15 | KQCSAGCAA | 395 | PASS | 9.19E+03 | PASS |
| B15 | LLEEPMPFF | 396 | PASS | 1.57E+04 | PASS |
| B15 | YLKCCKIRY | 397 | PASS | 1.23E+05 | PASS |

Twenty-eight out of thirty-six sequences passing Step 3.V1 passed the more stringent and comprehensive Step 3.V2 test for off-target potential. The eight remaining sequences failed due to <500-fold difference in off-target potential.

Example 10. The Ability of Core High Probability 9Mers of Step 2 to Identify Suitable Epitopes of Varied Length Historically, T cell antigens described by others have been of varying lengths. When working with short protein sequences, such as a relatively short fusion region created by a translocation or the unique portion of a protein that is a member of a large, related family, it is desirable to identify as many specific antigenic High Probability (HP) peptides as possible. Although a 9 amino acid sequence (9mer) is the natural sequence length for HLA binding, peptides of 8, 10, and 11 amino acids (8mer, 10mer and 11mer respectively) can also bind the HLA cleft and serve as T cell antigens. However, comprehensive data is scarce for peptides of lengths beyond the standard 9mer. Therefore we wanted to 1) determine if the HP 9mer core peptides were the best configuration in most instances and 2) if they would predict feasible alternative peptides of 8. 1. Or 11 amino acids. We tested the ability of HLA A2 core 9mer sequences of the TMPRSS2-ERG fusion region identified by Step 2 to select suitable peptides of differing lengths that could be HP cytotoxic T cell antigens. Step 2 had identified 6 HP 9mer epitopes within the fusion region out of a possible 212 overlapping peptide sequences.

Studies were first conducted to determine if the characteristics of any of the six 9mer peptides would be improved by either subtracting one amino acid on either end to form an 8mer or adding 1 or 2 amino acids on either end to form 10mers and 11mers. The resulting peptide sequences were analyzed for changes in affinity to HLA-A2 (NetMHC 3.4, Nielsen et al. *Protein Sci.*, 12:1007-17 (2003)) and peptide processing (IEDB, Tenzer et al. *Cell Mol Life Sci.* 62:1025-1037 (2005)).

In this case, addition or subtraction of amino acids on the C and N terminal ends resulted in a significant decrease in predicted affinity compared to the HP 9mer core sequences, with only slight improvements in processing in some instances (Table 1). Therefore, targeting the 9mer core is the preferred method to identify T cell antigens.

TABLE 29

Comparison of TMPRSS2-ERG HLA A2 HP 9mer core peptides (bold) and associated sequences of differing lengths.

| | SEQ ID NO: | Affinity (Kd, nM) | Processing Score |
|---|---|---|---|
| WLSQPPAR | 398 | 18192 | 1.68 |
| LSQPPARV | 399 | 21095 | 1.16 |
| WLSQPPARV | 84 | 161 | 1.11 |
| DWLSQPPARV | 400 | 24043 | 1.13 |
| WLSQPPARVT | 401 | 16544 | 0.47 |
| QDWLSQPPARV | 402 | 18934 | 1.1 |
| DWLSQPPARVT | 403 | 24991 | 0.5 |
| WLSQPPARVTI | 404 | 1430 | 1.64 |
| KMECNPSQ | 405 | 23287 | 0.92 |
| MECNPSQV | 406 | 23020 | 1.16 |
| KMECNPSQV | 89 | 463 | 1.19 |
| IKMECNPSQV | 407 | 5912 | 1.22 |
| KMECNPSQVN | 408 | 29989 | 0.5 |
| TIKMECNPSQV | 409 | 14816 | 1.22 |
| IKMECNPSQVN | 410 | 27187 | 0.52 |
| KMECNPSQVNG | 411 | 19841 | 0.45 |
| KMVGSPDT | 412 | 9448 | 0.44 |
| MVGSPDTV | 413 | 2352 | 1.43 |
| KMVGSPDTV | 85 | 56 | 1.5 |
| GKMVGSPDTV | 414 | 11012 | 1.34 |
| KMVGSPDTVG | 415 | 16040 | 0.55 |
| GGKMVGSPDTV | 416 | 25046 | 1.23 |
| GKMVGSPDTVG | 417 | 29682 | 0.39 |
| KMVGSPDTVGM | 418 | 930 | 1.5 |
| VIVPADPT | 419 | 11852 | 0.15 |
| IVPADPTL | 420 | 7954 | 2.06 |
| VIVPADPTL | 86 | 1103 | 2.15 |
| RVIVPADPTL | 421 | 4482 | 2.23 |
| VIVPADPTLW | 422 | 24055 | 2 |
| RRVIVPADPTL | 423 | 15915 | 2.13 |
| RVIVPADPTLW | 424 | 23908 | 2.08 |
| VIVPADPTLWS | 425 | 14849 | 0.37 |
| GLPDVNIL | 426 | 960 | 1.75 |
| LPDVNILL | 427 | 22931 | 1.79 |
| GLPDVNILL | 87 | 14 | 1.91 |
| YGLPDVNILL | 428 | 1141 | 1.82 |
| GLPDVNILLF | 429 | 2887 | 2.24 |
| EYGLPDVNILL | 430 | 22786 | 2.01 |
| YGLPDVNILLF | 431 | 8393 | 2.15 |
| GLPDVNILLFQ | 432 | 5778 | 1.03 |
| ILLSHLHY | 433 | 4623 | 2.47 |
| LLSHLHYL | 434 | 179 | 1.82 |
| ILLSHLHYL | 88 | 3 | 1.77 |
| DILLSHLHYL | 435 | 2148 | 1.8 |
| ILLSHLHYLR | 436 | 1732 | 1.66 |
| ADILLSHLHYL | 437 | 9940 | 1.82 |
| DILLSHLHYLR | 438 | 28058 | 1.69 |
| ILLSHLHYLRE | 439 | 11054 | 0.31 |

Studies were then conducted to examine whether HP 9mer core peptides derived from Step 2, would identify HP epitopes of varied lengths. We surveyed the fusion region identified in Example using NetMHC 4.0 (Andreatta et al. *Bioinformatics* (2015)—epublished ahead of print Nov. 13, 2015), which reports a core sequence based on sequence alignment for a given allele, rank and N terminal binding for peptides of 8-11 amino acids, trained on IEDB MHC Class I affinity measurements. We found that 9mer sequences identified for HLA A2 were contained in the 8mer (1 of 2), 10mer (2 of 3) and 11mer (2 of 2) peptides identified by NetMHC 4.0 using the authors' preset parameters. One 8mer, FIFPNTSV (SEQ ID NO:440) and one 10mer, YLRETPLPHL (SEQ ID NO:441), powered by calculated affinity, did not contain an HP 9mer core peptide. Processing and affinity scores for FIFPNTSV (SEQ ID NO:440) and YLRETPLPHL SEQ ID NO:441) fit within the range exhibited by the HP-9mer core peptides, qualified based on the comprehensive set of Step 2 parameters. Therefore, although data is scarce for peptides of varied lengths beyond 9 amino acids, comparison with the 9 mer core values can be used to corroborate the utility of epitopes of varying lengths. Both FIFPNTSV (SEQ ID NO:440) and YLRETPLPHL SEQ ID NO:441) would likely perform as additional HP epitopes for the TMPRSS2-ERG fusion region as they compare favorably to the range established by the six HP 9mer antigens, for example, in processing and affinity

TABLE 30

Comparison of sample values between 9mer core sequences and epitopes of varying length identified by NetMHC 4.0

| HP core sequences | SEQ ID NO: | Processing Score | Affinity (Kd, nM) |
|---|---|---|---|
| WLSQPPARV | 84 | 1.11 | 161 |
| KMECNPSQV | 89 | 1.19 | 463 |
| KMVGSPDTV | 85 | 1.5 | 56 |
| VIVPADPTL | 86 | 2.15 | 1103 |
| GLPDVNILL | 87 | 1.91 | 14 |
| ILLSHLHYL | 88 | 1.77 | 3 |
| Sequences identified only by Net MHC 4.0, corroborated using 9mer core data | | | |
| FIFPNTSV | 440 | 1.14 | 118 |
| YLRETPLPHL | 441 | 1.99 | 34 |

The ability of the 9mer core to predict epitopes of varying lengths in a longer sequence was tested, AKAP4 consisting of a total of 678 overlapping 9 amino acid sequences. We used NetMHC 4.0 under its preset parameters to identify binding peptides for overlapping sequences of 8-11 amino acids. As shown in Table 30, core HLA A2 AKAP4 9mers identified by this method were shared in all but one 10mer sequence SLAKDLIVSA (SEQ ID NO: 269) identified by NetMHC 4.0 as a peptide capable of binding HLA A2.

TABLE 31

Comparison of core HLA A2 AKAP4 sequences identified by various methods

| NetMHC 4.0 High affinity 8mer | Step 2 Qualified HP 9mer core | NetMHC 4.0 High affinity 10mer | NetMHC 4.0 High affinity 11mer |
|---|---|---|---|
| IDDLSFYV (SEQ ID NO: 442) | SIDDLSFYV (SEQ ID NO: 119) | CSIDDLSFYV (SEQ ID NO: 443) | ECSIDDLSFYV (SEQ ID NO: 270) |
| | | SIDDLSFYVN (SEQ ID NO: 444) | |
| | GLMVYANQV (SEQ ID NO: 122) | KGLMVYANQV (SEQ ID NO: 445) | |
| MMVSLMKTL (SEQ ID NOI: 123) | | | MMVSLMKTLKV (SEQ ID NO: 306) |
| VLMTDSDFV (SEQ ID NOI: 125) | | GVLMTDSDFV (SEQ ID NO: 446) | LMTDSDFVSAV (SEQ ID NO: 307) |
| | | VLMTDSDFVS (SEQ ID NO: 447) | |
| AMLKRLVSA (SEQ ID NO126) | | AMLKRLVSAL (SEQ ID NO: 137) | |
| KMDMSNIVL (SEQ ID NO: 127) | | KMDMSNIVLM (SEQ ID NO: 448) | |
| | | MDMSNIVLML (SEQ ID NO: 274) | |
| FIDKLVESV (SEQ ID NO: 144) | | QFIDKLVESV (SEQ ID NO: 273) | |
| KLVESVMKL (SEQ ID NO: 145) | | DKLVESVMKL (SEQ ID NO: 272) | |
| LLQEVMKFA (SEQ ID NO: 152) | | GLLQEVMKFA (SEQ ID NO: 305) | |
| LLDWLLANL (SEQ ID NO: 132) | | QLLDWLLANL (SEQ ID NO: 271) | KQLLDWLLANL (SEQ ID NO: 308) |

Since affinity is only one aspect of an effective T cell antigen, the novel peptide was qualified by comparing calculable 10mer values to the HP core sequences that identified NetMHC 4.0-positive sequences. A comparison on processing scores and affinities are provided in Table 31 as an example. It should be noted that in this larger sequence, Step 2 identified additional 9mers not identified by NetMHC 4.0's preset parameters, creating the possibility of further expanding the pool of epitope candidates based on a range established using the 9mer core peptides.

TABLE 32

Comparison of processing scores and affinities of HP 9 mer core sequences

| Identifying HP 9mer core sequences | SEQ ID NO: | Processing Score | Affinity (Kd, nM) |
|---|---|---|---|
| SIDDLSFYV | 119 | 1.07 | 3 |
| GLMVYANQV | 122 | 1.22 | 18 |
| MMVSLMKTL | 123 | 2.17 | 75 |
| VLMTDSDFV | 125 | 1.23 | 5 |
| AMLKRLVSA | 126 | 1.04 | 52 |
| KMDMSNIVL |  | 2.07 | 61 |
| FIDKLVESV | 144 | 1.04 | 13 |
| KLVESVMKL | 145 | 1.89 | 10 |
| LLQEVMKFA | 152 | 0.98 | 121 |
| LLDWLLANL | 132 | 1.8 | 19 |
| Sequence identified only by Net MHC 4.0 affinity prediction |  |  |  |
| SLAKDLIVSA | 269 | 1.11 | 98 |

The 9 mer core sequences were highly predictive of high affinity T cell antigens having varying numbers of amino acids. Also, the use of HP 9mer ranges established for HLA-A2 could serve as a metric to corroborate the HP potential of epitopes of varying length where reliable data is still scarce.

Modifications and variations of the methods and materials described above will be obvious to those skilled in the art from the foregoing detailed description and are intended to come within the scope of the appended claims. References cited herein are specifically incorporated by reference.

We claim:

1. A composition comprising an adjuvant and T-cell epitopes derived from BRD4-NUT (bromodomain containing 4 protein-nuclear protein in testis) fusion protein regions comprising a sequence selected from the group consisting of SEQ ID NOs:28, 31-32, 38-39, 41, 43-46, 200, 201, 203, 209-211, 213-216, 218-220, 223, and 225-230.

2. The composition of claim 1, comprising HLA multimers.

3. The composition of claim 2, further comprising dextran.

* * * * *

SEQUENCE LISTING

```
<160> NUMBER OF SEQ ID NOS: 448

<210> SEQ ID NO 1
<211> LENGTH: 9
<212> TYPE: PRT
<213> ORGANISM: Artificial Sequence
<220> FEATURE:
<223> OTHER INFORMATION: HLA A2 epitope

<400> SEQUENCE: 1

Tyr Ala Glu Glu Ile Tyr Gln Tyr Leu
1               5

<210> SEQ ID NO 2
<211> LENGTH: 9
<212> TYPE: PRT
<213> ORGANISM: Artificial Sequence
<220> FEATURE:
<223> OTHER INFORMATION: HLA A2 epitope

<400> SEQUENCE: 2

Ala Glu Thr Leu Tyr Leu Ala Val Asn
1               5

<210> SEQ ID NO 3
<211> LENGTH: 9
<212> TYPE: PRT
<213> ORGANISM: Artificial Sequence
<220> FEATURE:
<223> OTHER INFORMATION: HLA A2 epitope

<400> SEQUENCE: 3

Phe Leu Asp Arg Phe Leu Ser Cys Met
1               5
```

<210> SEQ ID NO 4
<211> LENGTH: 9
<212> TYPE: PRT
<213> ORGANISM: Artificial Sequence
<220> FEATURE:
<223> OTHER INFORMATION: HLA A2 epitope

<400> SEQUENCE: 4

Ala Ser Lys Tyr Glu Glu Ile Tyr Pro
1               5

<210> SEQ ID NO 5
<211> LENGTH: 11
<212> TYPE: PRT
<213> ORGANISM: Artificial Sequence
<220> FEATURE:
<223> OTHER INFORMATION: HLA A2 epitope

<400> SEQUENCE: 5

Ser Leu Ile Ala Ala Ala Ala Phe Cys Leu Ala
1               5                   10

<210> SEQ ID NO 6
<211> LENGTH: 9
<212> TYPE: PRT
<213> ORGANISM: Artificial Sequence
<220> FEATURE:
<223> OTHER INFORMATION: HLA A2 epitope

<400> SEQUENCE: 6

Leu Ile Ala Ala Ala Ala Phe Cys Leu
1               5

<210> SEQ ID NO 7
<211> LENGTH: 8
<212> TYPE: PRT
<213> ORGANISM: Artificial Sequence
<220> FEATURE:
<223> OTHER INFORMATION: HLA A2 epitope

<400> SEQUENCE: 7

Tyr Leu Pro Ser Leu Ile Ala Ala
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Ala Ile Met Tyr Pro Gly Ser Phe Ile
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 9

Tyr Leu Ser Trp Glu Gly Pro Gly Leu
1               5

```
<210> SEQ ID NO 10
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 10

Met Ala Phe Ala Glu Asp Val Tyr Glu Val
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 11

Thr Leu Lys Ser Asp Leu His Phe Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 12

Ser Leu Gly Thr Asp Val Ile Asn Val
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 13

Tyr Gln Tyr Leu Arg Glu Ala Glu Ile
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 14

Arg Thr Ile Leu Val Asp Trp Leu Val
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 15

Ile Leu Val Asp Trp Leu Val Glu Val
1               5

<210> SEQ ID NO 16
```

```
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 16

Lys Leu Arg Ala Glu Thr Leu Tyr Leu
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 17

Val Leu Arg Gly Lys Leu Gln Leu Val
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 18

Gln Leu Leu Lys Met Glu His Leu Leu
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 19

Lys Val Leu Ala Phe Asp Leu Thr Val
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 20

Asn Leu Ala Lys Tyr Val Ala Glu Leu
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 21

Ser Leu Leu Glu Ala Asp Pro Phe Leu
1               5

<210> SEQ ID NO 22
<211> LENGTH: 9
```

```
<212> TYPE: PRT
<213> ORGANISM: Artificial Sequence
<220> FEATURE:
<223> OTHER INFORMATION: Synthetic Peptide

<400> SEQUENCE: 22

Tyr Leu Pro Ser Leu Ile Ala Ala Ala
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 23

Phe Thr Gly Tyr Ser Leu Ser Glu Ile
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 24

Ser Leu Ser Glu Ile Val Pro Cys Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 25

Ser Leu Met Glu Pro Pro Ala Val Leu
1               5

<210> SEQ ID NO 26
<211> LENGTH: 306
<212> TYPE: PRT
<213> ORGANISM: Artificial Sequence
<220> FEATURE:
<223> OTHER INFORMATION: Synthetic Polypeptide - BRD4-NUT fusion region
      sequence

<400> SEQUENCE: 26

Glu Pro Ser Leu Lys Asn Ser Asn Pro Asp Glu Ile Glu Ile Asp Phe
1               5                   10                  15

Glu Thr Leu Lys Pro Ser Thr Leu Arg Glu Leu Glu Arg Tyr Val Thr
            20                  25                  30

Ser Cys Leu Arg Lys Lys Arg Lys Pro Gln Ala Glu Lys Val Asp Val
        35                  40                  45

Ile Ala Gly Ser Ser Lys Met Lys Gly Phe Ser Ser Ser Glu Ser Glu
    50                  55                  60

Ser Ser Ser Glu Ser Ser Ser Asp Ser Glu Asp Ser Glu Thr Ala
65                  70                  75                  80

Ser Ala Leu Pro Gly Pro Asp Met Ser Met Lys Pro Ser Ala Ala Leu
                85                  90                  95

Ser Pro Ser Pro Ala Leu Pro Phe Leu Pro Pro Thr Ser Asp Pro Pro
```

```
            100                 105                 110
Asp His Pro Pro Arg Glu Pro Pro Gln Pro Ile Met Pro Ser Val
        115                 120                 125

Phe Ser Pro Asp Asn Pro Leu Met Leu Ser Ala Phe Pro Ser Ser Leu
    130                 135                 140

Leu Val Thr Gly Asp Gly Pro Cys Leu Ser Gly Ala Gly Ala Gly
145                 150                 155                 160

Lys Val Ile Val Lys Val Lys Thr Glu Gly Gly Ser Ala Glu Pro Ser
                165                 170                 175

Gln Thr Gln Asn Phe Ile Leu Thr Gln Thr Ala Leu Asn Ser Thr Ala
            180                 185                 190

Pro Gly Thr Pro Cys Gly Gly Leu Glu Gly Pro Ala Pro Pro Phe Val
        195                 200                 205

Thr Ala Ser Asn Val Lys Thr Ile Leu Pro Ser Lys Ala Val Gly Val
    210                 215                 220

Ser Gln Glu Gly Pro Pro Gly Leu Pro Pro Gln Pro Pro Pro Val
225                 230                 235                 240

Ala Gln Leu Val Pro Ile Val Pro Leu Glu Lys Ala Trp Pro Gly Pro
                245                 250                 255

His Gly Thr Thr Gly Glu Gly Gly Pro Val Ala Thr Leu Ser Lys Pro
            260                 265                 270

Ser Leu Gly Asp Arg Ser Lys Ile Ser Lys Asp Val Tyr Glu Asn Phe
        275                 280                 285

Arg Gln Trp Gln Arg Tyr Lys Ala Leu Ala Arg Arg His Leu Ser Gln
    290                 295                 300

Ser Pro
305

<210> SEQ ID NO 27
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 27

Thr Leu Arg Glu Leu Glu Arg Tyr Val
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 28

Met Leu Ser Ala Phe Pro Ser Ser Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 29

Ser Ala Phe Pro Ser Ser Leu Leu Val
1               5
```

```
<210> SEQ ID NO 30
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 30

Ile Leu Pro Ser Lys Ala Val Gly Val
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 31

Ala Leu Pro Gly Pro Asp Met Ser Met
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 32

Met Ser Met Lys Pro Ser Ala Ala Leu
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 33

Ala Ala Leu Ser Pro Ser Pro Ala Leu
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 34

Ile Met Glu Leu Gln Ser Pro Glu Tyr
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 35

Phe His Pro Thr Asp Ala Asn Thr Ile
1               5
```

```
<210> SEQ ID NO 36
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 36

Val Tyr Glu Gly Gln Val Ser Gly Met
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 37

Ala Gln Leu Val Pro Ile Val Pro Leu
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 38

Cys Leu Ser Gly Ala Gly Ala Gly Lys
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 39

Val Ile Ala Gly Ser Ser Lys Met Lys
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 40

Tyr Val Thr Ser Cys Leu Arg Lys Lys
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 41

Lys Pro Gln Ala Glu Lys Val Asp Val
1               5
```

```
<210> SEQ ID NO 42
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 42

Lys Pro Ser Ala Ala Leu Ser Pro Ser
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 43

Ser Pro Ser Pro Ala Leu Pro Phe Leu
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 44

Ser Pro Ala Leu Pro Phe Leu Pro Pro
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 45

Pro Pro Gln Pro Ile Met Pro Ser Val
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 46

Ala Pro Gly Thr Pro Cys Gly Gly Leu
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 47

Gly Pro Ala Pro Pro Phe Val Thr Ala
1               5

<210> SEQ ID NO 48
```

```
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 48

Leu Pro Pro Gln Pro Pro Pro Pro Val
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 49

Gln Pro Pro Pro Pro Val Ala Gln Leu
1               5

<210> SEQ ID NO 50
<211> LENGTH: 222
<212> TYPE: PRT
<213> ORGANISM: Artificial Sequence
<220> FEATURE:
<223> OTHER INFORMATION: Synthetic Peptide

<400> SEQUENCE: 50

Lys Gly Ala Glu Ile Lys Thr Thr Asn Glu Val Val Leu Ala Val Glu
1               5                   10                  15

Phe His Pro Thr Asp Ala Asn Thr Ile Ile Thr Cys Gly Lys Ser His
                20                  25                  30

Ile Phe Phe Trp Thr Trp Ser Gly Asn Ser Leu Thr Arg Lys Gln Gly
        35                  40                  45

Ile Phe Gly Lys Tyr Glu Lys Pro Lys Phe Val Gln Cys Leu Ala Phe
    50                  55                  60

Leu Gly Asn Gly Asp Val Leu Thr Gly Asp Ser Gly Gly Val Met Leu
65                  70                  75                  80

Ile Trp Ser Lys Thr Thr Val Glu Pro Thr Pro Gly Lys Gly Pro Lys
                85                  90                  95

Gly Val Tyr Gln Leu Ser Lys Gln Leu Lys Ala His Asp Gly Ser Val
                100                 105                 110

Phe Thr Leu Cys Gln Met Arg Asn Gly Met Leu Leu Thr Gly Gly Gly
            115                 120                 125

Lys Asp Arg Lys Ile Ile Leu Trp Asp His Asp Leu Asn Pro Glu Arg
130                 135                 140

Glu Ile Met Glu Leu Gln Ser Pro Glu Tyr Lys Leu Ser Lys Leu Arg
145                 150                 155                 160

Thr Ser Thr Ile Met Thr Asp Tyr Asn Pro Asn Tyr Cys Phe Ala Gly
                165                 170                 175

Lys Thr Ser Ser Ile Ser Asp Leu Lys Glu Val Pro Arg Lys Asn Ile
                180                 185                 190

Thr Leu Ile Arg Gly Leu Gly His Gly Ala Phe Gly Glu Val Tyr Glu
            195                 200                 205

Gly Gln Val Ser Gly Met Pro Asn Asp Pro Ser Pro Leu Gln
        210                 215                 220

<210> SEQ ID NO 51
<211> LENGTH: 10
```

```
<212> TYPE: PRT
<213> ORGANISM: Artificial Sequence
<220> FEATURE:
<223> OTHER INFORMATION: Synthetic Peptide

<400> SEQUENCE: 51

Ser Leu Ala Met Leu Asp Leu Leu His Val
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 52

Gly Val Leu Leu Trp Glu Ile Phe Ser Leu
1               5                   10

<210> SEQ ID NO 53
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 53

Leu Ala Met Leu Asp Leu Leu His Val
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 54

Val Leu Leu Trp Glu Ile Phe Ser Leu
1               5

<210> SEQ ID NO 55
<211> LENGTH: 222
<212> TYPE: PRT
<213> ORGANISM: Artificial Sequence
<220> FEATURE:
<223> OTHER INFORMATION: Synthetic Peptide

<400> SEQUENCE: 55

Lys Gly Ala Glu Ile Lys Thr Thr Asn Glu Val Val Leu Ala Val Glu
1               5                   10                  15

Phe His Pro Thr Asp Ala Asn Thr Ile Ile Thr Cys Gly Lys Ser His
                20                  25                  30

Ile Phe Phe Trp Thr Trp Ser Gly Asn Ser Leu Thr Arg Lys Gln Gly
            35                  40                  45

Ile Phe Gly Lys Tyr Glu Lys Pro Lys Phe Val Gln Cys Leu Ala Phe
        50                  55                  60

Leu Gly Asn Gly Asp Val Leu Thr Gly Asp Ser Gly Gly Val Met Leu
65                  70                  75                  80

Ile Trp Ser Lys Thr Thr Val Glu Pro Thr Pro Gly Lys Gly Pro Lys
                85                  90                  95

Gly Val Tyr Gln Leu Ser Lys Gln Leu Lys Ala His Asp Gly Ser Val
            100                 105                 110
```

```
Phe Thr Leu Cys Gln Met Arg Asn Gly Met Leu Leu Thr Gly Gly Gly
            115                 120                 125

Lys Asp Arg Lys Ile Ile Leu Trp Asp His Asp Leu Asn Pro Glu Arg
    130                 135                 140

Glu Ile Met Glu Leu Gln Ser Pro Glu Tyr Lys Leu Ser Lys Leu Arg
145                 150                 155                 160

Thr Ser Thr Ile Met Thr Asp Tyr Asn Pro Asn Tyr Cys Phe Ala Gly
                165                 170                 175

Lys Thr Ser Ser Ile Ser Asp Leu Lys Glu Val Pro Arg Lys Asn Ile
            180                 185                 190

Thr Leu Ile Arg Gly Leu Gly His Gly Ala Phe Gly Glu Val Tyr Glu
        195                 200                 205

Gly Gln Val Ser Gly Met Pro Asn Asp Pro Ser Pro Leu Gln
    210                 215                 220

<210> SEQ ID NO 56
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 56

Thr Thr Asn Glu Val Val Leu Ala Val
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 57

Val Leu Ala Val Glu Phe His Pro Thr
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 58

Lys Phe Val Gln Cys Leu Ala Phe Leu
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 59

Phe Leu Gly Asn Gly Asp Val Leu Thr
1               5

<210> SEQ ID NO 60
<211> LENGTH: 9
<212> TYPE: PRT
<213> ORGANISM: Artificial Sequence
```

```
<220> FEATURE:
<223> OTHER INFORMATION: Synthetic Peptide

<400> SEQUENCE: 60

Val Leu Thr Gly Asp Ser Gly Gly Val
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 61

Met Leu Ile Trp Ser Lys Thr Thr Val
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 62

Lys Ile Ile Leu Trp Asp His Asp Leu
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 63

Ile Leu Trp Asp His Asp Leu Asn Pro
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 64

Glu Leu Gln Ser Pro Glu Tyr Lys Leu
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 65

Gly Met Pro Asn Asp Pro Ser Pro Leu
1               5

<210> SEQ ID NO 66
<211> LENGTH: 9
<212> TYPE: PRT
<213> ORGANISM: Artificial Sequence
<220> FEATURE:
```

```
<223> OTHER INFORMATION: Synthetic Peptide

<400> SEQUENCE: 66

Trp Ser Gly Asn Ser Leu Thr Arg Lys
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 67

Thr Thr Val Glu Pro Thr Pro Gly Lys
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 68

Ser Val Phe Thr Leu Cys Gln Met Arg
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 69

Gly Met Leu Leu Thr Gly Gly Gly Lys
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 70

Arg Thr Ser Thr Ile Met Thr Asp Tyr
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 71

Ile Met Thr Asp Tyr Asn Pro Asn Tyr
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic Peptide
```

```
<400> SEQUENCE: 72

Lys Thr Ser Ser Ile Ser Asp Leu Lys
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 73

Ile Thr Leu Ile Arg Gly Leu Gly His
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 74

His Pro Thr Asp Ala Asn Thr Ile Ile
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 75

Lys Pro Lys Phe Val Gln Cys Leu Ala
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 76

Thr Pro Gly Lys Gly Pro Lys Gly Val
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 77

Asn Pro Glu Arg Glu Ile Met Glu Leu
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic Peptide
```

```
<400> SEQUENCE: 78

Ser Pro Glu Tyr Lys Leu Ser Lys Leu
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 79

Val Pro Arg Lys Asn Ile Thr Leu Ile
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 80

Ala Phe Leu Gly Asn Gly Asp Val Leu
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 81

Cys Gln Met Arg Asn Gly Met Leu Leu
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 82

Cys Phe Ala Gly Lys Thr Ser Ser Ile
1               5

<210> SEQ ID NO 83
<211> LENGTH: 220
<212> TYPE: PRT
<213> ORGANISM: Artificial Sequence
<220> FEATURE:
<223> OTHER INFORMATION: Synthetic Peptide

<400> SEQUENCE: 83

Met Thr Ala Ser Ser Ser Ser Asp Tyr Gly Gln Thr Ser Lys Met Ser
1               5                   10                  15

Pro Arg Val Pro Gln Gln Asp Trp Leu Ser Gln Pro Pro Ala Arg Val
            20                  25                  30

Thr Ile Lys Met Glu Cys Asn Pro Ser Gln Val Asn Gly Ser Arg Asn
        35                  40                  45

Ser Pro Asp Glu Cys Ser Val Ala Lys Gly Gly Lys Met Val Gly Ser
    50                  55                  60
```

Pro Asp Thr Val Gly Met Asn Tyr Gly Ser Tyr Met Glu Glu Lys His
 65                  70                  75                  80

Met Pro Pro Asn Met Thr Thr Asn Glu Arg Arg Val Ile Val Pro
             85                  90                  95

Ala Asp Pro Thr Leu Trp Ser Thr Asp His Val Arg Gln Trp Leu Glu
            100                 105                 110

Trp Ala Val Lys Glu Tyr Gly Leu Pro Asp Val Asn Ile Leu Leu Phe
            115                 120                 125

Gln Asn Ile Asp Gly Lys Glu Leu Cys Lys Met Thr Lys Asp Asp Phe
130                 135                 140

Gln Arg Leu Thr Pro Ser Tyr Asn Ala Asp Ile Leu Leu Ser His Leu
145                 150                 155                 160

His Tyr Leu Arg Glu Thr Pro Leu Pro His Leu Thr Ser Asp Asp Val
                165                 170                 175

Asp Lys Ala Leu Gln Asn Ser Pro Arg Leu Met His Ala Arg Asn Thr
            180                 185                 190

Gly Gly Ala Ala Phe Ile Phe Pro Asn Thr Ser Val Tyr Pro Glu Ala
            195                 200                 205

Thr Gln Arg Ile Thr Thr Arg Pro Val Ser Tyr Arg
210                 215                 220

<210> SEQ ID NO 84
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 84

Trp Leu Ser Gln Pro Pro Ala Arg Val
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 85

Lys Met Val Gly Ser Pro Asp Thr Val
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 86

Val Ile Val Pro Ala Asp Pro Thr Leu
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 87

```
Gly Leu Pro Asp Val Asn Ile Leu Leu
1               5
```

<210> SEQ ID NO 88
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 88

```
Ile Leu Leu Ser His Leu His Tyr Leu
1               5
```

<210> SEQ ID NO 89
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 89

```
Lys Met Glu Cys Asn Pro Ser Gln Val
1               5
```

<210> SEQ ID NO 90
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 90

```
Lys Ala Leu Gln Asn Ser Pro Arg Leu
1               5
```

<210> SEQ ID NO 91
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 91

```
Thr Leu Trp Ser Thr Asp His Val Arg
1               5
```

<210> SEQ ID NO 92
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 92

```
Arg Gln Trp Leu Glu Trp Ala Val Lys
1               5
```

<210> SEQ ID NO 93
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 93

```
Leu Leu Phe Gln Asn Ile Asp Gly Lys
```

```
<210> SEQ ID NO 94
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 94

Asn Ile Asp Gly Lys Glu Leu Cys Lys
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 95

Lys Met Thr Lys Asp Asp Phe Gln Arg
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 96

Leu Leu Ser His Leu His Tyr Leu Arg
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 97

His Leu Thr Ser Asp Asp Val Asp Lys
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 98

Phe Ile Phe Pro Asn Thr Ser Val Tyr
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 99

Ser Val Tyr Pro Glu Ala Thr Gln Arg
1               5
```

<210> SEQ ID NO 100
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 100

Arg Ile Thr Thr Arg Pro Val Ser Tyr
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 101

Ile Thr Thr Arg Pro Val Ser Tyr Arg
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 102

Glu Tyr Gly Leu Pro Asp Val Asn Ile
1               5

<210> SEQ ID NO 103
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 103

Val Tyr Pro Glu Ala Thr Gln Arg Ile
1               5

<210> SEQ ID NO 104
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 104

Ser Pro Arg Val Pro Gln Gln Asp Trp
1               5

<210> SEQ ID NO 105
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 105

Pro Pro Ala Arg Val Thr Ile Lys Met
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 106

Leu Pro Asp Val Asn Ile Leu Leu Phe
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 107

Thr Pro Ser Tyr Asn Ala Asp Ile Leu
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 108

Leu Pro His Leu Thr Ser Asp Asp Val
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 109

His Ala Arg Asn Thr Gly Gly Ala Ala
1               5

<210> SEQ ID NO 110
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 110

Tyr Pro Glu Ala Thr Gln Arg Ile Thr
1               5

<210> SEQ ID NO 111
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 111

Pro Arg Val Pro Gln Gln Asp Trp Leu
1               5

```
<210> SEQ ID NO 112
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 112

Ala Arg Val Thr Ile Lys Met Glu Cys
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 113

Arg Arg Val Ile Val Pro Ala Asp Pro
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 114

Val Arg Gln Trp Leu Glu Trp Ala Val
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 115

Gln Arg Leu Thr Pro Ser Tyr Asn Ala
1               5

<210> SEQ ID NO 116
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 116

Leu Arg Glu Thr Pro Leu Pro His Leu
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 117

Ala Arg Asn Thr Gly Gly Ala Ala Phe
1               5

<210> SEQ ID NO 118
```

<211> LENGTH: 686
<212> TYPE: PRT
<213> ORGANISM: Artificial Sequence
<220> FEATURE:
<223> OTHER INFORMATION: Synthetic Peptide

<400> SEQUENCE: 118

Met Asn Arg Pro Gln Asn Leu Arg Leu Glu Met Thr Ala Ala Lys Asn
1               5                   10                  15

Thr Asn Asn Gln Ser Pro Ser Ala Pro Pro Ala Lys Pro Pro Ser
            20                  25                  30

Thr Gln Arg Ala Val Ile Ser Pro Asp Gly Glu Cys Ser Ile Asp Asp
            35                  40                  45

Leu Ser Phe Tyr Val Asn Arg Leu Ser Ser Leu Val Ile Gln Met Ala
        50                  55                  60

His Lys Glu Ile Lys Glu Lys Leu Glu Gly Lys Ser Lys Cys Leu His
65                  70                  75                  80

His Ser Ile Cys Pro Ser Pro Gly Asn Lys Glu Arg Ile Ser Pro Arg
                    85                  90                  95

Thr Pro Ala Ser Lys Ile Ala Ser Glu Met Ala Tyr Glu Ala Val Glu
                100                 105                 110

Leu Thr Ala Ala Glu Met Arg Gly Thr Gly Glu Glu Ser Arg Glu Gly
            115                 120                 125

Gly Gln Lys Ser Phe Leu Tyr Ser Glu Leu Ser Asn Lys Ser Lys Ser
130                 135                 140

Gly Asp Lys Gln Met Ser Gln Arg Glu Ser Lys Glu Phe Ala Asp Ser
145                 150                 155                 160

Ile Ser Lys Gly Leu Met Val Tyr Ala Asn Gln Val Ala Ser Asp Met
                165                 170                 175

Met Val Ser Leu Met Lys Thr Leu Lys Val His Ser Ser Gly Lys Pro
            180                 185                 190

Ile Pro Ala Ser Val Val Leu Lys Arg Val Leu Leu Arg His Thr Lys
        195                 200                 205

Glu Ile Val Ser Asp Leu Ile Asp Ser Cys Met Lys Asn Leu His Asn
210                 215                 220

Ile Thr Gly Val Leu Met Thr Asp Ser Asp Phe Val Ser Ala Val Lys
225                 230                 235                 240

Arg Asn Leu Phe Asn Gln Trp Lys Gln Asn Ala Thr Asp Ile Met Glu
                245                 250                 255

Ala Met Leu Lys Arg Leu Val Ser Ala Leu Ile Gly Glu Glu Lys Glu
            260                 265                 270

Thr Lys Ser Gln Ser Leu Ser Tyr Ala Ser Leu Lys Ala Gly Ser His
        275                 280                 285

Asp Pro Lys Cys Arg Asn Gln Ser Leu Glu Phe Ser Thr Met Lys Ala
290                 295                 300

Glu Met Lys Glu Arg Asp Lys Gly Lys Met Lys Ser Asp Pro Cys Lys
305                 310                 315                 320

Ser Leu Thr Ser Ala Glu Lys Val Gly Glu His Ile Leu Lys Glu Gly
                325                 330                 335

Leu Thr Ile Trp Asn Gln Lys Gln Gly Asn Ser Cys Lys Val Ala Thr
            340                 345                 350

Lys Ala Cys Ser Asn Lys Asp Glu Lys Gly Glu Lys Ile Asn Ala Ser
        355                 360                 365

Thr Asp Ser Leu Ala Lys Asp Leu Ile Val Ser Ala Leu Lys Leu Ile
370                 375                 380

```
Gln Tyr His Leu Thr Gln Gln Thr Lys Gly Lys Asp Thr Cys Glu Glu
385                 390                 395                 400

Asp Cys Pro Gly Ser Thr Met Gly Tyr Met Ala Gln Ser Thr Gln Tyr
            405                 410                 415

Glu Lys Cys Gly Gly Gln Ser Ala Lys Ala Leu Ser Val Lys Gln
            420                 425                 430

Leu Glu Ser His Arg Ala Pro Gly Pro Ser Thr Cys Gln Lys Glu Asn
            435                 440                 445

Gln His Leu Asp Ser Gln Lys Met Asp Met Ser Asn Ile Val Leu Met
450                 455                 460

Leu Ile Gln Lys Leu Leu Asn Glu Asn Pro Phe Lys Cys Glu Asp Pro
465                 470                 475                 480

Cys Glu Gly Glu Asn Lys Cys Ser Glu Pro Arg Ala Ser Lys Ala Ala
                485                 490                 495

Ser Met Ser Asn Arg Ser Asp Lys Ala Glu Glu Gln Cys Gln Glu His
                500                 505                 510

Gln Glu Leu Asp Cys Thr Ser Gly Met Lys Gln Ala Asn Gly Gln Phe
            515                 520                 525

Ile Asp Lys Leu Val Glu Ser Val Met Lys Leu Cys Leu Ile Met Ala
            530                 535                 540

Lys Tyr Ser Asn Asp Gly Ala Ala Leu Ala Glu Leu Glu Gln Ala
545                 550                 555                 560

Ala Ser Ala Asn Lys Pro Asn Phe Arg Gly Thr Arg Cys Ile His Ser
                565                 570                 575

Gly Ala Met Pro Gln Asn Tyr Gln Asp Ser Leu Gly His Glu Val Ile
                580                 585                 590

Val Asn Asn Gln Cys Ser Thr Asn Ser Leu Gln Lys Gln Leu Gln Ala
            595                 600                 605

Val Leu Gln Trp Ile Ala Ala Ser Gln Phe Asn Val Pro Met Leu Tyr
            610                 615                 620

Phe Met Gly Asp Lys Asp Gly Gln Leu Glu Lys Leu Pro Gln Val Ser
625                 630                 635                 640

Ala Lys Ala Ala Glu Lys Gly Tyr Ser Val Gly Gly Leu Leu Gln Glu
                645                 650                 655

Val Met Lys Phe Ala Lys Glu Arg Gln Pro Asp Glu Ala Val Gly Lys
                660                 665                 670

Val Ala Arg Lys Gln Leu Leu Asp Trp Leu Leu Ala Asn Leu
                675                 680                 685

<210> SEQ ID NO 119
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 119

Ser Ile Asp Asp Leu Ser Phe Tyr Val
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic Peptide
```

<400> SEQUENCE: 120

Tyr Val Asn Arg Leu Ser Ser Leu Val
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 121

Arg Leu Ser Ser Leu Val Ile Gln Met
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 122

Gly Leu Met Val Tyr Ala Asn Gln Val
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 123

Met Met Val Ser Leu Met Lys Thr Leu
1               5

<210> SEQ ID NO 124
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 124

Val Leu Leu Arg His Thr Lys Glu Ile
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 125

Val Leu Met Thr Asp Ser Asp Phe Val
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 126

```
Ala Met Leu Lys Arg Leu Val Ser Ala
1               5
```

<210> SEQ ID NO 127
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 127

```
Lys Met Asp Met Ser Asn Ile Val Leu
1               5
```

<210> SEQ ID NO 128
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 128

```
Val Leu Met Leu Ile Gln Lys Leu Leu
1               5
```

<210> SEQ ID NO 129
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 129

```
Tyr Gln Asp Ser Leu Gly His Glu Val
1               5
```

<210> SEQ ID NO 130
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 130

```
Ser Leu Gln Lys Gln Leu Gln Ala Val
1               5
```

<210> SEQ ID NO 131
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 131

```
Gly Gln Leu Glu Lys Leu Pro Gln Val
1               5
```

<210> SEQ ID NO 132
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 132

Leu Leu Asp Trp Leu Leu Ala Asn Leu
1               5

<210> SEQ ID NO 133
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 133

Val Ala Ser Asp Met Met Val Ser Leu
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 134

Leu Ile Asp Ser Cys Met Lys Asn Leu
1               5

<210> SEQ ID NO 135
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 135

Asn Leu His Asn Ile Thr Gly Val Leu
1               5

<210> SEQ ID NO 136
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 136

Ile Met Glu Ala Met Leu Lys Arg Leu
1               5

<210> SEQ ID NO 137
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 137

Met Leu Lys Arg Leu Val Ser Ala Leu
1               5

<210> SEQ ID NO 138
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 138

Lys Ile Asn Ala Ser Thr Asp Ser Leu

```
1               5
```

<210> SEQ ID NO 139
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 139

```
Leu Ile Val Ser Ala Leu Lys Leu Ile
1               5
```

<210> SEQ ID NO 140
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 140

```
Ala Leu Lys Leu Ile Gln Tyr His Leu
1               5
```

<210> SEQ ID NO 141
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 141

```
Asp Met Ser Asn Ile Val Leu Met Leu
1               5
```

<210> SEQ ID NO 142
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 142

```
Ile Val Leu Met Leu Ile Gln Lys Leu
1               5
```

<210> SEQ ID NO 143
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 143

```
Leu Leu Asn Glu Asn Pro Phe Lys Cys
1               5
```

<210> SEQ ID NO 144
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 144

```
Phe Ile Asp Lys Leu Val Glu Ser Val
1               5
```

<210> SEQ ID NO 145
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 145

Lys Leu Val Glu Ser Val Met Lys Leu
1               5

<210> SEQ ID NO 146
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 146

Ala Leu Ala Glu Leu Glu Glu Gln Ala
1               5

<210> SEQ ID NO 147
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 147

Gln Leu Gln Ala Val Leu Gln Trp Ile
1               5

<210> SEQ ID NO 148
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 148

Phe Met Gly Asp Lys Asp Gly Gln Leu
1               5

<210> SEQ ID NO 149
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 149

Lys Leu Pro Gln Val Ser Ala Lys Ala
1               5

<210> SEQ ID NO 150
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 150

Lys Ala Ala Glu Lys Gly Tyr Ser Val
1               5

```
<210> SEQ ID NO 151
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 151

Ser Val Gly Gly Leu Leu Gln Glu Val
1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 152

Leu Leu Gln Glu Val Met Lys Phe Ala
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 153

Ser Leu Val Ile Gln Met Ala His Lys
1               5

<210> SEQ ID NO 154
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 154

Ser Ile Cys Pro Ser Pro Gly Asn Lys
1               5

<210> SEQ ID NO 155
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 155

Phe Leu Tyr Ser Glu Leu Ser Asn Lys
1               5

<210> SEQ ID NO 156
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 156

Lys Gln Met Ser Gln Arg Glu Ser Lys
1               5
```

```
<210> SEQ ID NO 157
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 157

Lys Glu Phe Ala Asp Ser Ile Ser Lys
1               5

<210> SEQ ID NO 158
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 158

Ser Ile Ser Lys Gly Leu Met Val Tyr
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 159

Met Val Ser Leu Met Lys Thr Leu Lys
1               5

<210> SEQ ID NO 160
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 160

Thr Leu Lys Val His Ser Ser Gly Lys
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 161

Val Val Leu Lys Arg Val Leu Leu Arg
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 162

Val Leu Lys Arg Val Leu Leu Arg His
1               5

<210> SEQ ID NO 163
```

```
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 163

Gln Ser Leu Ser Tyr Ala Ser Leu Lys
1               5

<210> SEQ ID NO 164
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 164

Gln Ser Leu Glu Phe Ser Thr Met Lys
1               5

<210> SEQ ID NO 165
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 165

His Leu Thr Gln Gln Thr Lys Gly Lys
1               5

<210> SEQ ID NO 166
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 166

Lys Cys Gly Gly Gly Gln Ser Ala Lys
1               5

<210> SEQ ID NO 167
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 167

Asn Ile Val Leu Met Leu Ile Gln Lys
1               5

<210> SEQ ID NO 168
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 168

Lys Leu Leu Asn Glu Asn Pro Phe Lys
1               5

<210> SEQ ID NO 169
<211> LENGTH: 9
```

```
<212> TYPE: PRT
<213> ORGANISM: Artificial Sequence
<220> FEATURE:
<223> OTHER INFORMATION: Synthetic Peptide

<400> SEQUENCE: 169

Lys Leu Cys Leu Ile Met Ala Lys Tyr
1               5

<210> SEQ ID NO 170
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 170

Ser Gln Phe Asn Val Pro Met Leu Tyr
1               5

<210> SEQ ID NO 171
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 171

Gln Val Ser Ala Lys Ala Ala Glu Lys
1               5

<210> SEQ ID NO 172
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 172

Phe Tyr Val Asn Arg Leu Ser Ser Leu
1               5

<210> SEQ ID NO 173
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 173

Lys Tyr Ser Asn Asp Gly Ala Ala Leu
1               5

<210> SEQ ID NO 174
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 174

Gln Phe Asn Val Pro Met Leu Tyr Phe
1               5

<210> SEQ ID NO 175
<211> LENGTH: 9
<212> TYPE: PRT
```

```
<213> ORGANISM: Artificial Sequence
<220> FEATURE:
<223> OTHER INFORMATION: Synthetic Peptide

<400> SEQUENCE: 175

Ile Gln Met Ala His Lys Glu Ile Lys
1               5

<210> SEQ ID NO 176
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 176

Ile Ser Pro Arg Thr Pro Ala Ser Lys
1               5

<210> SEQ ID NO 177
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 177

Lys Gln Met Ser Gln Arg Glu Ser Lys
1               5

<210> SEQ ID NO 178
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 178

Val Val Leu Lys Arg Val Leu Leu Arg
1               5

<210> SEQ ID NO 179
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 179

Met Ala Gln Ser Thr Gln Tyr Glu Lys
1               5

<210> SEQ ID NO 180
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 180

Ala Ser Met Ser Asn Arg Ser Asp Lys
1               5

<210> SEQ ID NO 181
<211> LENGTH: 9
<212> TYPE: PRT
<213> ORGANISM: Artificial Sequence
```

```
<220> FEATURE:
<223> OTHER INFORMATION: Synthetic Peptide

<400> SEQUENCE: 181

Ala Ser Ala Asn Lys Pro Asn Phe Arg
1               5

<210> SEQ ID NO 182
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 182

Gln Ser Pro Ser Ala Pro Pro Ala Lys
1               5

<210> SEQ ID NO 183
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 183

Arg Pro Gln Asn Leu Arg Leu Glu Met
1               5

<210> SEQ ID NO 184
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 184

Lys Pro Pro Ser Thr Gln Arg Ala Val
1               5

<210> SEQ ID NO 185
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 185

Pro Pro Ser Thr Gln Arg Ala Val Ile
1               5

<210> SEQ ID NO 186
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 186

Ser Pro Arg Thr Pro Ala Ser Lys Ile
1               5

<210> SEQ ID NO 187
<211> LENGTH: 9
<212> TYPE: PRT
<213> ORGANISM: Artificial Sequence
<220> FEATURE:
```

```
<223> OTHER INFORMATION: Synthetic Peptide

<400> SEQUENCE: 187

Lys Pro Ile Pro Ala Ser Val Val Leu
1               5

<210> SEQ ID NO 188
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 188

Asp Pro Lys Cys Arg Asn Gln Ser Leu
1               5

<210> SEQ ID NO 189
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 189

Cys Pro Gly Ser Thr Met Gly Tyr Met
1               5

<210> SEQ ID NO 190
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 190

Met Pro Gln Asn Tyr Gln Asp Ser Leu
1               5

<210> SEQ ID NO 191
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 191

Leu Pro Gln Val Ser Ala Lys Ala Ala
1               5

<210> SEQ ID NO 192
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 192

Cys Ser Ile Asp Asp Leu Ser Phe Tyr
1               5

<210> SEQ ID NO 193
<211> LENGTH: 9
<212> TYPE: PRT
<213> ORGANISM: Artificial Sequence
<220> FEATURE:
<223> OTHER INFORMATION: Synthetic Peptide
```

<400> SEQUENCE: 193

Glu Thr Lys Ser Gln Ser Leu Ser Tyr
1               5

<210> SEQ ID NO 194
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 194

Ser Gln Ser Leu Ser Tyr Ala Ser Leu
1               5

<210> SEQ ID NO 195
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 195

Asn Gln Ser Leu Glu Phe Ser Thr Met
1               5

<210> SEQ ID NO 196
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 196

Gly Met Lys Gln Ala Asn Gly Gln Phe
1               5

<210> SEQ ID NO 197
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 197

Leu Gln Lys Gln Leu Gln Ala Val Leu
1               5

<210> SEQ ID NO 198
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 198

Leu Gln Trp Ile Ala Ala Ser Gln Phe
1               5

<210> SEQ ID NO 199
<211> LENGTH: 9
<212> TYPE: PRT
<213> ORGANISM: Artificial Sequence
<220> FEATURE:
<223> OTHER INFORMATION: Synthetic Peptide

```
<400> SEQUENCE: 199

Ser Leu Ala Met Leu Asp Leu Leu His
1               5

<210> SEQ ID NO 200
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 200

Ala Gly Ala Gly Lys Val Ile Val Lys
1               5

<210> SEQ ID NO 201
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 201

Asn Val Lys Thr Ile Leu Pro Ser Lys
1               5

<210> SEQ ID NO 202
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 202

Leu Val Pro Ile Val Pro Leu Glu Lys
1               5

<210> SEQ ID NO 203
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 203

Ile Glu Ile Asp Phe Glu Thr Leu Lys
1               5

<210> SEQ ID NO 204
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 204

Glu Thr Leu Lys Pro Ser Thr Leu Arg
1               5

<210> SEQ ID NO 205
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 205
```

```
Arg Tyr Val Thr Ser Cys Leu Arg Lys
1               5
```

<210> SEQ ID NO 206
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 206

```
Tyr Val Thr Ser Cys Leu Arg Lys Lys
1               5
```

<210> SEQ ID NO 207
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 207

```
Thr Ser Cys Leu Arg Lys Lys Arg Lys
1               5
```

<210> SEQ ID NO 208
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 208

```
Leu Ser Pro Ser Pro Ala Leu Pro Phe
1               5
```

<210> SEQ ID NO 209
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 209

```
Pro Gln Pro Ile Met Pro Ser Val Phe
1               5
```

<210> SEQ ID NO 210
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 210

```
Val Phe Ser Pro Asp Asn Pro Leu Met
1               5
```

<210> SEQ ID NO 211
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 211

```
Phe Ser Pro Asp Asn Pro Leu Met Leu
1               5
```

<210> SEQ ID NO 212
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 212

```
Leu Ser Ala Phe Pro Ser Ser Leu Leu
1               5
```

<210> SEQ ID NO 213
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 213

```
Val Thr Ala Ser Asn Val Lys Thr Ile
1               5
```

<210> SEQ ID NO 214
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 214

```
Ile Ser Lys Asp Val Tyr Glu Asn Phe
1               5
```

<210> SEQ ID NO 215
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 215

```
Ser Val Phe Ser Pro Asp Asn Pro Leu
1               5
```

<210> SEQ ID NO 216
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 216

```
Pro Pro Val Ala Gln Leu Val Pro Ile
1               5
```

<210> SEQ ID NO 217
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 217

```
Val Ala Thr Leu Ser Lys Pro Ser Leu
```

1               5

<210> SEQ ID NO 218
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 218

Arg Gln Trp Gln Arg Tyr Lys Ala Leu
1               5

<210> SEQ ID NO 219
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 219

Leu Glu Arg Tyr Val Thr Ser Cys Leu
1               5

<210> SEQ ID NO 220
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 220

Cys Leu Arg Lys Lys Arg Lys Pro Gln
1               5

<210> SEQ ID NO 221
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 221

Leu Arg Lys Lys Arg Lys Pro Gln Ala
1               5

<210> SEQ ID NO 222
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 222

Arg Lys Lys Arg Lys Pro Gln Ala Glu
1               5

<210> SEQ ID NO 223
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 223

Asn Phe Ile Leu Thr Gln Thr Ala Leu
1               5

<210> SEQ ID NO 224
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 224

Ala Leu Ala Arg Arg His Leu Ser Gln
1               5

<210> SEQ ID NO 225
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 225

Thr Gln Thr Ala Leu Asn Ser Thr Ala
1               5

<210> SEQ ID NO 226
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 226

Gly Leu Glu Gly Pro Ala Pro Pro Phe
1               5

<210> SEQ ID NO 227
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 227

Arg Ser Lys Ile Ser Lys Asp Val Tyr
1               5

<210> SEQ ID NO 228
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 228

Trp Gln Arg Tyr Lys Ala Leu Ala Arg
1               5

<210> SEQ ID NO 229
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 229

Ala Glu Pro Ser Gln Thr Gln Asn Phe
1               5

```
<210> SEQ ID NO 230
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 230

Glu Ile Glu Ile Asp Phe Glu Thr Leu
1               5

<210> SEQ ID NO 231
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 231

Phe Glu Thr Leu Lys Pro Ser Thr Leu
1               5

<210> SEQ ID NO 232
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 232

Lys Val Lys Thr Glu Gly Gly Ser Ala
1               5

<210> SEQ ID NO 233
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 233

Val Thr Ser Cys Leu Arg Lys Lys Arg
1               5

<210> SEQ ID NO 234
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 234

Tyr Lys Ala Leu Ala Arg Arg His Leu
1               5

<210> SEQ ID NO 235
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 235

Gly Gly Val Met Leu Ile Trp Ser Lys
1               5
```

```
<210> SEQ ID NO 236
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 236

Val Tyr Gln Leu Ser Lys Gln Leu Lys
1               5

<210> SEQ ID NO 237
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 237

Leu Thr Gly Gly Gly Lys Asp Arg Lys
1               5

<210> SEQ ID NO 238
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 238

Gln Ser Pro Glu Tyr Lys Leu Ser Lys
1               5

<210> SEQ ID NO 239
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 239

Ile Ser Asp Leu Lys Glu Val Pro Arg
1               5

<210> SEQ ID NO 240
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 240

Glu Ile Lys Thr Thr Asn Glu Val Val
1               5

<210> SEQ ID NO 241
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 241

Asn Ser Leu Thr Arg Lys Gln Gly Ile
1               5

<210> SEQ ID NO 242
```

```
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 242

Ser Leu Thr Arg Lys Gln Gly Ile Phe
1               5

<210> SEQ ID NO 243
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 243

Tyr Glu Lys Pro Lys Phe Val Gln Cys
1               5

<210> SEQ ID NO 244
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 244

Gln Leu Lys Ala His Asp Gly Ser Val
1               5

<210> SEQ ID NO 245
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 245

Leu Cys Gln Met Arg Asn Gly Met Leu
1               5

<210> SEQ ID NO 246
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 246

Gly Gly Lys Asp Arg Lys Ile Ile Leu
1               5

<210> SEQ ID NO 247
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 247

Leu Ser Lys Leu Arg Thr Ser Thr Ile
1               5

<210> SEQ ID NO 248
<211> LENGTH: 9
```

```
<212> TYPE: PRT
<213> ORGANISM: Artificial Sequence
<220> FEATURE:
<223> OTHER INFORMATION: Synthetic Peptide

<400> SEQUENCE: 248

Glu Val Pro Arg Lys Asn Ile Thr Leu
1               5

<210> SEQ ID NO 249
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 249

Ile Thr Cys Gly Lys Ser His Ile Phe
1               5

<210> SEQ ID NO 250
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 250

Ser Ser Asp Tyr Gly Gln Thr Ser Lys
1               5

<210> SEQ ID NO 251
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 251

Met Thr Ala Ser Ser Ser Ser Asp Tyr
1               5

<210> SEQ ID NO 252
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 252

Gly Gln Thr Ser Lys Met Ser Pro Arg
1               5

<210> SEQ ID NO 253
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 253

Ser Gln Pro Pro Ala Arg Val Thr Ile
1               5

<210> SEQ ID NO 254
<211> LENGTH: 9
<212> TYPE: PRT
```

```
<213> ORGANISM: Artificial Sequence
<220> FEATURE:
<223> OTHER INFORMATION: Synthetic Peptide

<400> SEQUENCE: 254

Asn Tyr Gly Ser Tyr Met Glu Glu Lys
1               5

<210> SEQ ID NO 255
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 255

Ser Tyr Met Glu Glu Lys His Met Pro
1               5

<210> SEQ ID NO 256
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 256

Val Asn Ile Leu Leu Phe Gln Asn Ile
1               5

<210> SEQ ID NO 257
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 257

His Tyr Leu Arg Glu Thr Pro Leu Pro
1               5

<210> SEQ ID NO 258
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 258

Asn Thr Gly Gly Ala Ala Phe Ile Phe
1               5

<210> SEQ ID NO 259
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 259

Val Pro Gln Gln Asp Trp Leu Ser Gln
1               5

<210> SEQ ID NO 260
<211> LENGTH: 9
<212> TYPE: PRT
<213> ORGANISM: Artificial Sequence
```

```
<220> FEATURE:
<223> OTHER INFORMATION: Synthetic Peptide

<400> SEQUENCE: 260

Val Pro Ala Asp Pro Thr Leu Trp Ser
1               5

<210> SEQ ID NO 261
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 261

Ser Pro Arg Leu Met His Ala Arg Asn
1               5

<210> SEQ ID NO 262
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 262

Met Thr Lys Asp Asp Phe Gln Arg Leu
1               5

<210> SEQ ID NO 263
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 263

Leu His Tyr Leu Arg Glu Thr Pro Leu
1               5

<210> SEQ ID NO 264
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 264

Leu Gln Asn Ser Pro Arg Leu Met His
1               5

<210> SEQ ID NO 265
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 265

Thr Val Gly Met Asn Tyr Gly Ser Tyr
1               5

<210> SEQ ID NO 266
<211> LENGTH: 9
<212> TYPE: PRT
<213> ORGANISM: Artificial Sequence
<220> FEATURE:
```

<223> OTHER INFORMATION: Synthetic Peptide

<400> SEQUENCE: 266

Trp Leu Glu Trp Ala Val Lys Glu Tyr
1               5

<210> SEQ ID NO 267
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 267

Phe Gln Asn Ile Asp Gly Lys Glu Leu
1               5

<210> SEQ ID NO 268
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 268

Thr Gln Arg Ile Thr Thr Arg Pro Val
1               5

<210> SEQ ID NO 269
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 269

Ser Leu Ala Lys Asp Leu Ile Val Ser Ala
1               5                   10

<210> SEQ ID NO 270
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 270

Glu Cys Ser Ile Asp Asp Leu Ser Phe Tyr Val
1               5                   10

<210> SEQ ID NO 271
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 271

Gln Leu Leu Asp Trp Leu Leu Ala Asn Leu
1               5                   10

<210> SEQ ID NO 272
<211> LENGTH: 10
<212> TYPE: PRT
<213> ORGANISM: Artificial Sequence
<220> FEATURE:
<223> OTHER INFORMATION: Synthetic Peptide

```
<400> SEQUENCE: 272

Asp Lys Leu Val Glu Ser Val Met Lys Leu
1               5                   10

<210> SEQ ID NO 273
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 273

Gln Phe Ile Asp Lys Leu Val Glu Ser Val
1               5                   10

<210> SEQ ID NO 274
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 274

Met Asp Met Ser Asn Ile Val Leu Met Leu
1               5                   10

<210> SEQ ID NO 275
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 275

Pro Ile Pro Ala Ser Val Val Leu Lys
1               5

<210> SEQ ID NO 276
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 276

Val Ser Ala Leu Ile Gly Glu Glu Lys
1               5

<210> SEQ ID NO 277
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 277

Asn Ala Ser Thr Asp Ser Leu Ala Lys
1               5

<210> SEQ ID NO 278
<211> LENGTH: 9
<212> TYPE: PRT
<213> ORGANISM: Artificial Sequence
<220> FEATURE:
<223> OTHER INFORMATION: Synthetic Peptide
```

```
<400> SEQUENCE: 278

Lys Asp Leu Ile Val Ser Ala Leu Lys
1               5

<210> SEQ ID NO 279
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 279

Gln Ser Ala Lys Ala Leu Ser Val Lys
1               5

<210> SEQ ID NO 280
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 280

Lys Cys Ser Glu Pro Arg Ala Ser Lys
1               5

<210> SEQ ID NO 281
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 281

Glu Leu Asp Cys Thr Ser Gly Met Lys
1               5

<210> SEQ ID NO 282
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 282

Gln Ala Asn Gly Gln Phe Ile Asp Lys
1               5

<210> SEQ ID NO 283
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 283

Gln Cys Ser Thr Asn Ser Leu Gln Lys
1               5

<210> SEQ ID NO 284
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 284
```

```
Arg Gln Pro Asp Glu Ala Val Gly Lys
1               5
```

<210> SEQ ID NO 285
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 285

```
Tyr Ser Glu Leu Ser Asn Lys Ser Lys
1               5
```

<210> SEQ ID NO 286
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 286

```
Ser Asp Met Met Val Ser Leu Met Lys
1               5
```

<210> SEQ ID NO 287
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 287

```
Thr Asp Ile Met Glu Ala Met Leu Lys
1               5
```

<210> SEQ ID NO 288
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 288

```
Phe Ser Thr Met Lys Ala Glu Met Lys
1               5
```

<210> SEQ ID NO 289
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 289

```
Gly Asn Ser Cys Lys Val Ala Thr Lys
1               5
```

<210> SEQ ID NO 290
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 290

Glu Val Met Lys Phe Ala Lys Glu Arg
1               5

<210> SEQ ID NO 291
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 291

Val Ser Ala Val Lys Arg Asn Leu Phe
1               5

<210> SEQ ID NO 292
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 292

Ala Pro Pro Ala Lys Pro Pro Ser Thr
1               5

<210> SEQ ID NO 293
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 293

Glu Pro Arg Ala Ser Lys Ala Ala Ser
1               5

<210> SEQ ID NO 294
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 294

Met Asn Arg Pro Gln Asn Leu Arg Leu
1               5

<210> SEQ ID NO 295
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 295

Asn Leu Arg Leu Glu Met Thr Ala Ala
1               5

<210> SEQ ID NO 296
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 296

Asp Leu Ser Phe Tyr Val Asn Arg Leu

```
1               5

<210> SEQ ID NO 297
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 297

Lys Leu Glu Gly Lys Ser Lys Cys Leu
1               5

<210> SEQ ID NO 298
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 298

Ser Val Val Leu Lys Arg Val Leu Leu
1               5

<210> SEQ ID NO 299
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 299

Glu Ala Met Leu Lys Arg Leu Val Ser
1               5

<210> SEQ ID NO 300
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 300

Glu Lys Glu Thr Lys Ser Gln Ser Leu
1               5

<210> SEQ ID NO 301
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 301

Val Gly Lys Val Ala Arg Lys Gln Leu
1               5

<210> SEQ ID NO 302
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 302

Gly Val Leu Met Thr Asp Ser Asp Phe
1               5
```

<210> SEQ ID NO 303
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 303

Ile Leu Lys Glu Gly Leu Thr Ile Trp
1               5

<210> SEQ ID NO 304
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 304

Lys Leu Ile Gln Tyr His Leu Thr Gln
1               5

<210> SEQ ID NO 305
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 305

Gly Leu Leu Gln Glu Val Met Lys Phe
1               5

<210> SEQ ID NO 306
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 306

Met Met Val Ser Leu Met Lys Thr Leu Lys Val
1               5                   10

<210> SEQ ID NO 307
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 307

Leu Met Thr Asp Ser Asp Phe Val Ser Ala Val
1               5                   10

<210> SEQ ID NO 308
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 308

Lys Gln Leu Leu Asp Trp Leu Leu Ala Asn Leu
1               5                   10

```
<210> SEQ ID NO 309
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 309

Leu Lys Ala His Asp Gly Ser Val Phe
1               5

<210> SEQ ID NO 310
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 310

Ser Leu Asp Asp Ile Ile Ile Tyr Lys
1               5

<210> SEQ ID NO 311
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 311

Ile Ile Tyr Lys Glu Leu Glu Gly Thr
1               5

<210> SEQ ID NO 312
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 312

Lys Val Asn Phe Leu Asp Met Ser Leu
1               5

<210> SEQ ID NO 313
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 313

Phe Leu Asp Met Ser Leu Asp Asp Ile
1               5

<210> SEQ ID NO 314
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 314

Leu Ile Val Thr Gln Arg Asp Leu Val
1               5
```

```
<210> SEQ ID NO 315
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 315

Lys Val Pro Pro Asn His Pro Ser Arg
1               5

<210> SEQ ID NO 316
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 316

Gln Leu Lys Arg His His Pro Gln Tyr
1               5

<210> SEQ ID NO 317
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 317

Asn Ser Glu Glu Gly Asn His Asp Lys
1               5

<210> SEQ ID NO 318
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 318

Pro Ser Gln Lys Pro Ser Gly Phe Lys
1               5

<210> SEQ ID NO 319
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 319

Gly Gln Pro Leu Ile Glu Gln Glu Lys
1               5

<210> SEQ ID NO 320
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 320

Gln Ser Asp Leu Ile Ala Thr Gln Arg
1               5

<210> SEQ ID NO 321
```

```
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 321

Arg Tyr Ser Thr Gly Lys Asn Thr Ile
1               5

<210> SEQ ID NO 322
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 322

Met Ala Ser Phe Arg Lys Leu Thr Leu
1               5

<210> SEQ ID NO 323
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 323

His Pro Ser Arg Lys Lys Val Asn Phe
1               5

<210> SEQ ID NO 324
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 324

Ser Pro Ser Arg Gln Gln Ser Lys Ala
1               5

<210> SEQ ID NO 325
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 325

Lys Pro Ser Gln Lys Pro Ser Gly Phe
1               5

<210> SEQ ID NO 326
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 326

His Pro Leu Asn Gly Gln Pro Leu Ile
1               5

<210> SEQ ID NO 327
<211> LENGTH: 9
```

```
<212> TYPE: PRT
<213> ORGANISM: Artificial Sequence
<220> FEATURE:
<223> OTHER INFORMATION: Synthetic Peptide

<400> SEQUENCE: 327

Pro Ser Arg Lys Lys Val Asn Phe Leu
1               5

<210> SEQ ID NO 328
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 328

Arg Lys Lys Val Asn Phe Leu Asp Met
1               5

<210> SEQ ID NO 329
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 329

Gly Phe Lys Ser Gly Gln His Pro Leu
1               5

<210> SEQ ID NO 330
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 330

Ile Ala Thr Gln Arg Asp Leu Ile Val
1               5

<210> SEQ ID NO 331
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 331

Arg Gln Gln Ser Lys Ala His Arg His
1               5

<210> SEQ ID NO 332
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 332

Glu Gln Glu Lys Cys Ser Asp Asn Tyr
1               5

<210> SEQ ID NO 333
<211> LENGTH: 9
<212> TYPE: PRT
```

```
<213> ORGANISM: Artificial Sequence
<220> FEATURE:
<223> OTHER INFORMATION: Synthetic Peptide

<400> SEQUENCE: 333

Gly Gln Ser Glu Arg Ser His Gly His
1               5

<210> SEQ ID NO 334
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 334

Thr Gln Arg Asp Leu Ile Ala Thr Gln
1               5

<210> SEQ ID NO 335
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 335

Thr Gln Arg Asp Leu Ile Val Thr Gln
1               5

<210> SEQ ID NO 336
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 336

Thr Gln Arg Asp Leu Val Ala Thr Glu
1               5

<210> SEQ ID NO 337
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 337

Gly Gln Ser Glu Arg His Gln Arg Tyr
1               5

<210> SEQ ID NO 338
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 338

Met Ser Leu Asp Asp Ile Ile Ile Tyr
1               5

<210> SEQ ID NO 339
<211> LENGTH: 42
<212> TYPE: PRT
<213> ORGANISM: Artificial Sequence
```

```
<220> FEATURE:
<223> OTHER INFORMATION: Synthetic Peptide

<400> SEQUENCE: 339

Val Ser Pro Glu Glu His Ala Met Pro Ile Gly Arg Ile Ala Asp
1               5                   10                  15

Val Gln His Ile Lys Arg Arg Asp Ile Val Leu Lys Arg Glu Leu Gly
            20                  25                  30

Glu Gly Ala Phe Gly Lys Val Phe Leu Ala
        35                  40

<210> SEQ ID NO 340
<211> LENGTH: 56
<212> TYPE: PRT
<213> ORGANISM: Artificial Sequence
<220> FEATURE:
<223> OTHER INFORMATION: Synthetic Peptide

<400> SEQUENCE: 340

Leu Asp Ala Gly Pro Asp Thr Val Val Ile Gly Met Thr Arg Ile Pro
1               5                   10                  15

Val Ile Glu Asn Pro Gln Tyr Phe Arg Gln Gly His Asn Cys His Lys
            20                  25                  30

Pro Asp Thr Tyr Val Gln His Ile Lys Arg Arg Asp Ile Val Leu Lys
        35                  40                  45

Arg Glu Leu Gly Glu Gly Ala Phe
    50                  55

<210> SEQ ID NO 341
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 341

Gly Ala Phe Gly Lys Val Phe Leu Ala
1               5

<210> SEQ ID NO 342
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 342

Val Ile Gly Met Thr Arg Ile Pro Val
1               5

<210> SEQ ID NO 343
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 343

Arg Ile Ala Asp Val Gln His Ile Lys
1               5

<210> SEQ ID NO 344
<211> LENGTH: 9
<212> TYPE: PRT
```

<213> ORGANISM: Artificial Sequence
<220> FEATURE:
<223> OTHER INFORMATION: Synthetic Peptide

<400> SEQUENCE: 344

Glu Leu Gly Glu Gly Ala Phe Gly Lys
1               5

<210> SEQ ID NO 345
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 345

Val Ile Glu Asn Pro Gln Tyr Phe Arg
1               5

<210> SEQ ID NO 346
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 346

Asp Thr Tyr Val Gln His Ile Lys Arg
1               5

<210> SEQ ID NO 347
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 347

Ile Gly Met Thr Arg Ile Pro Val Ile
1               5

<210> SEQ ID NO 348
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 348

Pro Val Ile Glu Asn Pro Gln Tyr Phe
1               5

<210> SEQ ID NO 349
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 349

Pro Pro Glu Glu His Ala Met Pro Ile
1               5

<210> SEQ ID NO 350
<211> LENGTH: 9
<212> TYPE: PRT
<213> ORGANISM: Artificial Sequence

```
<220> FEATURE:
<223> OTHER INFORMATION: Synthetic Peptide

<400> SEQUENCE: 350

Met Pro Ile Gly Arg Ile Ala Asp Val
1               5

<210> SEQ ID NO 351
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 351

Lys Pro Asp Thr Tyr Val Gln His Ile
1               5

<210> SEQ ID NO 352
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 352

His Ile Lys Arg Arg Asp Ile Val Leu
1               5

<210> SEQ ID NO 353
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 353

Val Gln His Ile Lys Arg Arg Asp Ile
1               5

<210> SEQ ID NO 354
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 354

Met Thr Phe Gly Arg Leu His Arg Ile
1               5

<210> SEQ ID NO 355
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 355

Arg Leu His Arg Ile Ile Pro Lys Ile
1               5

<210> SEQ ID NO 356
<211> LENGTH: 9
<212> TYPE: PRT
<213> ORGANISM: Artificial Sequence
<220> FEATURE:
```

```
<223> OTHER INFORMATION: Synthetic Peptide

<400> SEQUENCE: 356

Gly Met Val Gly Gly Gly Pro Pro Ala
1               5

<210> SEQ ID NO 357
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 357

Gln Met Thr Phe Gly Arg Leu His Arg
1               5

<210> SEQ ID NO 358
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 358

Arg Ile Ile Pro Lys Ile Met Pro Lys
1               5

<210> SEQ ID NO 359
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 359

Ile Ile Pro Lys Ile Met Pro Lys Lys
1               5

<210> SEQ ID NO 360
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 360

Gln Ser Gly Pro Pro Pro Pro Pro Arg
1               5

<210> SEQ ID NO 361
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 361

Thr Phe Gly Arg Leu His Arg Ile Ile
1               5

<210> SEQ ID NO 362
<211> LENGTH: 9
<212> TYPE: PRT
<213> ORGANISM: Artificial Sequence
<220> FEATURE:
<223> OTHER INFORMATION: Synthetic Peptide
```

<400> SEQUENCE: 362

His Pro Gln Met Thr Phe Gly Arg Leu
1               5

<210> SEQ ID NO 363
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 363

Met Pro Met Gly Pro Gly Gly Met Asn
1               5

<210> SEQ ID NO 364
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 364

Pro Pro Pro Pro Arg Ser His Asn Met
1               5

<210> SEQ ID NO 365
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 365

Pro Pro Arg Ser His Asn Met Pro Ser
1               5

<210> SEQ ID NO 366
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 366

Gly Thr Met Ala Leu Leu Ala Leu Leu
1               5

<210> SEQ ID NO 367
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 367

Met Ala Leu Leu Ala Leu Leu Leu Val
1               5

<210> SEQ ID NO 368
<211> LENGTH: 9
<212> TYPE: PRT
<213> ORGANISM: Artificial Sequence
<220> FEATURE:
<223> OTHER INFORMATION: Synthetic Peptide

```
<400> SEQUENCE: 368

Ala Leu Leu Ala Leu Leu Val Val
1               5

<210> SEQ ID NO 369
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 369

Leu Leu Val Val Ala Leu Pro Arg Val
1               5

<210> SEQ ID NO 370
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 370

Phe Met Val Ala Lys Gln Cys Ser Ala
1               5

<210> SEQ ID NO 371
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 371

Ser Met Gly Glu Ser Cys Gly Gly Leu
1               5

<210> SEQ ID NO 372
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 372

Gly Leu Trp Leu Ala Ile Leu Leu Leu
1               5

<210> SEQ ID NO 373
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 373

Trp Leu Ala Ile Leu Leu Leu Ala
1               5

<210> SEQ ID NO 374
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 374
```

Ala Ile Leu Leu Leu Ala Ser Ile
1               5

<210> SEQ ID NO 375
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 375

Ile Leu Leu Leu Leu Ala Ser Ile Ala
1               5

<210> SEQ ID NO 376
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 376

Leu Leu Leu Leu Ala Ser Ile Ala Ala
1               5

<210> SEQ ID NO 377
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 377

Leu Leu Ala Ser Ile Ala Ala Gly Leu
1               5

<210> SEQ ID NO 378
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 378

Phe Leu Leu Glu Glu Pro Met Pro Phe
1               5

<210> SEQ ID NO 379
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 379

Leu Ala Leu Leu Leu Val Val Ala Leu
1               5

<210> SEQ ID NO 380
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 380

Lys Ile Phe Pro Arg Phe Phe Met Val
1               5

<210> SEQ ID NO 381
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 381

Leu Leu Leu Val Val Ala Leu Pro Arg
1               5

<210> SEQ ID NO 382
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 382

Arg Val Trp Cys His Val Cys Glu Arg
1               5

<210> SEQ ID NO 383
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 383

Asn Thr Phe Glu Cys Gln Asn Pro Arg
1               5

<210> SEQ ID NO 384
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 384

Lys Trp Thr Glu Pro Tyr Cys Val Ile
1               5

<210> SEQ ID NO 385
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 385

Ala Ala Val Lys Ile Phe Pro Arg Phe
1               5

<210> SEQ ID NO 386
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 386

Leu Trp Leu Ala Ile Leu Leu Leu Leu

```
1               5

<210> SEQ ID NO 387
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 387

Ala Pro Arg Ala Asp Pro Pro Trp Ala
1               5

<210> SEQ ID NO 388
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 388

Arg Ala Asp Pro Pro Trp Ala Pro Leu
1               5

<210> SEQ ID NO 389
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 389

Pro Pro Trp Ala Pro Leu Gly Thr Met
1               5

<210> SEQ ID NO 390
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 390

Trp Ala Pro Leu Gly Thr Met Ala Leu
1               5

<210> SEQ ID NO 391
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 391

Ala Pro Leu Gly Thr Met Ala Leu Leu
1               5

<210> SEQ ID NO 392
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 392

Cys Cys Lys Ile Arg Tyr Cys Asn Leu
1               5
```

<210> SEQ ID NO 393
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 393

Cys Val Ile Ala Ala Val Lys Ile Phe
1               5

<210> SEQ ID NO 394
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 394

Ala Val Lys Ile Phe Pro Arg Phe Phe
1               5

<210> SEQ ID NO 395
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 395

Lys Gln Cys Ser Ala Gly Cys Ala Ala
1               5

<210> SEQ ID NO 396
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 396

Leu Leu Glu Glu Pro Met Pro Phe Phe
1               5

<210> SEQ ID NO 397
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 397

Tyr Leu Lys Cys Cys Lys Ile Arg Tyr
1               5

<210> SEQ ID NO 398
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 398

Trp Leu Ser Gln Pro Pro Ala Arg
1               5

```
<210> SEQ ID NO 399
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 399

Leu Ser Gln Pro Pro Ala Arg Val
1               5

<210> SEQ ID NO 400
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 400

Asp Trp Leu Ser Gln Pro Pro Ala Arg Val
1               5                   10

<210> SEQ ID NO 401
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 401

Trp Leu Ser Gln Pro Pro Ala Arg Val Thr
1               5                   10

<210> SEQ ID NO 402
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 402

Gln Asp Trp Leu Ser Gln Pro Pro Ala Arg Val
1               5                   10

<210> SEQ ID NO 403
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 403

Asp Trp Leu Ser Gln Pro Pro Ala Arg Val Thr
1               5                   10

<210> SEQ ID NO 404
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 404

Trp Leu Ser Gln Pro Pro Ala Arg Val Thr Ile
1               5                   10
```

```
<210> SEQ ID NO 405
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 405

Lys Met Glu Cys Asn Pro Ser Gln
1               5

<210> SEQ ID NO 406
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 406

Met Glu Cys Asn Pro Ser Gln Val
1               5

<210> SEQ ID NO 407
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 407

Ile Lys Met Glu Cys Asn Pro Ser Gln Val
1               5                   10

<210> SEQ ID NO 408
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 408

Lys Met Glu Cys Asn Pro Ser Gln Val Asn
1               5                   10

<210> SEQ ID NO 409
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 409

Thr Ile Lys Met Glu Cys Asn Pro Ser Gln Val
1               5                   10

<210> SEQ ID NO 410
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 410

Ile Lys Met Glu Cys Asn Pro Ser Gln Val Asn
1               5                   10

<210> SEQ ID NO 411
```

```
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 411

Lys Met Glu Cys Asn Pro Ser Gln Val Asn Gly
1               5                   10

<210> SEQ ID NO 412
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 412

Lys Met Val Gly Ser Pro Asp Thr
1               5

<210> SEQ ID NO 413
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 413

Met Val Gly Ser Pro Asp Thr
1               5

<210> SEQ ID NO 414
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 414

Gly Lys Met Val Gly Ser Pro Asp Thr Val
1               5                   10

<210> SEQ ID NO 415
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 415

Lys Met Val Gly Ser Pro Asp Thr Val Gly
1               5                   10

<210> SEQ ID NO 416
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 416

Gly Gly Lys Met Val Gly Ser Pro Asp Thr Val
1               5                   10

<210> SEQ ID NO 417
<211> LENGTH: 11
```

<212> TYPE: PRT
<213> ORGANISM: Artificial Sequence
<220> FEATURE:
<223> OTHER INFORMATION: Synthetic Peptide

<400> SEQUENCE: 417

Gly Lys Met Val Gly Ser Pro Asp Thr Val Gly
1               5                   10

<210> SEQ ID NO 418
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 418

Lys Met Val Gly Ser Pro Asp Thr Val Gly Met
1               5                   10

<210> SEQ ID NO 419
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 419

Val Ile Val Pro Ala Asp Pro Thr
1               5

<210> SEQ ID NO 420
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 420

Ile Val Pro Ala Asp Pro Thr Leu
1               5

<210> SEQ ID NO 421
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 421

Arg Val Ile Val Pro Ala Asp Pro Thr Leu
1               5                   10

<210> SEQ ID NO 422
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 422

Val Ile Val Pro Ala Asp Pro Thr Leu Trp
1               5                   10

<210> SEQ ID NO 423
<211> LENGTH: 11
<212> TYPE: PRT

-continued

```
<213> ORGANISM: Artificial Sequence
<220> FEATURE:
<223> OTHER INFORMATION: Synthetic Peptide

<400> SEQUENCE: 423

Arg Arg Val Ile Val Pro Ala Asp Pro Thr Leu
1               5                   10

<210> SEQ ID NO 424
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 424

Arg Val Ile Val Pro Ala Asp Pro Thr Leu Trp
1               5                   10

<210> SEQ ID NO 425
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 425

Val Ile Val Pro Ala Asp Pro Thr Leu Trp Ser
1               5                   10

<210> SEQ ID NO 426
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 426

Gly Leu Pro Asp Val Asn Ile Leu
1               5

<210> SEQ ID NO 427
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 427

Leu Pro Asp Val Asn Ile Leu Leu
1               5

<210> SEQ ID NO 428
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 428

Tyr Gly Leu Pro Asp Val Asn Ile Leu Leu
1               5                   10

<210> SEQ ID NO 429
<211> LENGTH: 10
<212> TYPE: PRT
<213> ORGANISM: Artificial Sequence
```

<220> FEATURE:
<223> OTHER INFORMATION: Synthetic Peptide

<400> SEQUENCE: 429

Gly Leu Pro Asp Val Asn Ile Leu Leu Phe
1               5                   10

<210> SEQ ID NO 430
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 430

Glu Tyr Gly Leu Pro Asp Val Asn Ile Leu Leu
1               5                   10

<210> SEQ ID NO 431
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 431

Tyr Gly Leu Pro Asp Val Asn Ile Leu Leu Phe
1               5                   10

<210> SEQ ID NO 432
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 432

Gly Leu Pro Asp Val Asn Ile Leu Leu Phe Gln
1               5                   10

<210> SEQ ID NO 433
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 433

Ile Leu Leu Ser His Leu His Tyr
1               5

<210> SEQ ID NO 434
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 434

Leu Leu Ser His Leu His Tyr Leu
1               5

<210> SEQ ID NO 435
<211> LENGTH: 10
<212> TYPE: PRT
<213> ORGANISM: Artificial Sequence
<220> FEATURE:

```
<223> OTHER INFORMATION: Synthetic Peptide

<400> SEQUENCE: 435

Asp Ile Leu Leu Ser His Leu His Tyr Leu
1               5                   10

<210> SEQ ID NO 436
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 436

Ile Leu Leu Ser His Leu His Tyr Leu Arg
1               5                   10

<210> SEQ ID NO 437
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 437

Ala Asp Ile Leu Leu Ser His Leu His Tyr Leu
1               5                   10

<210> SEQ ID NO 438
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 438

Asp Ile Leu Leu Ser His Leu His Tyr Leu Arg
1               5                   10

<210> SEQ ID NO 439
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 439

Ile Leu Leu Ser His Leu His Tyr Leu Arg Glu
1               5                   10

<210> SEQ ID NO 440
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 440

Phe Ile Phe Pro Asn Thr Ser Val
1               5

<210> SEQ ID NO 441
<211> LENGTH: 10
<212> TYPE: PRT
<213> ORGANISM: Artificial Sequence
<220> FEATURE:
<223> OTHER INFORMATION: Synthetic Peptide
```

```
<400> SEQUENCE: 441

Tyr Leu Arg Glu Thr Pro Leu Pro His Leu
1               5                   10

<210> SEQ ID NO 442
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 442

Ile Asp Asp Leu Ser Phe Tyr Val
1               5

<210> SEQ ID NO 443
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 443

Cys Ser Ile Asp Asp Leu Ser Phe Tyr Val
1               5                   10

<210> SEQ ID NO 444
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 444

Ser Ile Asp Asp Leu Ser Phe Tyr Val Asn
1               5                   10

<210> SEQ ID NO 445
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 445

Lys Gly Leu Met Val Tyr Ala Asn Gln Val
1               5                   10

<210> SEQ ID NO 446
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 446

Gly Val Leu Met Thr Asp Ser Asp Phe Val
1               5                   10

<210> SEQ ID NO 447
<211> LENGTH: 10
<212> TYPE: PRT
<213> ORGANISM: Artificial Sequence
<220> FEATURE:
<223> OTHER INFORMATION: Synthetic Peptide
```

-continued

```
<400> SEQUENCE: 447

Val Leu Met Thr Asp Ser Asp Phe Val Ser
1               5                   10

<210> SEQ ID NO 448
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 448

Lys Met Asp Met Ser Asn Ile Val Leu Met
1               5                   10
```